US009132097B2

(12) United States Patent  
Davis et al.

(10) Patent No.: US 9,132,097 B2  
(45) Date of Patent: Sep. 15, 2015

(54) NANOPARTICLES STABILIZED WITH NITROPHENYLBORONIC ACID COMPOSITIONS

(71) Applicant: California Institute of Technology, Pasadena, CA (US)

(72) Inventors: Mark E. Davis, Pasadena, CA (US); Han Han, Belmont, CA (US)

(73) Assignee: California Institute of Technology, Pasadena, CA (US)

( * ) Notice: Subject to any disclaimer, the term of this patent is extended or adjusted under 35 U.S.C. 154(b) by 83 days.

(21) Appl. No.: 13/782,486

(22) Filed: Mar. 1, 2013

(65) Prior Publication Data

US 2014/0249203 A1 Sep. 4, 2014

(51) Int. Cl.
  *A61K 31/427* (2006.01)
  *A61K 31/4745* (2006.01)
  *A61K 31/713* (2006.01)
  *A61K 9/51* (2006.01)
  *A61K 31/337* (2006.01)
  *A61K 9/19* (2006.01)

(52) U.S. Cl.
  CPC .............. *A61K 9/5146* (2013.01); *A61K 31/337* (2013.01); *A61K 31/427* (2013.01); *A61K 31/4745* (2013.01); *A61K 31/713* (2013.01); *A61K 9/19* (2013.01)

(58) Field of Classification Search
  USPC .............. 514/269, 272, 245, 255.06; 544/319
  See application file for complete search history.

(56) References Cited

U.S. PATENT DOCUMENTS

| | | |
|---|---|---|
| 5,693,631 A | 12/1997 | Whittemore et al. |
| 6,034,081 A | 3/2000 | Whittemore et al. |
| 6,060,466 A | 5/2000 | Whittemore et al. |
| 6,645,944 B2 | 11/2003 | Re et al. |
| 7,018,609 B2 | 3/2006 | Pun et al. |
| 7,091,192 B1 | 8/2006 | Davis et al. |
| 7,166,302 B2 | 1/2007 | Pun et al. |
| 7,270,808 B2 | 9/2007 | Cheng et al. |
| 7,427,605 B2 | 9/2008 | Davis et al. |
| 2003/0055212 A1 | 3/2003 | Freund et al. |
| 2004/0023334 A1 | 2/2004 | Prior |
| 2004/0220146 A1 | 11/2004 | Freeman et al. |
| 2006/0134062 A1 | 6/2006 | Huval et al. |
| 2006/0153907 A1 | 7/2006 | Zalipsky et al. |
| 2006/0159736 A1 | 7/2006 | Zalipsky et al. |
| 2006/0263435 A1 | 11/2006 | Davis et al. |
| 2008/0099172 A1 | 5/2008 | Pelton et al. |
| 2009/0169638 A1 | 7/2009 | Davis et al. |
| 2010/0029545 A1 | 2/2010 | Sumerlin et al. |
| 2010/0040556 A1 | 2/2010 | Davis et al. |
| 2011/0086431 A1 | 4/2011 | Lugade et al. |
| 2014/0249202 A1 | 9/2014 | Davis |

FOREIGN PATENT DOCUMENTS

| | | |
|---|---|---|
| WO | WO 2010/019718 A2 | 2/2010 |
| WO | WO 2011/159161 A2 | 12/2011 |
| WO | WO 2014/133547 | 9/2014 |
| WO | WO 2014/133549 | 9/2014 |

OTHER PUBLICATIONS

Altieri et al., "Neutron Autoradiography Imaging of Selective Boron Uptake in Human Metastatic Tumours", Appl Radiat Isotopes, 2008, 66, 1850-1855.
Bartlett et al., "Impact of Tumor-Specific Targeting on the Biodistribution and Efficacy of siRNA Nanoparticles Measured by Multimodality in Vivo Imaging", P Natl Acad Sci USA, 2007, 104, 15549-15554.
Bartlett et al., "Physicochemical and Biological Characterization of Targeted, Nucleic Acid-Containing Nanoparticles", Bioconjugate Chemistry, 2007, 18, 456-468.
Coderre et al., "The Radiation Biology of Boron Neutron Capture Therapy", Radiat Res, 1999, 151, 1-18.
Davis et al., "The First Targeted Delivery of siRNA in Humans via a Self-Assembling, Cyclodextrin Polymer-Based Nanoparticle: From Concept to Clinic", Molecular Pharmaceutics, 2009, 6, 659-668.
Davis et al., "Evidence of RNAi in Humans from Systematically Administered siRNA via Targeted Nanoparticles", Nature, 2010, 1067-1071.
Gatter et al., "Transferrin Receptors in Human Tissues: Their Distribution and Possible Clinical Relevance", 1983, J Clin Pathol, 539-545.
Malek et al., "In Vivo Pharmacokinetics, Tissue Distribution and Underlying Mechanisms of Various PEI(-PEG)/siRNA Complexes", Toxicology and Applied Pharmacology, 2009, 236, 97-108.
Merkel et al., "Stability of siRNA Polyplexes from Poly(ethylenimine) and Poly(ethylenimine)-g-poly(ethlene glycol) Under in Vivo Conditions: Effects on Pharmacokinetics and Biodistribution Measured by Fluorescence Fluctuation Spectroscopy and Single Photon Emission Computed Tomography (SPECT) Imaging", Journal of Controlled Release, 2009, 138, 148-159.
Mikado et al., "Application of Neutron Capture Autoradiography to Boron Delivery Seeking Techniques for Selective Accumulation of Boron Compounds to Tumor with Intra-Arterial Administration of Boron Entrapped Water-in-Oil-Water Emulsion", Nucl Instrum Meth A, 2009, 605, 171-174.
Ogura et al., "Neutron Capture Autoradio Graphic Study of the Biodistribution of B-10 in Tumor-Bearing Mice", Appl Radiat Isotopes, 2004, 61, 585-590.

(Continued)

*Primary Examiner* — Janet Epps-Smith
(74) *Attorney, Agent, or Firm* — Baker & Hostetler LLP

(57) ABSTRACT

Described herein are carrier nanoparticles comprising a polymer containing a polyol coupled to a polymer containing a boronic acid, configured to present the polymer containing a boronic acid to an environment external to the nanoparticle. Targeted versions of the described nanoparticles are also described, as are related compositions, methods and systems.

30 Claims, 25 Drawing Sheets

(56) References Cited

OTHER PUBLICATIONS

Reineke et al., "Structural Effects of Carbohydrate-Containing Polycations on Gene Delivery. 1. Carbohydrate Size and its Distance from Charge Centers", Bioconjugate Chem, 2003, 14, 247-254.
Smith et al., "Quantitative Imaging and Microlocalization of Boron-10 in Brain Tumors and Infiltrating Tumor Cells by SIMS Ion Microscopy: Relevance to Neutron Capture Therapy", Cancer Research, 2001, 61, 8179-8187.
Wittig et al., "Boron Analysis and Boron Imaging in Biological Materials for Boron Neutron Capture Therapy (BNCT)", Crit Rev Oncol Hemet, 2008, 68, 66-90.
Xiao et al., "The Effect of Surface Charge on in Vivo Biodistribution of PEG-oligocholic Acid Based Micellar Nanoparticles", Biomaterials, 2011, 32, 3435-3446.
Allen, T.M. Ligand-Targeted Therapeutics in Anticancer Therapy, Nature, Oct. 2002, 2, 750-763.
Bennett et al., "MRI of the Basement Membrane Using Charged Nanoparticles as Constant Agents", Magnetic Resonance in Medicine, Sep. 2008, 60(3), 564-574.
Chen et al., "Acute Toxicological Effects of Copper Nanoparticles In Vivo", Toxicol. Letters, 2006, 163, 109-120.
Choi et al., "Mechanism of Active Targeting in Solid Tumors With Transferrin-Containing Gold Nanoparticles", PNAS, Jan. 2010, 107(3), 1235-1240.
Choi et al., "Renal Clearance of Quantum Dots", Nat. Biotechnol., Sep. 2007, 25, 1165-1170.
Choi et al., "Tissue and Organ Selective Biodistribution of Nir Fluorescent Quantum Dots", Nano Letters, May 2009, 9, 2354-2359.
Dan et al., "Polymers Tethered to Curves Interfaces: A Self-Consistent-Field Analysis", Macromolecules, 25, May 1992, 2890-2895.
Davis et al., "Nanoparticle T herapeutics: An Emerging Treatment Modality for Cancer", Nat. Rev. Drug Discov., Sep. 2008, 7, 771-782.
Duncan, R., Polymer Conjugates as Anticancer Nanomedicines, Nature, Sep. 2006, 6, 688-701.
Fujita, N. et al., "Boronic Acids in Molecular Self-Assembly", *Chem. Asian J.*, 2008, 3, 1076-1091.
Goldman, C.K. et al., "In Vitro and In Vivo Gene Delivery Mediated by a Synthetic Polycationic Amino Polymer", Nature, Biotechnology, May 1997, 15, 462-466.
Gosh, P., et al., "Gold Nanoparticles in Delivery Applications", 2008, Adv., Drug Deliv. Rev., 1307-1315.
Haddad, E., et al., "Enhanced Expression of the CD71 Mesangial IgA1 Receptor in Berger Disease and Henoch-Scho""nlein Nephritis: Association between CD71 Expression and IgA Deposits", 2003, JASN, 327-337.
International Search Report for PCT/US2009/053620 filed Aug. 12, 2009 in the name of California Institute of Technology.
Kanwar et al., Presence of Heparin Sulfate in the Glomerular Basement Membrane, Proc. Natl. Acad. Sci., Mar. 1979, 76, 1303-1307.
L'Azou et al., "In Vitro Effects of Nanoparticles on Renal Cells", Part. Fibre. Toxicol., Jul. 2008, 5, 1-14.
Landenkari et al., "Podocytes Are Firmly Attached to Glomerular Basement Membrane in Kidneys With Heavy Proteinuria", J. Am. Soc. Nephrol., 2004, 15, 2611-2618.
Lee et al., "Effective Gene Silencing by Multilayered siRNA-coated Gold Nanoparticles", Small, Feb. 2011, 7(3), 364-370.
Li, J., et al., "In Vitro Cancer Cell Imaging and Therapy Using Transferrin-Conjugated Gold Nanoparticles", 2009, Cancer Letters, 319-326.
Linehan et al., "Mannose Receptor an Its Putative Ligands in Normal Murine Lymphoid and Nolymphoid Organs: In Situ Expression of Mannose Receptor by Selected Macrphages, Endothelial Cells, Perivascular Microglia, and mesangial Cells, but not Dendritic Cells", J. Exp. Med., Jun. 21, 1999, 1961-1972.
Liu, Y. et al., "Hydroxyl Stereochemistry and Amine Number within Poly(glycoamidoamine)s Affect Intracellular DNA Delivery", J. Am. Chem. Soc., 2005, 127, 3004-3015.
Luft et al., "Effects of Moxalactam and Cefotaxime on Rabbit Renal Tissue", Antimicrob. Agents Chemother, Feb. 1982, 21, 830-835.
Lytton-Jean et al., "Five Years of siRNA delivery: Spotlight on gold nanoparticles", Small, 2011, 7(14), 1932-1937.
Office Action issued for China Patent Application No. 200980131484.0 filed Feb. 12, 2011 dated Feb. 21, 2012 with English translation attached.
Ogawa et al., "High Resolution Ultrastructural Comparison of Renal Glomerular and Tubular Basement Membranes", Am. J. Nephrol., 1999, 19, 686-693.
Peer et al., "Nanocarriers as an Emerging Platform for Cancer Therapy", Nat. Nanotechnol., Dec. 2007, 2, 751-760.
Phillips et al., "Targeting HER2-Positive Breast Cancer with Trastuzumab-DM1, an Antibody-Cytotoxic Drug Conjugated", Cancer Res, Nov. 2008, 68, 9280-9290.
Pisarev, M.A. et al., "Boron Neutron Capture Therapy in Cancer: Past, Present and Future", 2007, 852-856.
Pun et al., "Targeted Delivery of RNA-Cleaving DNA Enzyme (DNAzyme) to Tumor Tissue by Transferrin-Modified, Cyclodextrin-Based Particles", Cancer Biology and Therapy, 3, 7, Jul. 2004, 641-650.
Ruggiero et al., "Paradoxical Glomerular Filtration of Carbon Nanotubes", Proc. Natl. Acad. Sci., Jul. 2010, 107(27), 12369-12374.
Sadauskas et al., "Kupffer Cells Are Central in the Removal of Nanoparticles From the Organism", Part. Fibre. Toxicol., Oct. 2007, 4, 1-7.
Sakai et al., "The Structural Relationship Between Mesangial Cells and Basement Membrane of the Renal Glomerus", Anat. Embroyol., 1987, 176, 373-386.
Sapsford et al., "Functionalizing Nanoparticles with Biological Molecules: Developing Chemistries that Facilitate Nanotechnology", Chemical Reviews, Feb. 22, 2013, 113, 1904-2074.
Schipper et al., "Particle Size, Surface Coating, and Pegylation Influence the Biodistribution of Quantum Dots Living in Mice", Small, Jan. 2009, 126-134.
Shimizu et al., "siRNA-Based Therapy Ameliorates Glomerulonephritis", J. Am. Soc. Nephrol., 2010, 21, 622-633.
Shimizu et al., "New Short Interfering Rna-Based Therapies for Glomerulonephritis", Nature Reviews, May 24, 2011, 1-9.
Torchilin et al., "TAT Peptide on the Surface of Liposomes Affords Their Efficient Intracellular Delivery Even at Low Temperature and in the Presence of Metabolic Inhibitors", PNAS, Jul. 2001, 98(15), 8786-8791.
Tan et al., "An Effective Targeted Nanoglobular Manganese(II) Chelate Conjugate for Magnetic Resonance Molecular Imaging of Tumor Extracellular Martrix", Mol. Pharm., 2010, 7, 936-943.
Tuffin et al., "Immunoliposome Targeting to Mesangial Cells: A Promising Strategy for Specific Drug Delivery to the Kidney", J. Am. Soc. Nephrol., 2005, 16, 3295-3305.
Vicent, M.J. et al., "Polymer Conjugates: Nanosized Medicines for Treating Cancer", *Trends in Biotechnology*, Jan. 2006, 24(1), 40-47.
Wolf, W. et al., "F-MRS Studies of Fluorinated Drugs in Humans", Advanced Drug Delivery Reviews, 2000, 41, 55-74.
Written Opinion for PCT/US2009/053620 filed Aug. 12, 2009 in the name of California Institute of Technology.
Zimmerman et al., "RNAi-Mediated Gene Silencing in Non-Human Primates", Nature, Jan. 2006, 441, 111-114.

| Polymer | Effective Diameter (nm) | Zeta Potential (mV) |
|---|---|---|
| poly(Mucic Acid-DiCys-PEG) | 4.8 | -5 |
| poly(Mucic Acid-DiCys-PEG)-CPT | 57 | -8 |

FIG. 14

```
                        SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 1
gugccagagu ccuucgauau t                                              21

<210> SEQ ID NO 2
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 2
uaucgaagga cucuggcact t                                                    21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uagcgacuaa acacaucaau u                                                    21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uugauguguu uagucgcuau u                                                    21
```

NANOPARTICLES STABILIZED WITH NITROPHENYLBORONIC ACID COMPOSITIONS

GOVERNMENT RIGHTS

This invention was made with government support under Grant No. CA 151819 and under Grant No. CA 119347 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 23, 2013, is named Sequence_Listing_CRF_CTEK0114 and is 1,539 bytes in size.

TECHNICAL FIELD

The present disclosure relates to carrier nanoparticles and in particular to nanoparticles suitable for delivering compounds of interest, and related compositions, methods and systems.

BACKGROUND

Effective delivery of compounds of interest to cells, tissues, organs, and organisms has been a challenge in biomedicine, imaging and other fields where delivery of molecules of various sizes and dimensions to a predetermined target is desirable.

Whether for pathological examination, therapeutic treatment or for fundamental biology studies, several methods are known and used for delivering various classes of biomaterials and biomolecules which are typically associated with a biological and/or chemical activity of interest.

As the number of molecules suitable to be used as chemical or biological agents (e.g. drugs, biologics, therapeutic or imaging agents) increases, development of a delivery systems suitable to be used with compounds of various complexity, dimensions and chemical nature has proven to be particularly challenging.

Nanoparticles are structures useful as carriers for delivering agents with various methods of delivery. Several nanoparticle delivery systems exist, which utilize an array of different strategies to package, transport, and deliver an agent to specific targets.

SUMMARY

Provided herein are nanoparticles and related compositions, methods and systems that in several embodiments provide a multifunctional tool for effective and specific delivery of a compound of interest. In particular, in several embodiments, nanoparticles herein described can be used as a flexible system for carrying and delivering a wide range of molecules of various sizes, dimensions and chemical nature to predetermined targets.

According to one aspect, a nanoparticle comprising a polymer containing a polyol and to a polymer containing a boronic acid is described. In the nanoparticle, the polymer containing a boronic acid is coupled to the polymer containing a polyol and the nanoparticle is configured to present the polymer containing a boronic acid to an environment external to the nanoparticle. One or more compounds of interest can be carried by the nanoparticle, as a part of or attached to the polymer containing a polyol and/or the polymer containing a boronic acid.

According to another aspect, a composition is described. The composition comprises a nanoparticle herein described and a suitable vehicle and/or excipient.

According to another aspect, a method to deliver a compound to a target is described. The method comprises contacting the target with a nanoparticle herein described wherein the compound is comprised in the polymer containing a polyol or in the polymer containing a boronic acid of the nanoparticle herein described.

According to another aspect, a system to deliver a compound to a target is described. The system comprises at least a polymer containing a polyol and polymer containing a boronic acid capable of reciprocal binding through a reversible covalent linkage, to be assembled in a nanoparticle herein described comprising the compound.

According to another aspect, a method to administer a compound to an individual is described. The method comprises administering to the individual an effective amount of a nanoparticle herein described, wherein the compound is comprised in the polymer containing a polyol and/or in the polymer containing a boronic acid.

According to another aspect, a system for administering a compound to an individual is described. The system comprises, at least a polymer containing a polyol and polymer containing a boronic acid capable of reciprocal binding through a reversible covalent linkage, to be assembled in a nanoparticle herein described attaching the compound to be administered to the individual according to methods herein described.

According to another aspect, a method to prepare a nanoparticle comprising a polymer containing a polyol and a polymer containing a boronic acid is described. The method comprises contacting the polymer containing polyols with the polymer containing a boronic acid for a time and under condition to allow coupling of the polymer containing polyoly with the polymer containing a boronic acid.

According to another aspect, several polymer containing a boronic acid are described which are illustrated in details in the following sections of the present disclosure.

According to another aspect, several polymers containing polyols are described, which are illustrated in details in the following sections of the present disclosure.

Also described herein are nanoparticles having a polymer containing a polyol that are conjugated to polymers having a nitrophenylboronic acid group, which enhances the stability of the nanoparticle by reducing its pKa.

Another aspect of the present disclosure provides a description of targeted nanoparticles that, in some embodiments, can have only one single targeting ligand, which is capable of promoting delivery of the nanoparticle to a particular target, such as a cell expressing a binding partner for the targeting ligand of the particle. Targeted nanoparticles of this sort have advantages over nanoparticles with a plurality of targeting ligands, such as having a smaller overall size, due to having fewer surface ligands, and have fewer ligands to mediate nonspecific binding through avidity-based interactions, rather than affinity-based interactions. Additionally, nanoparticles that contain or carry a therapeutic agent can be successfully targeted to location of interest (such as a cell or tissue) using only a single targeting ligand, thereby delivering the therapeutic agent to the target at a very high targeting ligand-to-therapeutic ratio. This aspect of the described nanoparticles can significantly increase the efficiency of making such therapeutics while also reducing the need to employ a high number of costly antibodies to mediate targeting.

Nanoparticles herein described and related compositions, methods, and systems can be used in several embodiments as a flexible molecular structure suitable for carrying compounds of various sizes, dimensions and chemical nature.

Nanoparticles herein described and related compositions, methods, and systems can be used in several embodiments as delivery systems which can provide protection of the carried compound from degradation, recognition by immune system and loss due to combination with serum proteins or blood cells.

Nanoparticles herein described and related compositions, methods, and systems can be used in several embodiments as delivery systems characterized by steric stabilization and/or ability to deliver the compound to specific targets such as tissues, specific cell types within a tissue and even specific intracellular locations within certain cell types.

Nanoparticles herein described and related compositions, methods, and systems can be designed in several embodiments, to release a carried compound in a controllable way, including controlled release of multiple compounds within a same nanoparticle at different rates and/or times.

Nanoparticles herein described and related compositions, methods, and systems can be used in several embodiments, to deliver compounds with enhanced specificity and/or selectivity during targeting and/or enhanced recognition of the compound by the target compared to certain systems of the art.

Nanoparticles herein described and related compositions, methods, and systems can be used in several embodiments in connection with applications wherein controlled delivery of a compound of interest is desirable, including but not limited to medical applications, such as therapeutics, diagnostics and clinical applications. Additional applications comprise biological analysis, veterinary applications, and delivery of compounds of interest in organisms other than animals, and in particular in plants.

The details of one or more embodiments of the disclosure are set forth in the accompanying drawings and the detailed description and examples below. Other features, objects, and advantages will be apparent from the detailed description, examples and drawings, and from the appended claims

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 3, shows results of a MAP gel retardation assay with plasmid DNA according to an embodiment of the present disclosure. A DNA ladder is loaded in Lane 1. Lanes 2-8 show plasmid DNA combined with MAP of incrementally increased charge ratio. Charge ratio is defined as the amount of positive charges on the MAP divided by the amount of negative charges on the nucleic acid.

FIG. 4 shows results of a MAP gel retardation assay with siRNA according to an embodiment of the present disclosure. A DNA ladder is loaded in Lane 1. Lanes 2-8 show siRNA combined with MAP of incrementally increased charge ratio.

FIG. 5 shows a diagram illustrating a plot of particle size (determined from dynamic light scattering (DLS) measurements) versus charge ratio and zeta potential (a property that relates to the surface charge of the nanoparticle) versus charge ratio for MAP-plasmid nanoparticles according to an embodiment of the present disclosure.

FIG. 6 shows a diagram illustrating a plot of particle size (DLS) versus charge ratio and zeta potential versus charge ratio for BA-PEGylated MAP-plasmid nanoparticles according to an embodiment of the present disclosure.

FIG. 8 shows a diagram illustrating a plot of relative light units (RLU) that are a measure of the amount of luciferase protein expressed from the pGL3 plasmid that has been delivered to the cells versus charge ratio for a MAP/pGL3 transfection into HeLa Cells according to an embodiment of the present disclosure.

FIG. 9, shows a diagram illustrating a plot of cell survival versus charge ratio after a MAP/pGL3 transfection according to an embodiment of the present disclosure. The survival data are for the experiments shown in FIG. 8.

FIG. 10 shows a diagram illustrating a plot of relative light units (RLU) versus particle type for a co-transfection of MAP Particles containing pGL3 and siGL3 at a charge ratio of 5+/− into HeLa Cells according to an embodiment herein described. The wording siCON indicates an siRNA with a control sequence.

FIG. 11 shows a plot of relative light units (RLU) versus siGL3 concentration for a delivery of MAP/ siGL3 at a charge ratio of 5+/− into HeLa-Luc cells according to an embodiment of the present disclosure.

FIG. 12, show a schematic for a synthesis of boronic acid-PEG disulfide-Transferrin according to an embodiment of the present disclosure.

FIG. 13 shows a schematic for a formulation of a nanoparticle with Campothecin Mucic acid polymer (CPT-mucic acid polymer) in water according to an embodiment of the present disclosure.

FIG. 14 shows a table summarizing particle sizes and zeta potentials of nanoparticles formed from the CPT-mucic acid polymer conjugated in water, prepared according to an embodiment of the present disclosure.

FIG. 15 shows a formulation of a boronic acid-PEGylated nanoparticle with CPT-Mucic Acid Polymer and boronic acid-disulfide-$PEG_{5000}$ in water according to an embodiment of the present disclosure.

DETAILED DESCRIPTION OF ILLUSTRATIVE EMBODIMENTS

Figure 1:
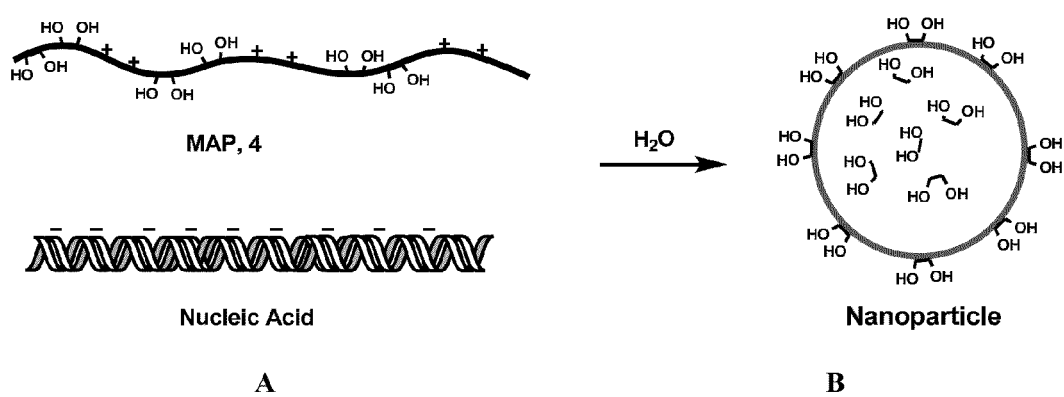
FIG. 1 shows a schematic representation of a nanoparticle and a related method for the relevant formation in absence of a boronic acid containing compound. Panel A shows a schematic representation of a polymer containing a polyol (MAP, 4) and a compound of interest (nucleic acid) according to an embodiment herein described. Panel B shows a nanoparticle formed upon assembly of the polymer containing a polyol and compound shown in panel A.

Provided herein are nanoparticles and related compositions, methods, and systems that can be used in connection for delivering a compound of interest (herein also cargo) comprised in the nanoparticles, methods for producing the described nanoparticles, methods of treatment using the described nanoparticles, and kits for assembling the described nanoparticles.

The term "nanoparticle" as used herein indicates a composite structure of nanoscale dimensions. In particular, nanoparticles are typically particles of a size in the range of from about 1 to about 1000 nm, and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 1000 nm, where the specific diameter depends on the nanoparticle composition and on the intended use of the nanoparticle according to the experimental design. For example, nanoparticles to be used in several therapeutic applications typically have a size of about 200 nm or below, and the ones used, in particular, for delivery associated to cancer treatment typically have a diameter from about 1 to about 100 nm. The term "targeted nanoparticle" denotes a nanoparticle that is conjugated to a targeting agent or ligand.

Additional desirable properties of the nanoparticle, such as surface charges and steric stabilization, can also vary in view of the specific application of interest. Some of the exemplary properties that can be desirable in clinical applications such as cancer treatment have been described in the scientific literature. Additional properties are identifiable by a skilled person upon reading of the present disclosure. Nanoparticle dimensions and properties can be detected by techniques known in the art. Exemplary techniques to detect particles dimensions include but are not limited to dynamic light scattering (DLS) and a variety of microscopies such at transmission electron microscopy (TEM) and atomic force microscopy (AFM). Exemplary techniques to detect particle morphology include but are not limited to TEM and AFM. Exemplary techniques to detect surface charges of the nanoparticle include but are not limited to zeta potential method. Additional techniques suitable to detect other chemical properties comprise by $^1$H, $^{11}$B, and $^{13}$C and $^{19}$F NMR, UV/Vis and infrared/Raman spectroscopies and fluorescence spectroscopy (when nanoparticle is used in combination with fluorescent labels) and additional techniques identifiable by a skilled person.

Nanoparticles and related compositions, methods, and systems herein described can be used to deliver a compound of interest and in particular an agent to a predetermined target.

The term "deliver" and "delivery" as used herein indicates the activity of affecting the spatial location of a compound, and in particular controlling said location. Accordingly, delivering a compound in the sense of the present disclosure indicates the ability to affect positioning and movement of the compound at a certain time under a certain set of conditions, so that the compound's positioning and movement under those conditions are altered with respect to the positioning and movement that the compound would otherwise have.

In particular, delivery of a compound with respect to a reference endpoint indicates the ability to control positioning and movement of the compound so that the compound is eventually positioned on the selected reference endpoint. In an in vitro system, delivery of a compound is usually associated to a corresponding modification of the chemical and/or biological detectable properties and activities of the compound. In an in vivo system, delivery of a compound is also typically associated with modification of the pharmacokinetics and possibly pharmacodynamics of the compound.

Pharmacokinetic of a compound indicates absorption, distribution, metabolism and excretion of the compound from the system, typically provided by the body of an individual. In particular the term "absorption" indicates the process of a substance entering the body, the term "distribution" indicates the dispersion or dissemination of substances throughout the fluids and tissues of the body, the term "metabolism" indicates the irreversible transformation of parent compounds into daughter metabolites and the term "excretion" indicates the elimination of the substances from the body. If the compound is in a formulation, pharmacokinetics also comprises liberation of the compound from the formulation which indicates process of release of the compound, typically a drug, from the formulation. The term "pharmacodynamic" indicates physiological effects of a compound on the body or on microorganisms or parasites within or on the body and the mechanisms of drug action and the relationship between drug concentration and effect. A skilled person will be able to identify the techniques and procedures suitable to detect pharmacokinetics and pharmacodynamic features and properties of a compound of interest and in particular of an agent of interest such as a drug.

The term "agent" as used herein indicates a compound capable of exhibiting a chemical or biological activity associated to the target. The term "chemical activity" as used herein indicates the ability of the molecule to perform a chemical reaction. The term biological activity as used herein indicates the ability of the molecule to affect a living matter. Exemplary chemical activities of agents comprise formation of a covalent or electrostatic interaction. Exemplary biological activities of agents comprise production and secretion of endogenous molecules, absorption and metabolization of endogenous or exogenous molecules and activation or deactivation of genetic expression including transcription and translation of a gene of interest.

The term "target" as used herein indicates a biological system of interest including unicellular or pluricellular living organisms or any portion thereof and include in vitro or in vivo biological systems or any portion thereof.

The nanoparticles herein described a polymer containing a boronic acids is coupled to a polymer containing a polyol is arranged in the nanoparticle to be presented to an environment external to the nanoparticle.

The term a "polymer" as used herein indicates a large molecule composed of repeating structural units typically connected by covalent chemical bonds. A suitable polymer may be a linear and/or branched, and can take the form of a homopolymer or a co-polymer. If a co-polymer is used, the co-polymer may be a random copolymer or a branched co-polymer. Exemplary polymers comprise water-dispersible and in particular water soluble polymers. For example, suitable polymers include, but are not limited to polysaccharides, polyesters, polyamides, polyethers, polycarbonates, polyacrylates, etc. For therapeutic and/or pharmaceutical uses and applications, the polymer should have a low toxicity profile and in particular that are not toxic or cytotoxic. Suitable polymers include polymers having a molecular weight of about 500,000 or below. In particular, suitable polymers can have a molecular weight of about 100,000 and below.

The term "polymer containing a polyol" or "polyol(s) polymer" as used herein indicates a polymer presenting multiple hydroxyl functional groups. In particular, the polymer containing a polyol suitable to form the nanoparticles here described comprise polymers presenting at least a portion of the hydroxyl functional groups for a coupling interaction with at least one boronic acid of a polymer containing a boronic acid.

The term "present" as used herein with reference to a compound or functional group indicates attachment performed to maintain the chemical reactivity of the compound or functional group as attached. Accordingly, a functional group presented on a surface, is able to perform under the appropriate conditions the one or more chemical reactions that chemically characterize the functional group.

Structural units forming polymers containing polyols comprise monomeric polyols such as pentaerythritol, ethylene glycol and glycerin. Exemplary polymers containing polyols comprise polyesters, polyethers and polysaccharides. Exemplary suitable polyethers include but are not limited to diols and in particular diols with the general formula HO—$(CH_2CH_2O)_p$—H with $p \geq 1$, such as polyethylene glycol, polypropylene glycol, and poly(tetramethylene ether) glycol. Exemplary, suitable polysaccharides include but are not limited to cyclodextrins, starch, glycogen, cellulose, chitin and $\beta$-Glucans. Exemplary, suitable polyesters include but are not limited to polycarbonate, polybutyrate and polyethylene terephthalate, all terminated with hydroxyl end groups. Exemplary polymers containing polyols comprise polymers of about 500,000 or less molecular weight and in particular from about 300 to about 100,000.

Several polymers containing polyols are commercially available and/or can be produced using techniques and procedures identifiable by a skilled person. Exemplary procedures for the synthesis of an exemplary polyol polymer have been described previously in the scientific literature, and others are illustrated in Examples 1-4. Additional procedures for making polymer containing polyols will be identifiable by a skilled person in view of the present disclosure.

The term "polymer containing a boronic acid" or "BA polymer" as used herein indicates polymer containing at least one boronic acid group presented for binding to a hydroxyl group of a polymer containing polyols. In particular, polymers containing boronic acids of the nanoparticles herein described include a polymer comprising in at least one structural unit an alkyl or aryl substituted boronic acid containing a carbon to boron chemical bond. Suitable BA polymers comprise polymers wherein boronic acid is in a terminal structural unit or in any other suitable position to provide the resulting polymer with hydrophilic properties. Exemplary polymers containing polyols comprise polymers of about 40,000 or less molecular weight and in particular of about 20,000 or less, or about 10,000 or less.

Several polymer containing a boronic acids are commercially available and/or can be produced using techniques and procedures identifiable by a skilled person. Exemplary procedures for the synthesis of an exemplary polyol polymer have been described previously in the scientific literature and other new ones are illustrated in Examples 5-8. Additional procedures for making BA polymers will be identifiable by a skilled person in view of the present disclosure.

In the nanoparticles herein described polyols polymers are coupled to the BA polymers. The term "coupled" or "coupling" as used herein with reference to attachment between two molecules indicates an interaction forming a reversible covalent linkage. In particular, in presence of a suitable medium, a boronic acid presented on the BA polymer interact with hydroxyl groups of the polyols via a rapid and reversible pair-wise covalent interaction to form boronic esters in a suitable medium. Suitable medium include water and several aqueous solutions and additional organic media identifiable by a skilled person. In particular, when contacted in an aqueous medium BA polymers and polyols polymers react, producing water as a side product. The boronic acid polyol interaction is generally more favorable in aqueous solutions but is also known to proceed in organic media. In addition, cyclic esters formed with 1,2 and 1,3 diols are generally more stable than their acyclic ester counterparts.

Accordingly, in a nanoparticle herein described, at least one boronic acid of the polymer containing a boronic acid is bound to hydroxyl groups of the polymer containing a polyol with a reversible covalent linkage. Formation of a boronic ester between BA polymers and polyols polymers can be detected by methods and techniques identifiable by a skilled person such as boron-11 nuclear magnetic resonance ($^{11}B$ NMR), potentiomeric titration, UV/Vis and fluorescent detection techniques whereby the technique of choice is dependent on the specific chemical nature and properties of the boronic acid and polyol composing the nanoparticle.

A nanoparticle resulting from coupling interactions of a BA polymer herein described with a polyol polymer herein described presents the BA polymer on the surface of the particle. In several embodiments the nanoparticles can have a diameter from about 1 to about 1000 nm and a spherical morphology although the dimensions and morphology of the particle are largely determined by the specific BA polymer and polyol polymers used to form the nanoparticles and by the compounds that are carried on the nanoparticles according to the present disclosure.

In several embodiments the compound of interest carried by the nanoparticle forms part of the BA polymer and/or the polyol polymers. Examples of such embodiments are provided by nanoparticles wherein one or more atoms of a polymer is replaced by a specific isotope e.g., $^{19}F$ and $^{10}B$, and are therefore suitable as agent for imaging the target and/or providing radiation treatment to the target.

In several embodiments, the compound of interest carried the nanoparticle is attached to a polymer, typically a polyol polymer, through covalent or non-covalent linkage. Examples of such embodiments are provided by nanoparticles wherein one or more moieties in at least one of the polyol polymer and BA polymer attaches one or more compounds of interest.

The term "attach", "attached" or "attachment" as used herein, refers to connecting or uniting by a bond, link, force or tie in order to keep two or more components together, which encompasses either direct or indirect attachment such that for example where a first compound is directly bound to a second compound, and the embodiments wherein one or more intermediate compounds, and in particular molecules, are disposed between the first compound and the second compound.

In particular, in some embodiments a compound can be attached to the polyol polymer or BA polymer through covalent linkage of the compound to suitable moieties of the polymer. Exemplary covalent linkages are illustrated in Example 19 where, attachment of the drug Camptothecin to Mucic Acid polymer is performed through biodegradable ester bond linkage, and in Example 9, wherein attachment of transferrin to BA-PEG$_{5000}$ is performed through pegylation of the transferrin.

In some embodiments, the polymer can be designed or modified to enable the attachment of a specific compound of interest, for example by adding one or more functional groups able to specifically bind a corresponding functional group on the compound of interest. For example, in several embodiments it is possible to PEGylate the nanoparticle with a BA-PEG-X, where X can be a Maleimide or an iodoacetyl group or any leaving group that will react specifically with a thiol or non-specifically with an amine. The compound to be attached can then react to the maleimide or iodoacetyl groups after modification to express a thiol functional group. The compound to be attached can also be modified with aldehydes or ketone groups and these can react via a condensation reaction with the diols on the polyols to give acetals or ketals.

In some embodiments, a compound of interest can be attached to the polyol polymer or BA polymer through non covalent bonds such as ionic bonds and intermolecular interactions, between a compound to be attached and a suitable moiety of the polymer. Exemplary non covalent linkages are illustrated in Example 10.

A compound of interest can be attached to the nanoparticle before, upon or after formation of the nanoparticle, for example via modification of a polymer and/or of any attached compound in the particulate composite. Exemplary procedures to perform attachment of a compound on the nanoparticle are illustrated in the Examples section. Additional procedures to attach a compound to a BA polymer polyol polymer or other components of the nanoparticle herein described (e.g. a previously introduced compound of interest) can be identified by a skilled person upon reading of the present disclosure.

In some embodiments, at least one compound of interest attached to a BA polymer presented on the nanoparticle herein described is an agent that can be used as a targeting ligand. In particular, in several embodiments, the nanoparticle attaches on the BA polymer one or more agents to be used as a targeting ligand, and on the polyol polymer and/or the BA polymer, one or more agents to be delivered to a target of choice.

The term "targeting ligand" or "targeting agent" as used in the present disclosure indicates any molecule that can be presented on the surface of a nanoparticle for the purpose of engaging a specific target, and in particular specific cellular recognition, for example by enabling cell receptor attachment of the nanoparticle. Examples of suitable ligands include, but are not limited to, vitamins (e.g. folic acid), proteins (e.g. transferrin, and monoclonal antibodies), monosaccharides (e.g. galactose), peptides, and polysaccharides. In particular targeting ligands can be antibodies against certain surface cell receptors such as anti-VEGF, small molecules such as folic acid and other proteins such as holo-transferrin.

The choice of ligand, as one of ordinary skill appreciates, may vary depending upon the type of delivery desired. As another example, the ligand may be membrane permeabilizing or membrane permeable agent such as the TAT protein from HIV-1. The TAT protein is a viral transcriptional activation that is actively imported into the cell nucleus. Torchilin, V. P. et al, PNAS. 98, 8786 8791, (2001). Suitable targeting ligands attached to a BA polymer typically comprise a flexible spacer such as a poly(ethylene oxide) with a boronic acid attached to its distal end (see Example 9).

In several embodiments, at least one of the compounds comprised or attached to the polyol polymer and/or BA polymer (including a targeting ligand) can be an agent and in particular a drug, to be delivered to a target, for example an individual, to which the chemical or biological activity, e.g. the therapeutic activity, is to be exerted.

Selection of a polyol polymer and a BA polymer suitable to form a nanoparticle herein described can be performed in view of the compound and the target of interest. In particular, selection of a suitable polymer containing a polyol and a suitable BA polymer to form a nanoparticle herein described can be performed by providing candidate polyol polymers and BA polymer, and selecting the polyol polymer and the BA polymer able to form a coupling interaction in the sense of the disclosure, wherein the selected BA polymer and polyol polymer have a chemical composition such that in view of the compound of interest and targeting ligand to comprised or attached to the polyol polymers and/or the BA polymers, the polyol polymers is less hydrophilic than the BA polymer. Detection of the BA polymer on the surface of the nanoparticle and related presentation on the environment external to the nanoparticle can be performed by detection of the zeta potential which can demonstrate modification of the surface of the nanoparticle as illustrated in Example 12. (see in particular FIG. 6) Additional procedures to detect the surface charge of the particles and the stability of the particles in salt solutions, include detection of changes of the particle size such as the ones exemplified in Example 12 (see in particular FIG. 7) and additional procedures identifiable by a skilled person In several embodiments, polymers containing polyols comprise one or more of at least one of the following structural units

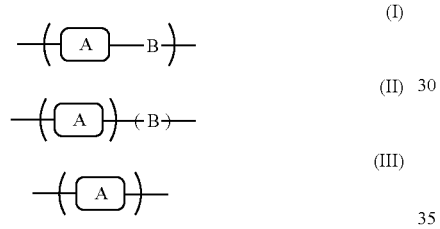

wherein
A is an organic moiety of formula

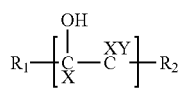

in which
R$_1$ and R$_2$ are independently selected from any carbon based or organic group with a molecular weight of about 10 kDa or less;
X is independently selected from an aliphatic group, containing one or more of —H, —F, —C, —N or —O; and
Y is independently selected from —OH or an organic moiety bearing a hydroxyl (—OH) group including but not limited to —CH$_2$OH, —CH$_2$CH$_2$OH, —CF$_2$OH, —CF$_2$CF$_2$OH, and C(R$_1$G$_1$)(RG$_2$)(R$_1$G$_3$)OH, with R$_1$G$_1$, R$_1$G$_2$ and R$_1$G$_3$ are independently organic based functionalities,
and
B is an organic moiety linking one of R$_1$ and R$_2$ of a first A moiety with one of the R$_1$ and R$_2$ of a second A moiety.

The term "moiety" as used herein indicates a group of atoms that constitute a portion of a larger molecule or molecular species. In particular, a moiety refers to a constituent of a repeated polymer structural unit. Exemplary moieties include acid or base species, sugars, carbohydrates, alkyl groups, aryl groups and any other molecular constituent useful in forming a polymer structural unit.

The term "organic moiety" as used herein indicates a moiety which contains a carbon atom. In particular, organic groups include natural and synthetic compounds, and compounds including heteroatoms. Exemplary natural organic moieties include but are not limited to most sugars, some alkaloids and terpenoids, carbohydrates, lipids and fatty acids, nucleic acids, proteins, peptides and amino acids, vitamins and fats and oils. Synthetic organic groups refer to compounds that are prepared by reaction with other compounds.

In several embodiments, one or more compounds of interest can be attached to (A), to (B) or to (A) and (B).

In several embodiments, R$_1$ and R$_2$ independently have the formula:

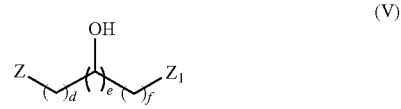

wherein
d is from 0 to 100
e is from 0 to 100
f is from 0 to 100,
Z is a covalent bond that links one organic moiety to another and in particular to another moiety A or a moiety B as herein defined. and
Z$_1$ is independently selected from —NH$_2$, —OH, —SH, and —COOH In several embodiments, Z can independently be selected from —NH—, —C(=O)NH—, —NH—C(=O), —SS—, —C(=O)O—, —NH(=NH$_2$$^+$)— or —O—C(=O)—

In several embodiments where the structural unit A of a polymer containing a polyol has formula (IV), X can be C$_v$H$_{2v+1}$, where v=0-5 and Y can be —OH In some embodiments, R1 and/or R2 have formula (V) where Z is —NH(=NH$_2$$^+$)— and/or Z$_1$ is NH$_2$.

In several embodiments, in polymers containing a polyol of the particle herein described (A) can be independently selected from the formulas

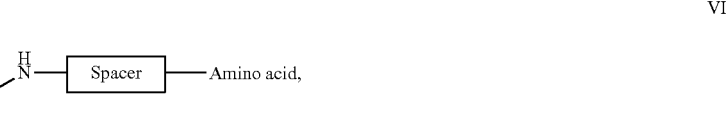

-continued

VII

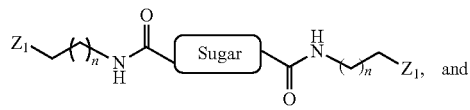, and

VIII

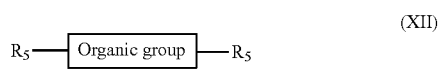

wherein
- the spacer is independently selected from any organic moiety, and in particular can include alkyl, phenyl or alkoxy groups optionally containing a heteroatom, such as sulfur, nitrogen, oxygen or fluorine;
- the amino acid is selected from any organic group bearing a free amine and a free carboxylic acid group;
- n is from 1 to 20; and
- $Z_1$ is independently selected from —$NH_2$, —OH, —SH, and —COOH.

In several embodiments, Z1 is NH2, and/or the sugar can be any monosaccharide such as glucose, fructose, mannitol, sucrose, galactose, sorbitol, xylose or galactose.

In several embodiments, in polymers containing a polyol of the particle herein described one ore more structural units (A) can independently have the formula

IX

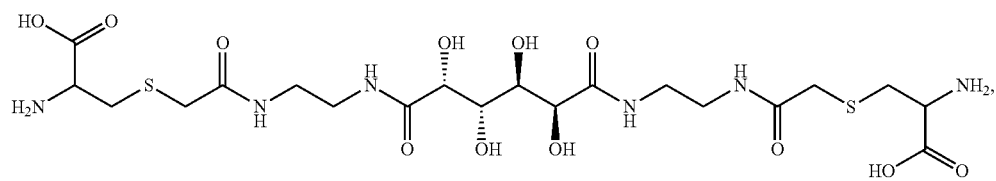

X

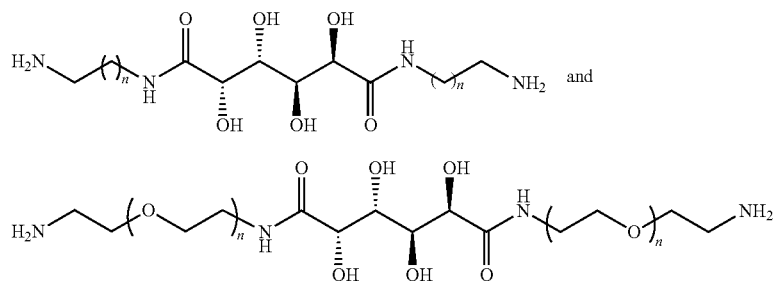 and

XI

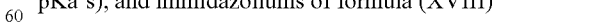

In particular one or more cationic or anionic moieties (B) for use with anionic cargo and cationic cargos respectively can independently have a general formula of:

(XII)

$R_5$ ── Organic group ── $R_5$ wherein $R_5$ is an electrophilic group that can be covalently linked to A when A contains nucleophilic groups. Examples of $R_5$ in this case include but are not limited to —C(=O)OH, —C(=O)Cl, —C(=O)NHS, —C(=$NH_2^+$)OMe, —S(=O)OCl—, —$CH_2$Br, alkyl and aromatic esters, terminal alkynes, tosylate, and mesylate amongst several others. In the case where moiety A contains electrophilic end groups, $R_5$ will bear nucleophilic groups such as —$NH_2$ (primary amines), —OH, —SH, $N_3$ and secondary amines.

In particular, when moiety (B) is a cationic moiety (B) for use with anionic cargo the "organic group" is an organic moiety that can have a backbone with a general formula consisting of $C_mH_{2m}$ with m≥1 and other heteroatoms and must contain at least one of the following functional groups including amidines of formula (XIII), quartenary ammoniums of formula (XIV), primary amine group of formula (XV), secondary amine group of formula (XVI), tertiary amine groups of formula (XVII) (protonated below their pKa's), and immidazoliums of formula (XVIII)

(XIII)

In several embodiments, (B) can be formed by any straight, branched, symmetric or asymmetric compound linking the two (A) moieties through functional groups.

In several embodiments, (B) can be formed by a compound where at least two cross-linkable groups linking the two (A) moieties.

In some embodiments, (B) contains a neutral, cationic or anionic organic group whose nature and composition is dependent on the chemical nature of the compound to be covalently or non-covalently tethered Exemplary cationic moieties of (B) for use with anionic cargo include, but are not limited to, organic groups bearing amidines groups, quartenary ammoniums, primary amine group, secondary amine group, tertiary amine groups (protonated below their pKa's), and immidazoliums Exemplary anionic moieties contained in (B) for use with cationic cargo include, but are not limited to, organic groups bearing sulfonates of formula, nitrates of formula, carboxylates of formula, and phosphonates -continued

(XIV)

(XV)

(XVI)

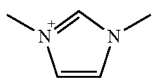
(XVII)

(XVIII)

In embodiments, when moiety (B) is an anionic moiety (B) for use with cationic cargo, the "organic group" may have a backbone with a general formula consisting of $C_mH_{2m}$ with $m \geq 1$ and other heteroatoms and must contain at least one of the following functional groups including sulfonates of formula (XIX), nitrates of formula (XX), carboxylates of formula (XXI), and phosphonates of formula (XXII)

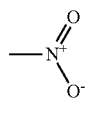
(XIX)

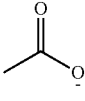
(XX)

(XXI)

(XXII)

In embodiments wherein (B) is comprised by carboxylates (XXI), a compound containing primary amine or hydroxyl groups can also be attached via the formation of a peptide or an ester bond.

In embodiments wherein (B) is comprised of primary amine group of formula (XV), and/or secondary amine group of formula (XVI), a compound containing carboxylic acid groups can also be attached via the formation of a peptide bond.

In several embodiments moiety (B) can independently be selected from

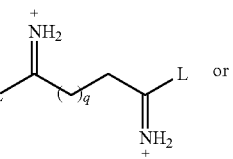
(XXIII)

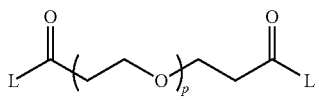
(XXIV)

in which q is from 1 to 20; and in particular can be 5 p is from 20 to 200; and

L is a leaving group.

The term "leaving group" as used herein indicates a molecular fragment that departs with a pair of electrons in heterolytic bond cleavage. In particular, a leaving group can be anions or neutral molecules, and the ability of a leaving group to depart is correlated with the $pk_a$, of the conjugate acid, with lower $pk_a$, being associated with better leaving group ability. Exemplary anionic leaving groups include halides such as $Cl^-$, $Br^-$, and $I^-$, and sulfonate esters, such as para-toluenesulfonate or "tosylate" ($TsO^-$). Exemplary neutral molecule leaving groups are water ($H_2O$), ammonia ($NH_3$), and alcohols (ROH).

In particular, in several embodiments, L can be a chloride (Cl), methoxy (OMe), t butoxy (OtBU) or N hydrosuccinimide (NHS).

In some embodiments the structural unit of formula (I) can have formula

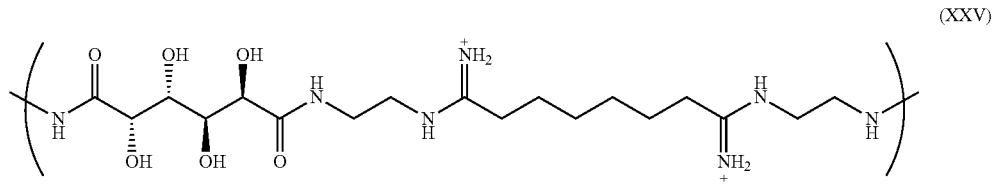
(XXV)

In some embodiments the structural unit of formula (II) can have formula (XXVI)

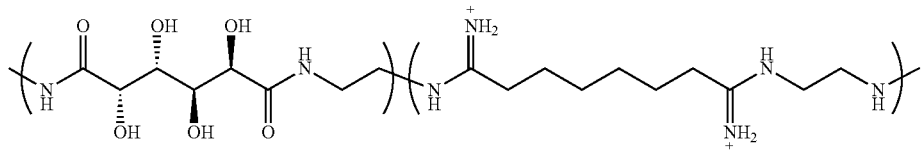

In some embodiments the structural unit of formula (III) can have formula (XXVII)

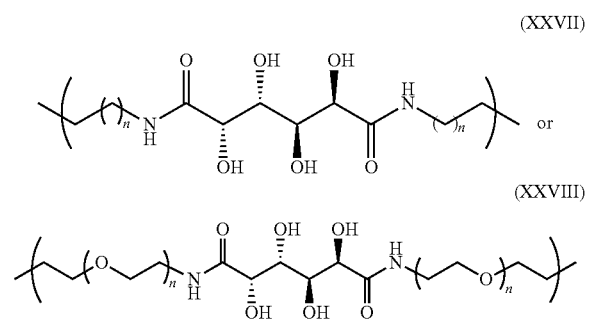

in which
n is from 1 to 20 and in particular from 1 to 4.

In some embodiments, the polymer containing polyol can have the formula (XXIX)

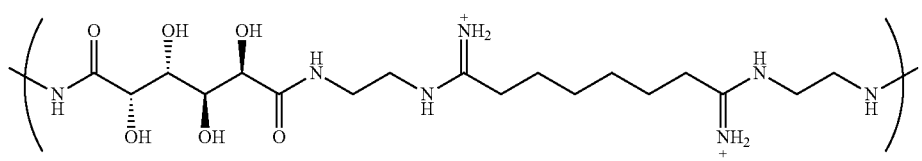

In some embodiments, the polymer containing a boronic acid contains at least one terminal boronic acid group and has the following structure:

(XXX)

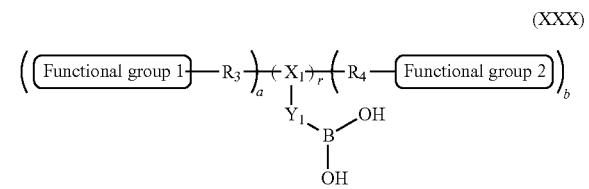

wherein
$R_3$ and $R_4$ can be independently selected from any hydrophilic organic polymer, and in particular can independently be any poly(ethylene oxides), and zwitterionic polymers.

$X_1$ can be an organic moiety containing one or more of —CH, —N, or —B $Y_1$ can be an alkyl group with a formula —$C_mH_{2m}$— with m≥1, possibly containing olefins or alkynyl groups, or an aromatic group such as a phenyl, biphenyl, napthyl or anthracenyl r is from 1 to 1000,
a is from 0 to 3, and
b is from 0 to 3 and wherein functional group 1 and functional group 2 are the same or different and are able to bind to a targeting ligand, and in particular a protein, antibody or peptide, or is an end group such as —OH, —OCH$_3$ or —(X$_1$)—(Y$_1$)—B(OH)$_2$—

In some embodiments, $R_3$ and $R_4$ are (CH$_2$CH$_2$O)$_t$, where t is from 2 to 2000 and in particular from 100 to 300

In some embodiments $X_1$ can be —NH—C(=O)—, —S—S—, —C(=O)—NH—, —O—C(=O)— or —C(=O)—O— and/or $Y_1$ can be a phenyl group.

In some embodiments r can be 1, a can be 0 and b can be 1.

In some embodiments, functional group 1 and functional group 2 are the same or different and are independently selected from. —B(OH)$_2$, —OCH$_3$, —OH.

In particular, functional group 1 and/or 2 of formula (XXXI) can be a functional group able to bind a cargo and in particular a targeting ligand such as a protein, antibody or peptide, or can be an end group such as —OH, —OCH$_3$ or —(X)—(Y)—B(OH)$_2$.

The term "functional group" as used herein indicates specific groups of atoms within a molecular structure or portion thereof that are responsible for the characteristic chemical reactions of that structure or portion thereof. Exemplary functional groups include hydrocarbons, groups containing halogen, groups containing oxygen, groups containing nitrogen and groups containing phosphorus and sulfur all identifiable by a skilled person. In particular, functional groups in the sense of the present disclosure include a carboxylic acid, amine, triarylphosphine, azide, acetylene, sulfonyl azide, thio acid and aldehyde. In particular, for example, a functional group able to bind a corresponding functional group in a targeting ligand can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react to another functional group. Thus, functional groups that can react with each other can be referred to as corresponding functional groups.

An end-group indicates a constitutional unit that is an extremity of a macromolecule or oligomer molecule. For example the end-group of a PET polyester may be an alcohol group or a carboxylic acid group. End groups can be used to determine molar mass. Exemplary end groups comprise —OH. —COOH, $NH_2$, and $OCH_3$, In some embodiments, the polymer containing boronic acid can have formula

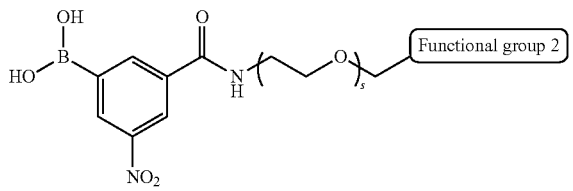

(XXXI)

wherein s is from 20 to 300.

Exemplary agents and targeting ligands that can be attached to nanoparticles of the present disclosure comprise organic or inorganic molecules, including polynucleotides, nucleotides, aptamers polypeptides, proteins, polysaccharides macromolecular complexes including but not limited to those comprising a mixture of protein and polynucleotides, saccharides and/or polysaccharides, viruses, molecules with radioisotopes, antibodies or antibody fragments.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide."

The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene.

The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer, peptide or oligopeptide. In particular, the terms "peptide" and "oligopeptide" usually indicate a polypeptide with less than 50 amino acid monomers. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived. All of these amino acids can be synthetically incorporated into a peptide or polypeptide using standard amino acid coupling chemistries. The term "polypeptide" as used herein includes polymers comprising one or more monomer, or building blocks other than an amino acid monomer. The terms monomer, subunit, or building blocks indicate chemical compounds that under appropriate conditions can become chemically bonded to another monomer of the same or different chemical nature to form a polymer. The term "polypeptide" is further intended to comprise a polymer wherein one or more of the building blocks is covalently bound to another by a chemical bond other than amide or peptide bond.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules. Exemplary proteins herein described are antibodies.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope". In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

Figure 2:
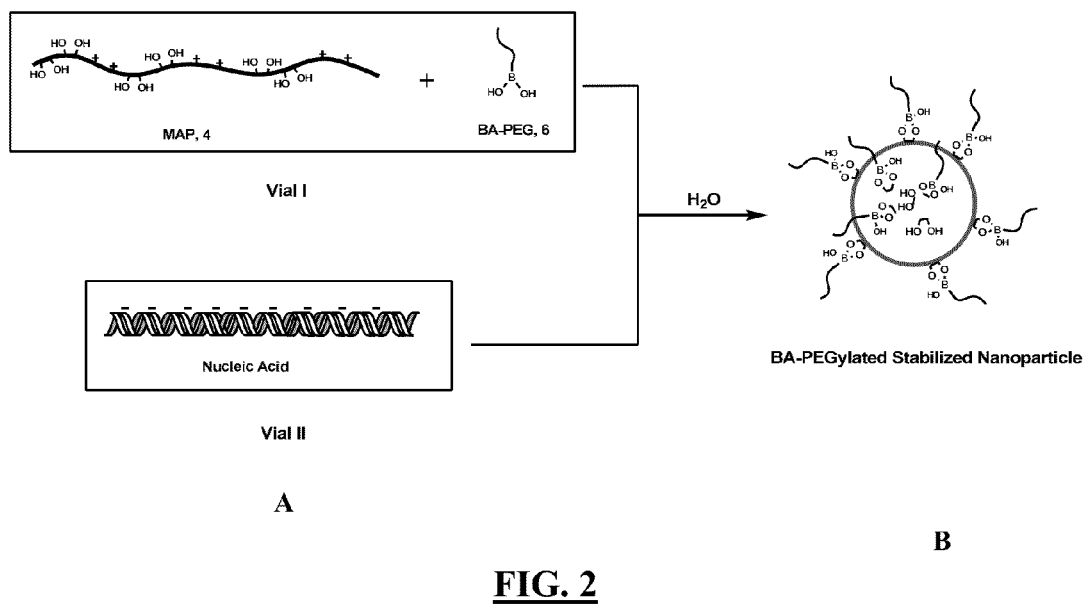
FIG. 2 shows a schematic representation of a nanoparticle and a related method of manufacturing according to an embodiment of the present disclosure. Panel A shows a polymer containing a polyol (MAP, 4) and a polymer containing a boronic acid (BA-PEG, 6) together with a molecule of interest (nucleic acid) according to an embodiment of the present disclosure. Panel B shows a BA-pegylated stabilized nanoparticle formed upon assembly of the polymers and compound shown in panel A.

In several embodiments, polyol polymers form a non-covalent complex or linkage with one or more compounds of interest to be delivered according to the schematic illustration of FIGS. 1 and 2.

In several embodiments, a nanoparticle structure comprises an agent and a polymer containing a polyol, where the agent is linked to a polyol polymer by a covalent bond. An example of a polyol polymer conjugated to an agent is detailed in Examples 16-21. In these embodiments, polyol polymers conjugated to an agent (herein referred to as "polyol polymer-agent conjugate") form nanoparticles whose structure presents sites on their surface for interaction with BA molecules.

In several of those embodiments, the nanoparticle further comprises BA polymers configured to provide steric stabilization and/or targeting functionality to the nanoparticle. In particular, in those embodiments the addition of a BA polymer allows minimizing of self-aggregation and undesired interactions with other nanoparticles, thus providing enhanced salt and serum stability. For example, steric stabilization is herein provided by the BA polymer having PEG as illustrated by the exemplary nanoparticle described in Example 12.

In such embodiments, the structure of this nanoparticle affords several advantages over agents delivery methods of the prior art, such as the ability to provide controlled release of one or more agents. This feature can be provided, for example, by the use of a biodegradable ester linkage between the agent and the polyol polymer. A person skilled in the art will recognize other potential linkages suitable for this purpose. In these embodiments, another advantage is the ability to provide specific targeting of the agent through the BA polymer moiety.

In several embodiments, BA polymers may comprise a fluorinated boronic acid (Example 7) or a fluorinated cleavable boronic acid (Example 8) capable of being used as an imaging agent in MRI or other similar techniques. Such an imaging agent may be useful for tracking the pharmacokinetics or pharmacodynamics of an agent delivered by the nanoparticle.

In several embodiments, a nanoparticle structure comprises an agent and a polyol polymer, where the nanoparticle is a modified liposome. In these embodiments, the modified liposome comprises lipids conjugated to polyol polymers via a covalent linkage such that the surface of the liposome presents polyol polymers. In these embodiments, the modified liposomes form such that the agents to be delivered are contained within the liposome nanoparticle.

The term "liposome" as used herein indicates a vesicular structure comprised of lipids. The lipids typically have a tail group comprising a long hydrocarbon chain and a hydrophilic head group. The lipids are arranged to form a lipid bilayer with an inner aqueous environment suitable to contain an agent to be delivered. Such liposomes present an outer surface that may comprise suitable targeting ligands or molecules for specific recognition by cell surface receptors or other targets of interest.

The term "conjugated" as used herein indicates that one molecule has formed a covalent bond with a second molecule and includes linkages where atoms covalently bond with alternating single and multiple (e.g. double) bonds (e.g., C═C—C═C—C) and influence each other to produce electron delocalization.

In yet other embodiments of the present disclosure, a nanoparticle structure comprises an agent and a polyol, where the nanoparticle is a modified micelle. In these embodiments, the modified micelle comprises polyol polymers modified to contain a hydrophobic polymer block.

The term "hydrophobic polymer block" as used in the present disclosure indicates a segment of the polymer that on its own would be hydrophobic.

The term "micelle" as used herein refers to an aggregate of molecules dispersed in a liquid. A typical micelle in aqueous solution forms an aggregate with the hydrophilic "head" regions in contact with surrounding solvent, sequestering the hydrophobic single tail regions in the micelle centre. In the present disclosure the head region may be, for example, a surface region of the polyol polymer while the tail region may be, for example, the hydrophobic polymer block region of the polyol polymer.

In these embodiments, polyol polymers with a hydrophobic polymer block, when mixed with an agent to be delivered, arrange to form a nanoparticle that is a modified micelle with agents to be delivered contained within the nanoparticle. Such nanoparticle embodiments present polyol polymers on their surface that are suitable to interact with BA polymers that do or do not have targeting functionality according to previous embodiments. In these embodiments, BA polymers capable of use for this purpose include those with hydrophilic A and hydrophobic B in formula (I) or (II). This interaction provides the same or similar advantages as it does for other nanoparticle embodiments mentioned above.

In some embodiments, nanoparticles or related components can be comprised in a composition together with an acceptable vehicle. The term "vehicle" as used herein indicates any of various media acting usually as solvents, carriers, binders, excipients or diluents for a nanoparticle comprised in the composition as an active ingredient.

In some embodiments, where the composition is to be administered to an individual the composition can be a pharmaceutical composition and the acceptable vehicle can be a pharmaceutically acceptable vehicle.

In some embodiments, a nanoparticle can be included in pharmaceutical compositions together with an excipient or diluent. In particular, in some embodiments, pharmaceutical compositions are disclosed which contain nanoparticle, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the nanoparticle. Suitable excipients also include any substance that can be used to bulk up formulations with nanoparticles to allow for convenient and accurate dosage. In addition to their use in the single-dosage quantity, excipients can be used in the manufacturing process to aid in the handling of nanoparticles. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration.

Exemplary compositions for parenteral administration include but are not limited to sterile aqueous solutions, injectable solutions or suspensions including nanoparticles. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection.

In several embodiments nanoparticles herein described are delivered to a predetermined target. In some embodiments, the target is an in vitro biological system and the method comprises contacting target with the nanoparticle herein described.

In some embodiments, a method is provided for delivery of an agent to an individual where the method comprises formulating a suitable nanoparticle according to various disclosed embodiments. The nanoparticles may also be formulated into a pharmaceutically acceptable composition according to several disclosed embodiments. The method further comprises delivering a nanoparticle to a subject. To deliver the nanoparticle to an individual, the nanoparticle or nanoparticle formulations may be given orally, parenterally, topically, or rectally. They are delivered in forms suitable for each administration route. For example, nanoparticle compositions can be administered in tablets or capsule form, by injection, inhalation, eye lotion, ointment, suppository, infusion; topically by lotion or ointment; and rectally by suppositories.

The term "individual" as used herein includes a single biological organism including but not limited to plants or animals and in particular higher animals and in particular vertebrates such as mammals and in particular human beings.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal, injection and infusion.

The phrases "systemic administration," "administered systemically," "peripheral administration" and "administered peripherally" as used herein mean the administration of a nanoparticle or composition thereof other than directly into the central nervous system, such that it enters the individual's system and, thus, is subject to metabolism and other like processes, for example, subcutaneous administration.

Actual dosage levels of the active ingredient or agent in the pharmaceutical compositions herein described may be varied so as to obtain an amount of the active ingredient which is effective to achieve the desired therapeutic response for a particular individual, composition, and mode of administration, without being toxic to the individual.

These therapeutic polymer conjugate may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the therapeutic polymer conjugate, which may be used in a suitable hydrated fonn, and/or the pharmaceutical compositions of the present invention, are formulated into pharmaceutically acceptable dosage forms by conventional methods known to those of skill in the art.

In particular in some embodiments, the compound delivered is a drug for treating or preventing a condition in the individual.

The term "drug" or "therapeutic agent" indicates an active agent that can be used in the treatment, prevention, or diagnosis of a condition in the individual or used to otherwise enhance the individual's physical or mental well-being.

The term "condition" as used herein indicates a usually the physical status of the body of an individual, as a whole or of one or more of its parts, that does not conform to a physical status of the individual, as a whole or of one or more of its parts, that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The term "treatment" as used herein indicates any activity that is part of a medical care for or deals with a condition medically or surgically.

The term "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

Exemplary compounds that can be delivered by the nanoparticles herein described and that are suitable as drugs comprise compounds able to emit electromagnetic radiations (such as $^{10}B$ isotopes) to be used in radiation treatments (such as boron neutron capture) Additional therapeutic agents comprise any lipophilic or hydrophilic, synthetic or naturally occurring biologically active therapeutic agent including those known in the art. The Merck Index, An Encyclopedia of Chemicals, Drugs, and Biologicals, 13th Edition, 2001, Merck and Co., Inc., Whitehouse Station, N.J. Examples of such therapeutic agents include, but are not limited to, small molecule pharmaceuticals, antibiotics, steroids, polynucleotides (e.g. genomic DNA, cDNA, mRNA, siRNA, shRNA, miRNA, antisense oligonucleotides, viruses, and chimeric polynucleotides), plasmids, peptides, peptide fragments, small molecules (e.g. doxorubicin), chelating agents (e.g. deferoxamine (DESFERAL), ethylenediaminetetraacetic acid (EDTA)), natural products (e.g. Taxol, Amphotericin), and other biologically active macromolecules such as, for example, proteins and enzymes. See also U.S. Pat. No. 6,048,736 which lists active agents (therapeutic agents) that can be used as therapeutic agent with nanoparticles herein described. Small molecule therapeutic agents may not only be the therapeutic agent within the composite particle but, in an additional embodiment, may be covalently bound to a polymer in the composite. In several embodiments, the covalent bond is reversible (e.g. through a prodrug form or biodegradable linkage such as a disulfide) and provides another way of delivering the therapeutic agent. In several embodiments therapeutic agent that can be delivered with the nanoparticles herein described include chemotherapeutics such as epothilones, camptothecin-based drugs, taxol, or a nucleic acid such as a plasmid, siRNA, shRNA, miRNA, antisense oligonucleotides aptamers or their combination, and additional drugs identifiable by a skilled person upon reading of the present disclosure.

In some embodiments, the compound delivered is a compound suitable for imaging a cell or tissue of the individual. Exemplary compounds that can be delivered by the nanoparticles herein described and that are suitable for imaging comprise compounds that contain isotopes such as $^{19}F$ isotopes for MR imaging, $^{18}F$ or $^{64}Cu$ for PET imaging etc.

In particular, the nanoparticles described herein can be configured to contain $^{19}F$-containing BA polymers. For example, $^{19}F$ atoms can be incorporated into a non-cleavable or cleavable BA polymer compound. Other locations for the $^{19}F$ atoms are possible on the BA polymer component, the polyol polymer component, or on the agent to be delivered. These and other variations will be apparent to one skilled in the art.

In several embodiments, the nanoparticles herein described can be used to deliver chemicals used in the agricultural industry. In another embodiment of the invention, the agent delivered by the nanoparticle herein described is a biologically active compound having microbiocidal and agricultural utility. These biologically active compounds include those known in the art. For example, suitable agriculturally biologically active compounds include, but are not limited to, fertilizers, fungicides, herbicides, insecticides, and mildewcides. Microbicides are also used in water-treatment to treat municipal water supplies and industrial water systems such as cooling waters, white water systems in papermaking Aqueous systems susceptible to microbiological attack or degradation are also found in the leather industry, the textile industry, and the coating or paint industry. Examples of such microbicides and their uses are described, individually and in combinations, in U.S. Pat. Nos. 5,693,631, 6,034,081, and 6,060,466, which are incorporated herein by reference. Compositions containing active agents such as those discussed above may be used in the same manner as known for the active ingredient itself. Notably, because such uses are not pharmacological uses, the polymer of the composite does not necessarily have to meet the toxicity profile required in pharmaceutical uses.

In certain embodiments, nanoparticles comprising polyol polymers and BA polymers can also be comprised in a system suitable for delivering any of the compounds herein indicated and in particular agents, using a nanoparticle. In some embodiments of the system, nanoparticles are provided with components suitable for preparing the nanoparticles for administration to an individual.

The systems herein disclosed can be provided in the form of kits of parts. For example the polyol polymers and/or BA polymers can be included as a molecule alone or in the presence of suitable excipients, vehicles or diluents.

In a kit of parts, polyol polymers, BA polymers, and/or agents to be delivered are comprised in the kit independently possibly included in a composition together with suitable vehicle carrier or auxiliary agents. For example, polyol polymers and/or BA polymers can be included in one or more compositions alone and/or included in a suitable vector. Also, an agent to be delivered can be included in a composition together with a suitable vehicle carrier or auxiliary agent. Alternatively, the agent may be supplied by the end user and may be absent from the kit of parts. Furthermore, the polyol polymers, BA polymers and/or agents can be included in various forms suitable for appropriate incorporation into a nanoparticle.

Additional components can also be included and comprise microfluidic chip, reference standards, buffers, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (such as wash buffers and the like).

Further details concerning the identification of the suitable carrier agent or auxiliary agent of the compositions, and generally manufacturing and packaging of the kit, can be identified by the person skilled in the art upon reading of the present disclosure.

In some embodiments, a nanoparticle may be prepared by preparing the individual components of the nanoparticle followed by mixing the components in various orders to arrive at a desired composite nanoparticle structure. Preparation and mixing of components is carried out in suitable solutions known by those skilled in the art.

The term "mixing" as used herein indicates addition of one solution comprising a molecule of interest with another solution comprising another molecule of interest. For example, an aqueous solution of polyol polymers may be mixed with an aqueous solution of BA polymers in the context of the present disclosure.

The term "solution" as used herein indicates any liquid phase sample containing molecules of interest. For example, an aqueous solution of polyol polymers may comprise polyol polymers diluted in water or any buffered solution, in particular aqueous solutions.

In some embodiments, a nanoparticle can be prepared by mixing polyol polymers with an agent to be delivered (FIGS. 1 and 2), forming a polyol polymer-agent nanoparticle. In other embodiments, a nanoparticle may be prepared by further mixing BA polymers with the polyol polymer-agent nanoparticle. In other embodiments, a nanoparticle is prepared by mixing polyol polymers with BA polymers, followed by mixing an agent to be delivered. In yet other embodiments, a nanoparticle is prepared by simultaneously mixing polyol polymers, BA polymers, and an agent to be delivered.

In some embodiments, a nanoparticle is prepared by forming a polyol polymer-agent conjugate according to various embodiments of the present disclosure, thus preparing a nanoparticle comprised of a polyol polymer-agent conjugate. In other embodiments nanoparticles comprised of a polyol polymer-agent conjugates may be prepared by dissolving the nanoparticles in a suitable aqueous solution. In yet further embodiments, nanoparticles comprised of a polyol polymer-agent conjugates may be prepared by mixing polyol polymer-agent conjugates with BA polymers that do or do not provide targeting ligand.

In some embodiments, a nanoparticle can be prepared by mixing polyol polymers with a hydrophobic polymer block with an agent to be delivered, thus preparing a modified micelle according to embodiments of the present disclosure. In other embodiments, a nanoparticle may be prepared by further mixing the modified micelle with BA polymers. In yet other embodiments, a nanoparticle may be prepared by mixing polyol polymers with BA polymers, followed by mixing an agent to be delivered, thus preparing a nanoparticle that is a modified micelle.

In some embodiments of the present disclosure, a nanoparticle can be prepared by mixing lipids conjugated with polyol polymers with BA polymers and/or agents to be delivered, thus preparing a modified liposome. In various embodiments, a nanoparticle may be prepared by mixing lipids conjugated with polyol polymers with BA polymers, followed by mixing agents to be delivered. In other embodiments, a nanoparticle may be prepared by mixing lipids conjugated with polyol polymers with agents to be delivered. In other embodiments, a nanoparticle may be prepared by mixing lipids conjugated with polyol polymers with agents to be delivered, followed by mixing BA polymers, thus preparing a nanoparticle that is a modified liposome.

The formation of nanoparticles according to several embodiments of the present disclosure can be analyzed with techniques and procedures known by those with skill in the art. For example, in several embodiments, gel retardation assays are used to monitor and measure the incorporation of a nucleic acid agent within a nanoparticle (Example 10). In several embodiments, a suitable nanoparticle size and/or zeta potential can be chosen using known methods (Example 11).

Further details concerning the identification of the suitable carrier agent or auxiliary agent of the compositions, and generally manufacturing and packaging of the kit, can be identified by the person skilled in the art upon reading of the present disclosure.

Nanoparticles Having a Polymer with Nitrophenylboronic Acid

Described herein are nanoparticles having a polymer containing a polyol that is conjugated to a polymer containing a nitrophenylboronic acid. The polymer containing a polyol nanoparticle segment of the targeted nanoparticles described can have one or more of any one of the following structural units:

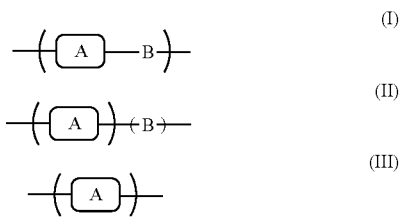

where A is an organic moiety of formula

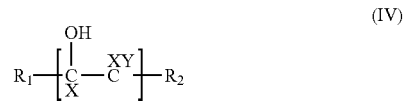

in which $R_1$ and $R_2$ are independently selected from any carbon-based or organic group with a molecular weight of about 10 kDa or less; X is independently selected from an aliphatic group containing one or more of —H, —F, —C, —N or —O; and Y is independently selected from —OH or an organic moiety presenting an —OH, and B is an organic moiety linking one of the $R_1$ and $R_2$ of a first moiety A with one of the $R_1$ and $R_2$ of a second moiety A in the polymer. In some embodiments X can be $C_nH_{2n+1}$, in which n is any single number from 0-5 and Y is —OH. In some embodiments A can be any one of:

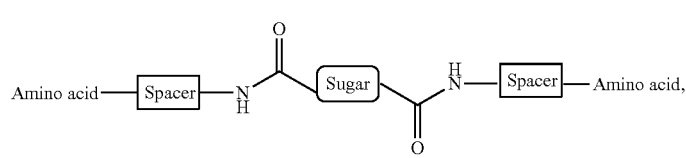

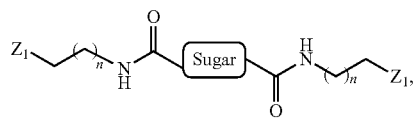

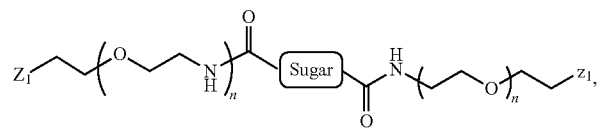

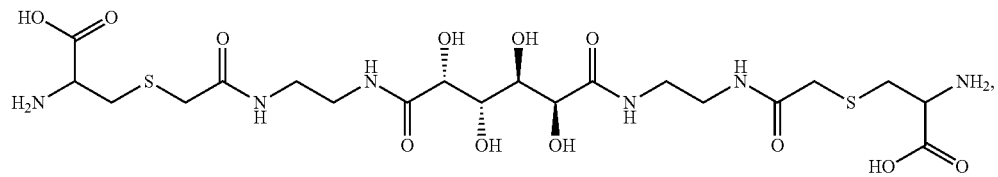

-continued

X

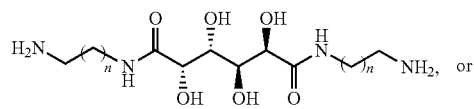

XI

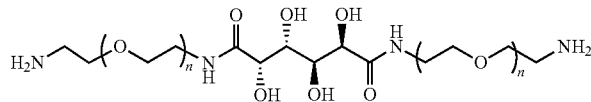

where the spacer is independently selected from any organic group; the amino acid is selected from any organic group bearing a free amine and a free carboxylic acid group; n is any single number from 1 to 20; and $Z_1$ is independently selected from —$NH_2$, —OH, —SH, and —COOH; $R_1$ and $R_2$ independently can have the formula:

(V)

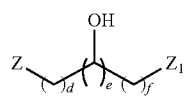

wherein d is any single number from 0 to 100, e is any single number from 0 to 100, f is any single number from 0 to 100, Z is a covalent bond linking one organic moiety to another, and $Z_1$ is independently selected from —$NH_2$, —OH, —SH, and —COOH; B can be any one of (XXIII)

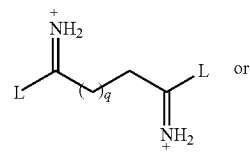

or (XIV)

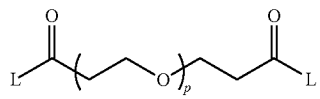

in which q is any single number from 1-20; p is any single number from 20-200; and L is a leaving group, where these B subunits are paired with any one of the A subunits described above. In more particular embodiments, the polymer containing a polyol nanoparticle segment of the targeted nanoparticles shown in structural unit of formula (I) can be:

(XXV)

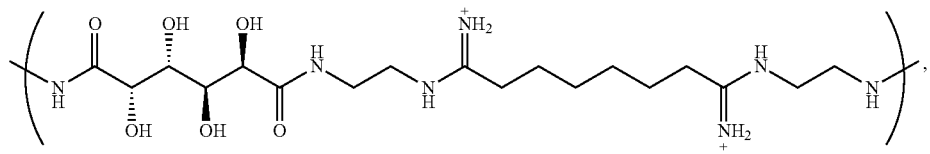

the polymer containing a polyol nanoparticle segment of the targeted nanoparticles shown instructural unit of formula (II) can be:

(XXVI)

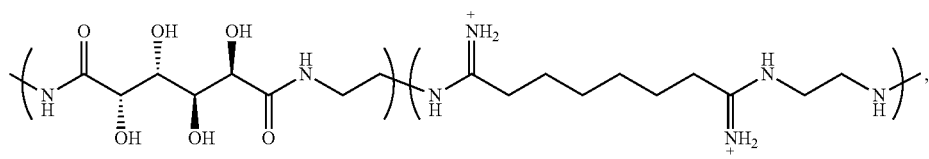

and the polymer containing a polyol nanoparticle segment of the targeted nanoparticles shown in structural unit of formula (III) can be:

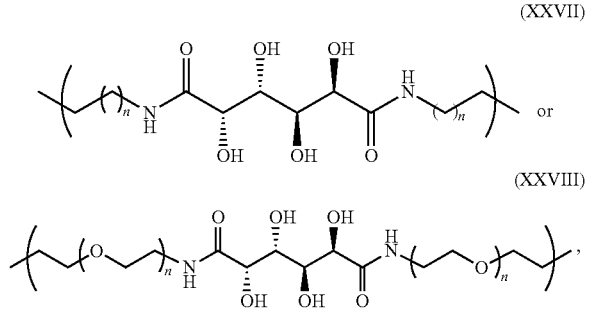

(XXVII)

(XXVIII)

in which n is any single number from 1-20. In some embodiments of the described targeted nanoparticle, the polymer containing a polyol is:

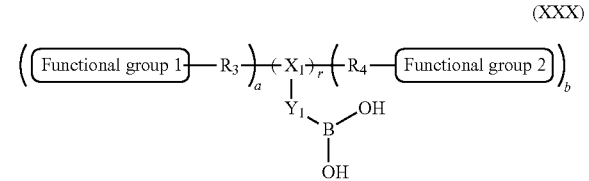

In summary, any one of the formulas for subpart A (formula VI, VII, or VIII) can be combined with any one of the formulas for subpart B (formula XXIII or XIV) to form the polymer containing a polyol of the described nanoparticles. In certain aspects described herein the nanoparticles can have a polymer containing a polyol formed from the combination of anyone of the formulas for subpart A (IX, X, or XI) with any one of the formulas for subpart B (formula XXIII or XIV).

In some embodiments the polymer containing a nitrophenylboronic acid comprises a nitrophenylboronic acid group and has the general formula:

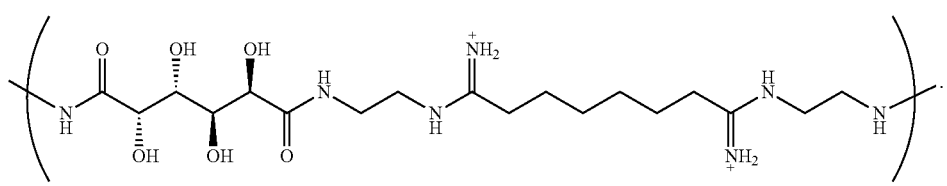

(XXX)

where $R_3$ and $R_4$ are independently an hydrophilic organic polymer, $X_1$ is an organic moiety containing one or more of —C, —N, or —B, $Y_1$ is an alkyl group of formula —$C_mH_{2m}$—, in which m is ≥1 or an aromatic group, r is any single number from 1-1000, a is any single number from 0-3, and b is any single number from 0-3 and functional group 1 and functional group 2 may be the same or different and may independently comprise —$B(OH)_2$, —$OCH_3$, —($X_1$)—($Y_1$)—$B(OH)_2$, —COOH, —$NH_2$, or —OH. In some embodiments these variable subparts of the described polymer containing a nitrophenylboronic acid can be selected from the following: $R_3$ and $R_4$ may be $(CH_2CH_2O)_t$, where t is any single number from 2 to 2000; $X_1$ is any one of —NH—C(=O)—, —S—S—, —C(=O)—NH—, —O—C(=O)— or —C(=O)—O— and $Y_1$ is a nitrophenyl group. In some embodiments these variable subparts of the described polymer containing a nitrophenylboronic acid can be selected from the following: $R_3$ and $R_4$ may be $(CH_2CH_2O)_t$, where t is any single number from 2 to 2000; $X_1$ is any one of —NH—C(=O)—, —S—S—, —C(=O)—NH—, —O—C(=O)— or =C(=O)—O— and $Y_1$ is a nitrophenyl group, and r can have a value of 1, a can have a value of 0 and b can have a value of 1. In each of the embodiments of the polymer containing a nitrophenylboronic acid, the nitro group can be at either the ortho, meta, or para position, relative to the boronic acid group, of the phenyl ring. In still further embodiments, the polymer containing a nitrophenylboronic acid can have additional groups present on the phenyl ring, such as a methyl group. In a particular embodiment the targeted nanoparticle of described herein can include a polymer containing a nitrophenylboronic acid having any one of the following formulas:

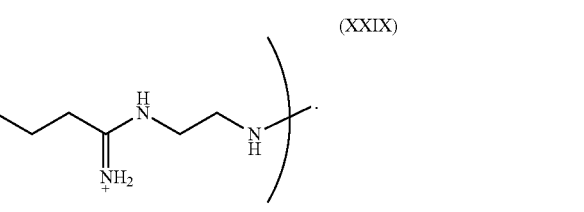

(XXXIII)

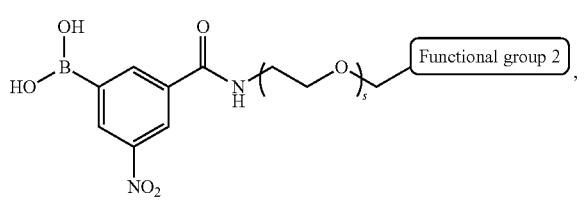

(XXXIV)

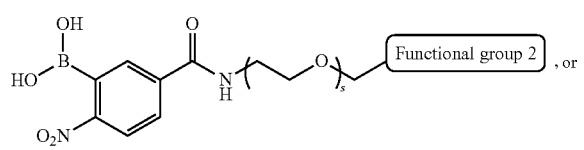

(XXXV)

where s is any single number from 20-300. The polymers of formulas XXXIII, XXXIV, and XXXV can be further modified to change the position of the PEG on the phenyl ring to be in the ortho, meta, or para position relative to the boronic acid group.

In summary, any one of the formulas for subpart A (formula VI, VII, or VIII) can be combined with any one of the formulas for subpart B (formula XXIII or XIV) to form the polymer containing a polyol nanoparticle segment of the described nanoparticles, the resulting polymer containing a polyol can then be coupled to a polymer containing a nitrophenylboronic acid. In some embodiments the conjugation between the described polymer containing a polyol and the described polymer containing a nitrophenylboronic acid will be mediated by at least one hydroxyl group of the boronic acid group. In certain aspects described herein the nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid having formula XXX. In some embodiments described herein, the nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid corresponding to any one of formula XXXIII, XXXIV, or XXXV.

The nanoparticles described herein can further include a compound. In some embodiments the compound can be one or more therapeutic agents, such as a small molecule chemotherapeutic agent or a polynucleotide. In some embodiments the polynucleotide can be any one or more of DNA, RNA, or interfering RNA (such as shRNA, siRNA or miRNA). In some embodiments the small molecule chemotherapeutic agent can be one or more of camptothecin, an epothilone, or a taxane. The nanoparticles described herein can also include a combination of one or more polynucleotides with one or more small molecule chemotherapeutic agents. In this regard, any one of the polymer of subpart A (formula VI, VII, or VIII) can be combined with any one of the polymer of subpart B (formula XXIII or XIV) to form the polymer containing a polyol nanoparticle segment of the described nanoparticles, the resulting polymer containing a polyol can then be coupled to a polymer containing a nitrophenylboronic acid and the polymer of subpart A, subpart B, or the polymer having nitrophenylboronic acid can be formed with one or more therapeutic agents, such as a small molecule chemotherapeutic agent or a polynucleotide. In some embodiments the polymer of subpart A (formula VI, VII, or VIII) can be combined with any one of the polymer of subpart B (formula XXIII or XIV) to form the polymer containing a polyol nanoparticle segment of the described nanoparticles, the resulting polymer containing a polyol can then be coupled to a polymer containing a nitrophenylboronic acid and the polymer of subpart A, subpart B, or the polymer having nitrophenylboronic acid can be formed with one or more of DNA, RNA, or interfering RNA (such as shRNA, siRNA or miRNA). In some embodiments the polymer of subpart A (formula VI, VII, or VIII) can be combined with any one of the polymer of subpart B (formula XXIII or XIV) to form the polymer containing a polyol nanoparticle segment of the described nanoparticles, the resulting polymer containing a polyol can then be coupled to a polymer containing a nitrophenylboronic acid and the polymer of subpart A, subpart B, or the polymer having nitrophenylboronic acid can be formed with one or more chemotherapeutic agents. In some embodiments the polymer of subpart A (formula VI, VII, or VIII) can be combined with any one of the polymer of subpart B (formula XXIII or XIV) to form the polymer containing a polyol nanoparticle segment of the described nanoparticles, the resulting polymer containing a polyol can then be coupled to a polymer containing a nitrophenylboronic acid and the polymer of subpart A, subpart B, or the polymer having nitrophenylboronic acid can be formed with one or more of DNA, RNA, or interfering RNA (such as shRNA, siRNA or miRNA). In some embodiments the conjugation between the described polymer containing a polyol and the described polymer containing a nitrophenylboronic acid will be mediated by at least one hydroxyl group of the nitrophenylboronic acid group. In some embodiments described herein, the targeted nanoparticles incorporating a therapeutic agent or polynucleotide can have a polymer containing a polyol formed from the combination of anyone of the formulas for subpart A (IX, X, or XI) with any one of the formulas for subpart B (formula XXIII or XIV), which can then be coupled to a polymer containing a nitrophenylboronic acid corresponding to any one of formula XXXIII, XXXIV, or XXXV.

Targeted Nanoparticles

Described herein are targeted nanoparticles having a polymer containing a polyol that is conjugated to any of 5, 4, 3, 2, or 1 targeting ligands. The polymer containing a polyol nanoparticle segment of the targeted nanoparticles described can have one or more of any one of the following structural units:

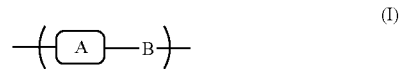

(I)

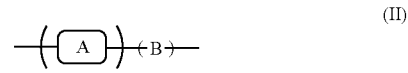

(II)

(III)

where A is an organic moiety of formula

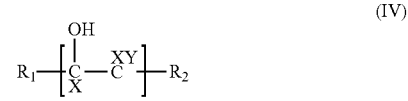

(IV)

in which $R_1$ and $R_2$ are independently selected from any carbon-based or organic group with a molecular weight of about 10 kDa or less; X is independently selected from an aliphatic group containing one or more of —H, —F, —C, —N or —O; and Y is independently selected from —OH or an organic moiety presenting an —OH, and B is an organic moiety linking one of the $R_1$ and $R_2$ of a first moiety A with one of the $R_1$ and $R_2$ of a second moiety A in the polymer. In some embodiments X can be $C_nH_{2n+1}$, in which n is any single number from 0-5 and Y is —OH. In some embodiments A can be any one of:

VI

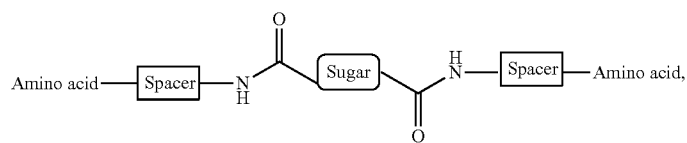

VII

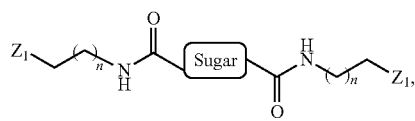

VIII

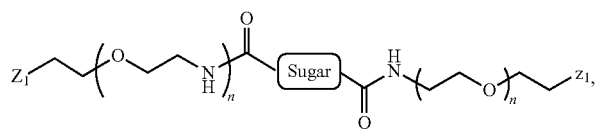

IX

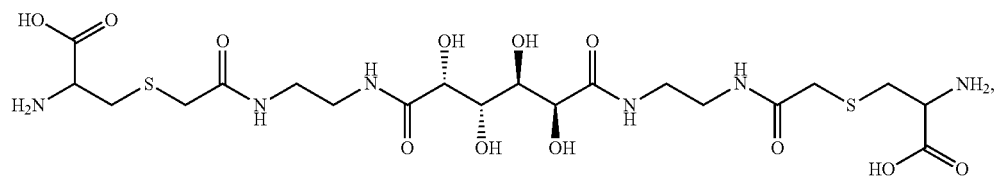

X

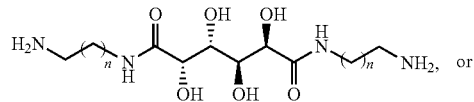

XI

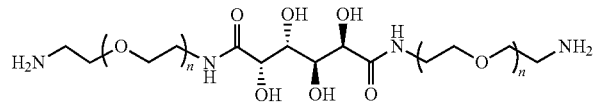

where the spacer is independently selected from any organic group; the amino acid is selected from any organic group bearing a free amine and a free carboxylic acid group; n is any single number from 1 to 20; and $Z_1$ is independently selected from —$NH_2$, —OH, —SH, and —COOH; $R_1$ and $R_2$ independently can have the formula:

(V)

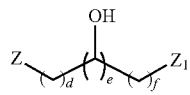

wherein d is any single number from 0 to 100, e is any single number from 0 to 100, f is any single number from 0 to 100, Z is a covalent bond linking one organic moiety to another, and $Z_1$ is independently selected from —$NH_2$, —OH, —SH, and —COOH; B can be any one of (XXIII)

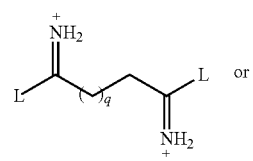

(XIV)

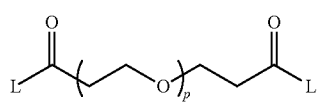

in which q is any single number from 1-20; p is any single number from 20-200; and L is a leaving group, where these B subunits are paired with any one of the A subunits described above. In more particular embodiments, the polymer containing a polyol nanoparticle segment of the targeted nanoparticles shown in structural unit of formula (I) can be:

(XXV)

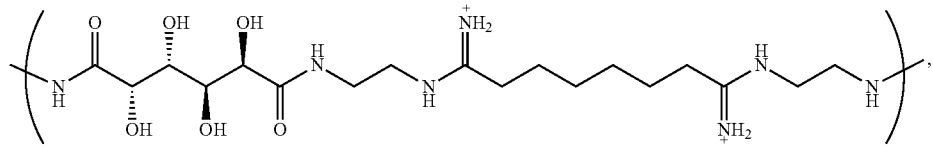

the polymer containing a polyol nanoparticle segment of the targeted nanoparticles shown in structural unit of formula (II) can be:

(XXVI)

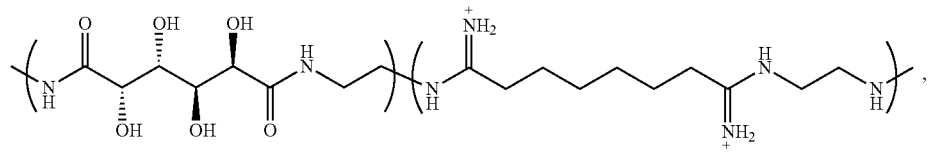

and
the polymer containing a polyol nanoparticle segment of the targeted nanoparticles shown in structural unit of formula (III) can be:

(XXVII)

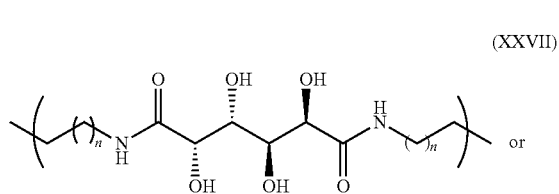 or (XXVIII)

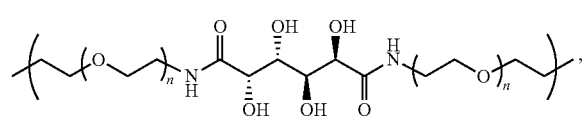, in which n is any single number from 1-20. In some embodiments of the described targeted nanoparticle, the polymer containing a polyol is:

(XXIX)

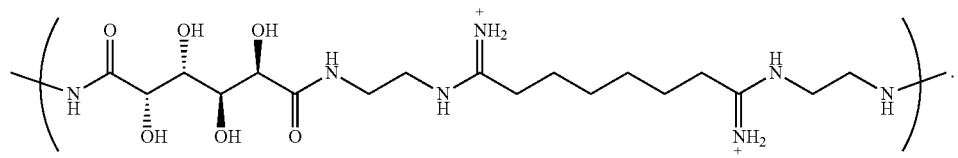.

In summary, any one of the formulas for subpart A (formula VI, VII, or VIII) can be combined with any one of the formulas for subpart B (formula XXIII or XIV) to form the polymer containing a polyol of the described targeted nanoparticles. In certain aspects described herein the targeted nanoparticles can have a polymer containing a polyol formed from the combination of anyone of the formulas for subpart A (IX, X, or XI) with any one of the formulas for subpart B (formula XXIII or XIV).

The described targeted nanoparticles can also have a polymer containing a boronic acid, coupled to the polymer containing a polyol with a reversible covalent linkage. In some embodiments the nanoparticle will be configured to present the polymer containing a boronic acid to an environment external to the nanoparticle. In still further embodiments, the polymer containing the boronic acid is conjugated to a targeting ligand at its terminal end opposite the nanoparticle. In some embodiments the polymer containing a boronic acid comprises at least one terminal boronic acid group and has the general formula:

(XXX)

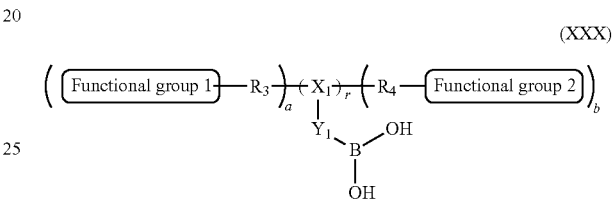

where $R_3$ and $R_4$ are independently an hydrophilic organic polymer, $X_1$ is an organic moiety containing one or more of —C, —N, or —B, $Y_1$ is an alkyl group of formula —$C_mH_{2m}$—, in which m is ≥1 or an aromatic group, r is any single number from 1-1000, a is any single number from 0-3, and b is any single number from 0-3 and functional group 1 and functional group 2 may be the same or different and may independently comprise —$B(OH)_2$, —$OCH_3$, —($X_1$)—($Y_1$)—$B(OH)_2$, —COOH, —$NH_2$, or —OH. In some embodiments these variable subparts of the described polymer containing a boronic acid can be selected from the following: $R_3$ and $R_4$ may be $(CH_2CH_2O)_t$, where t is any single number from 2 to 2000; $X_1$ is any one of —NH—C(=O)—, —S—S—, —C(=O)—NH—, —O—C(=O)— or —C(=O)—O— and $Y_1$ is a phenyl group. In some embodiments these variable subparts of the described polymer containing a boronic acid can be selected from the following: $R_3$ and $R_4$ may be $(CH_2CH_2O)_t$, where t is any single number from 2 to 2000; $X_1$ is any one of —NH—C(=O)—, —S—S—, —C(=O)—NH—, —O—C(=O)— or —C(=O)—O— and $Y_1$ is a phenyl group, and r can have a value of 1, a can have a value of 0 and b can have a value of 1. In a particular embodiment the targeted nanoparticle of described herein can include a polymer containing a boronic acid having the following formula:

(XXXI)

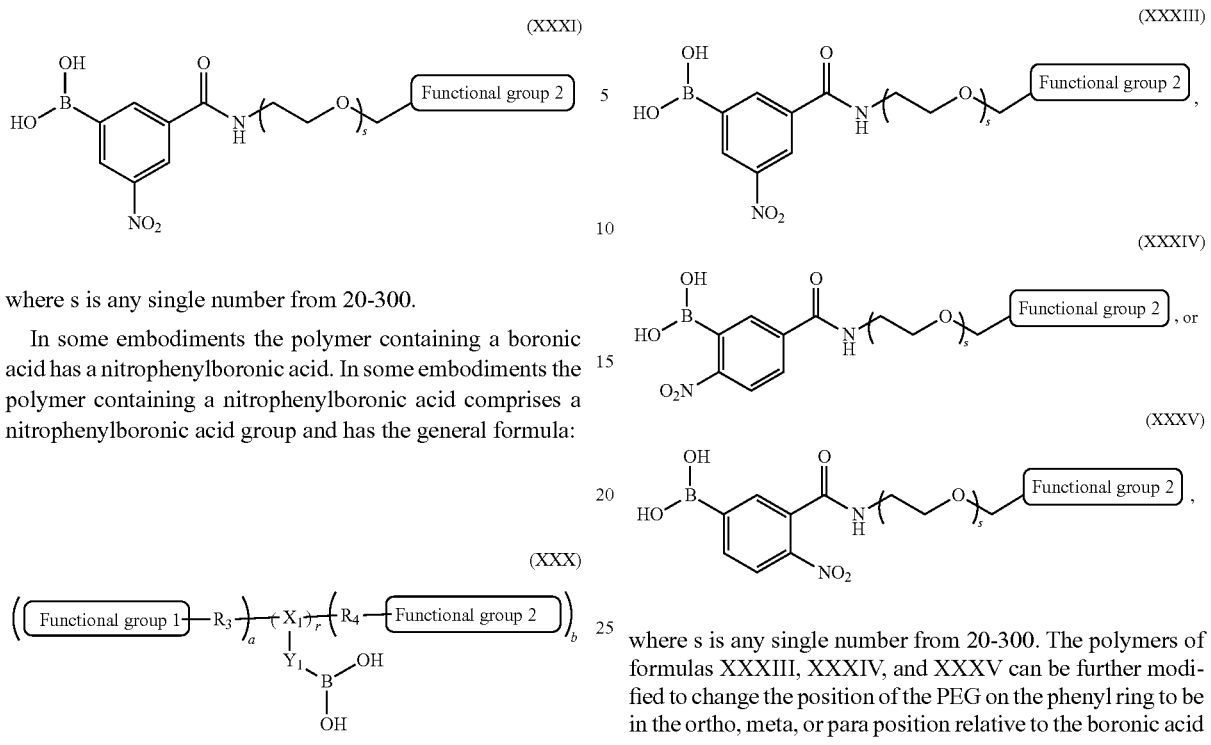

where s is any single number from 20-300.

In some embodiments the polymer containing a boronic acid has a nitrophenylboronic acid. In some embodiments the polymer containing a nitrophenylboronic acid comprises a nitrophenylboronic acid group and has the general formula:

(XXX)

where $R_3$ and $R_4$ are independently an hydrophilic organic polymer, $X_1$ is an organic moiety containing one or more of —C, —N, or —B, $Y_1$ is an alkyl group of formula —$C_mH_{2m}$—, in which m is ≥1 or an aromatic group, r is any single number from 1-1000, a is any single number from 0-3, and b is any single number from 0-3 and functional group 1 and functional group 2 may be the same or different and may independently comprise —B(OH)$_2$, —OCH$_3$, —($X_1$)—($Y_1$)—B(OH)$_2$, —COOH, —NH$_2$, or —OH. In some embodiments these variable subparts of the described polymer containing a boronic acid can be selected from the following: $R_3$ and $R_4$ may be (CH$_2$CH$_2$O)$_t$, where t is any single number from 2 to 2000; $X_1$ is any one of —NH—C(=O)—, —S—S—, —C(=O)—NH—, —O—C(=O)— or —C(=O)—O— and $Y_1$ is a nitrophenyl group. In some embodiments these variable subparts of the described polymer containing a nitrophenylboronic acid can be selected from the following: $R_3$ and $R_4$ may be (CH$_2$CH$_2$O)$_t$, where t is any single number from 2 to 2000; $X_1$ is any one of —NH—C(=O)—, —S—S—, —C(=O)—NH—, —O—C(=O)— or —C(=O)—O— and $Y_1$ is a nitrophenyl group, and r can have a value of 1, a can have a value of 0 and b can have a value of 1. In each of the embodiments of the polymer containing a nitrophenylboronic acid, the nitro group can be at either the ortho, meta, or para position, relative to the boronic acid group, of the phenyl ring. In still further embodiments, the polymer containing a nitrophenylboronic acid can have additional groups present on the phenyl ring, such as a methyl group. In a particular embodiment the targeted nanoparticle of described herein can include a polymer containing a boronic acid having any one of the following formulas:

where s is any single number from 20-300. The polymers of formulas XXXIII, XXXIV, and XXXV can be further modified to change the position of the PEG on the phenyl ring to be in the ortho, meta, or para position relative to the boronic acid group.

In summary, any one of the formulas for subpart A (formula VI, VII, or VIII) can be combined with any one of the formulas for subpart B (formula XXIII or XIV) to form the polymer containing a polyol nanoparticle segment of the described targeted nanoparticles, the resulting polymer containing a polyol can then be coupled to a polymer containing a boronic acid, where the polymer containing a boronic acid is either a phenylboronic acid or a nitrophenylboronic acid. In some embodiments the conjugation between the described polymer containing a polyol and the described polymer containing a boronic acid will be mediated by at least one hydroxyl group of the boronic acid group. In certain aspects described herein the targeted nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid having formula XXX. In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid corresponding to any one of formula XXXI, XXXIII, XXXIV, or XXXV.

In some aspects described herein the nanoparticles formed from either the polymer containing a polyol nanoparticle segment described herein or the combination of a polymer containing a polyol nanoparticle segment and a polymer containing a boronic acid are conjugated to a targeting ligand to form a targeted nanoparticle having a targeting ligand to nanoparticle ratio of 3:1. In some aspects described herein the nanoparticles formed from either the polymer containing a polyol nanoparticle segment described herein or the combination of a polymer containing a polyol nanoparticle segment and a polymer containing a boronic acid are conjugated to a targeting ligand to form a targeted nanoparticle having a targeting ligand to nanoparticle ratio of 1:1. In some aspects described herein the nanoparticles formed from either the polymer containing a polyol nanoparticle segment described herein or the combination of a polymer containing a polyol nanoparticle segment and a polymer containing a boronic acid are conjugated to one single targeting ligand to form a targeted nanoparticle. In some aspects, the described targeting ligand is conjugated to the polymer containing a boronic acid at the terminal end opposite the boronic acid. The targeting ligand conjugated to the described targeted nanoparticle can be any one of a protein, protein fragment, an amino acid peptide, or an aptamer from either amino acids or polynucleotides, or other high affinity molecules known to bind a target of interest. In some embodiments a targeting ligand that is a protein, or protein fragment, can be any one of an antibody, a cellular receptor, a ligand for a cellular receptor, such as transferrin, or a protein or chimeric protein having a portion thereof. Where the targeted ligand is an antibody, the antibody can be a human, murine, rabbit, non-human primate, canine, or rodent antibody, or a chimeric composed of any two such antibodies. Furthermore, the antibody may be humanized such that only the CDR segments or a small portion of the variable region comprising a CDR segment is non-human and the remainder of the antibody is human. The antibodies described herein can be of any isotype, such as IgG, IgM, IgA, IgD, IgE, IgY or another type of isotype understood to be produced by a mammal. In some embodiments the targeting ligand may only include the amino acid peptide from an antibody, a cellular receptor, a ligand for a cellular receptor that is responsible for binding to its target.

In some aspects, a nanoparticle formed from any one of the formulas for subpart A (formula VI, VII, or VIII) combined with any one of the formulas for subpart B (formula XXIII or XIV) to form the polymer containing a polyol nanoparticle segment of the described targeted nanoparticles, further coupled to any of 5, 4, 3, 2, or 1 polymers containing a boronic acid, such as phenylboronic acid or a nitrophenlyboronic acid that is conjugated to a targeting ligand.

In some aspects, a nanoparticle formed from any one of the formulas for subpart A (formula VI, VII, or VIII) combined with any one of the formulas for subpart B (formula XXIII or XIV) to form the polymer containing a polyol nanoparticle segment of the described targeted nanoparticles, further coupled to a single polymer containing a boronic acid, such as phenylboronic acid or a nitrophenlyboronic acid that is conjugated to a targeting ligand.

In certain aspects described herein the targeted nanoparticles can have a polymer containing a polyol formed from the combination of anyone of the formulas for subpart A (IX, X, or XI) with any one of the formulas for subpart B (formula XXIII or XIV), which may be coupled to any of 5, 4, 3, 2, or 1 polymers containing a boronic acid having formula XXX that is coupled to a targeting ligand at its terminal end opposite the boronic acid.

In certain aspects described herein the targeted nanoparticles can have a polymer containing a polyol formed from the combination of anyone of the formulas for subpart A (IX, X, or XI) with any one of the formulas for subpart B (formula XXIII or XIV), which may be coupled to a single polymer containing a boronic acid having formula XXX that is coupled to a targeting ligand at its terminal end opposite the boronic acid.

In some aspects, a nanoparticle formed from any one of the formulas for subpart A (formula VI, VII, or VIII) combined with any one of the formulas for subpart B (formula XXIII or XIV) to form the polymer containing a polyol nanoparticle segment of the described targeted nanoparticles, further coupled to any of 5, 4, 3, 2, or 1 polymers containing a boronic acid, such as phenylboronic acid or a nitrophenlyboronic acid that is conjugated to a targeting ligand, where the resulting targeted nanoparticle is conjugated to only a single targeting ligand.

In some aspects, a nanoparticle formed from any one of the formulas for subpart A (formula VI, VII, or VIII) combined with any one of the formulas for subpart B (formula XXIII or XIV) to form the polymer containing a polyol nanoparticle segment of the described targeted nanoparticles, further coupled to a single polymer containing a boronic acid, such as phenylboronic acid or a nitrophenlyboronic acid that is conjugated to a targeting ligand, where the resulting targeted nanoparticle is conjugated to only a single targeting ligand.

In certain aspects described herein the targeted nanoparticles can have a polymer containing a polyol formed from the combination of anyone of the formulas for subpart A (IX, X, or XI) with any one of the formulas for subpart B (formula XXIII or XIV), which may be coupled to any of 5, 4, 3, 2, or 1 polymers containing a boronic acid having formula XXX that is coupled to a targeting ligand at its terminal end opposite the boronic acid, where the resulting targeted nanoparticle is conjugated to only a single targeting ligand.

In certain aspects described herein the targeted nanoparticles can have a polymer containing a polyol formed from the combination of anyone of the formulas for subpart A (IX, X, or XI) with any one of the formulas for subpart B (formula XXIII or XIV), which may be coupled to a single polymer containing a boronic acid having formula XXX that is coupled to a targeting ligand at its terminal end opposite the boronic acid, where the resulting targeted nanoparticle is conjugated to only a single targeting ligand.

In some embodiments the targeted nanoparticles described herein are conjugated to any a targeting ligand. In some embodiments the targeted nanoparticles described herein are conjugated to a single targeting ligand. In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to any of 5, 4, 3, 2, or 1 polymers containing a boronic acid corresponding to any one of formula XXXI, XXXIII, XXXIV, or XXXV, that is further conjugated to a targeting ligand selected from one or more of a protein, protein fragment, an amino acid peptide, or an aptamer.

In some embodiments the targeted nanoparticles described herein are conjugated to a single targeting ligand. In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid corresponding to any one of formula XXXI, XXXIII, XXXIV, or XXXV, that is further conjugated to a single targeting ligand selected from a protein, protein fragment, an amino acid peptide, or an aptamer.

In some embodiments the targeted nanoparticles described herein are conjugated to a single targeting ligand. In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to any of 5, 4, 3, 2, or 1 polymers containing a boronic acid corresponding to any one of formula XXXI, XXXIII, XXXIV, or XXXV, that is further conjugated to an antibody, cellular receptor, ligand for a cellular receptor, or a protein or chimeric protein having a portion thereof.

In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid corresponding to any one of formula XXXI, XXXIII, XXXIV, or XXXV, that is further conjugated to a single antibody, cellular receptor, ligand for a cellular receptor, or a protein or chimeric protein having a portion thereof.

In some embodiments the targeted nanoparticles described herein are conjugated to a single targeting ligand. In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid corresponding to any one of formula XXXI, XXXIII, XXXIV, or XXXV, that is further conjugated to a single targeting ligand selected from a protein, protein fragment, an amino acid peptide, or an aptamer, where the resulting targeted nanoparticle is conjugated to only a single targeting ligand.

In some embodiments the targeted nanoparticles described herein are conjugated to a single targeting ligand. In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to any of 5, 4, 3, 2, or 1 polymers containing a boronic acid corresponding to any one of formula XXXI, XXXIII, XXXIV, or XXXV, that is further conjugated to an antibody, cellular receptor, ligand for a cellular receptor, or a protein or chimeric protein having a portion thereof, where the resulting targeted nanoparticle is conjugated to only a single targeting ligand.

In some embodiments described herein, the targeted nanoparticles can have a polymer containing a polyol formed from the combination of anyone of the formulas for subpart A (IX, X, or XI) with any one of the formulas for subpart B (formula XXIII or XIV), which can then be coupled to a polymer containing a boronic acid corresponding to any one of formula XXXI, XXXIII, XXXIV, or XXXV, that is further conjugated to a single antibody, cellular receptor, ligand for a cellular receptor, or a protein or chimeric protein having a portion thereof, where the resulting targeted nanoparticle is conjugated to only a single targeting ligand.

The targeted nanoparticles described herein can further include a compound. In some embodiments the compound can be one or more therapeutic agents, such as a small molecule chemotherapeutic agent or a polynucleotide. In some embodiments the polynucleotide can be any one or more of DNA, RNA, or interfering RNA (such as shRNA, siRNA or miRNA). In some embodiments the small molecule chemotherapeutic agent can be one or more of camptothecin, an epothilone, or a taxane. The targeted nanoparticles described herein can also include a combination of one or more polynucleotides with one or more small molecule chemotherapeutic agents.

Having discussed the various types of nanoparticles and targeted nanoparticles that can be produced using the components described herein, the following particular embodiments can be produced. In one embodiment the described targeted nanoparticle has a mucic acid-containing polymer, a therapeutic agent selected from camptothecin, an epothilone, a taxane, or an interfering RNA sequence, a polymer containing a phenylboronic acid, having formula XXXI, XXXIII, XXXIV, or XXXV, that is coupled to the mucic acid polymer with a reversible covalent linkage, and the targeted nanoparticle is configured to present the polymer containing the phenylboronic acid to an environment external to the nanoparticle, where the polymer containing the phenylboronic acid is conjugated to a targeting ligand at its terminal end opposite the nanoparticle, wherein the targeted nanoparticle comprises one single targeting ligand.

In one embodiment the described targeted nanoparticle has a mucic acid-containing polymer, a therapeutic agent selected from camptothecin, an epothilone, a taxane, or an interfering RNA sequence, a polymer containing a phenylboronic acid, having formula XXXI, XXXIII, XXXIV, or XXXV, that is coupled to the mucic acid polymer with a reversible covalent linkage, and the targeted nanoparticle is configured to present the polymer containing the phenylboronic acid to an environment external to the nanoparticle, where the polymer containing the phenylboronic acid is conjugated to an antibody at its terminal end opposite the nanoparticle, wherein the targeted nanoparticle comprises one single antibody.

In one embodiment the described targeted nanoparticle has a mucic acid-containing polymer, a therapeutic agent selected from camptothecin, an epothilone, a taxane, or an interfering RNA sequence, a polymer containing a phenylboronic acid, having formula XXXI, XXXIII, XXXIV, or XXXV, that is coupled to the mucic acid polymer with a reversible covalent linkage, and the targeted nanoparticle is configured to present the polymer containing the phenylboronic acid to an environment external to the nanoparticle, where the polymer containing the phenylboronic acid is conjugated to any one of a human, murine, rabbit, non-human primate, canine, or rodent antibody, or a chimeric antibody composed of any two such antibodies, where the antibody is any one of an IgG, IgD, IgM, IgE, IgA or IgY isotype, at its terminal end opposite the nanoparticle, wherein the targeted nanoparticle comprises one single antibody.

In one embodiment the described targeted nanoparticle has a mucic acid-containing polymer, a therapeutic agent selected from camptothecin, an epothilone, a taxane, or an interfering RNA sequence, a polymer containing a phenylboronic acid, having formula XXXI, XXXIII, XXXIV, or XXXV, that is coupled to the mucic acid polymer with a reversible covalent linkage, and the targeted nanoparticle is configured to present the polymer containing the phenylboronic acid to an environment external to the nanoparticle, where the polymer containing the phenylboronic acid is conjugated to a cellular receptor at its terminal end opposite the nanoparticle, wherein the targeted nanoparticle comprises one single cellular receptor.

In one embodiment the described targeted nanoparticle has a mucic acid-containing polymer, a therapeutic agent selected from camptothecin, an epothilone, a taxane, or an interfering RNA sequence, a polymer containing a phenylboronic acid, having formula XXXI, XXXIII, XXXIV, or XXXV, that is coupled to the mucic acid polymer with a reversible covalent linkage, and the targeted nanoparticle is configured to present the polymer containing the phenylboronic acid to an environment external to the nanoparticle, where the polymer containing the phenylboronic acid is conjugated to a receptor ligand at its terminal end opposite the nanoparticle, wherein the targeted nanoparticle comprises one single receptor ligand.

In view of the forgoing description, the following items are provided to illustrate particular embodiments of the described subject matter:

1. A nanoparticle comprising a polymer containing a polyol and a polymer containing a nitrophenylboronic acid, wherein the polymer containing a nitrophenylboronic acid is coupled to the polymer containing a polyol with a reversible covalent linkage, and wherein the nanoparticle is configured to present the polymer containing a nitrophenylboronic acid to an environment external to the nanoparticle.

2. The nanoparticle of item 1, wherein the polymer containing a polyol comprises one or more of at least one of the following structural units

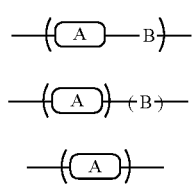

X is independently selected from an aliphatic group containing one or more of —H, —F, —C, —N or —O; and Y is independently selected from —OH or an organic moiety presenting an —OH, and B is an organic moiety linking one of the $R_1$ and $R_2$ of a first said moiety A with one of the $R_1$ and $R_2$ of a second said moiety A in the polymer.

3. The nanoparticle of item 2, wherein $R_1$ and $R_2$ independently have the formula:

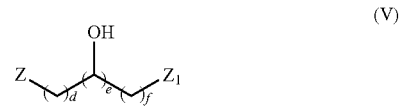

wherein d is from 0 to 100;

e is from 0 to 100;

f is from 0 to 100;

Z is a covalent bond linking one organic moiety to another, and $Z_1$ is independently selected from —$NH_2$, —OH, —SH, and —COOH 4. The nanoparticle of item 2 or 3, wherein X is $C_nH_{2n+1}$, in which n is to 0-5; and wherein Y is —OH 5. The nanoparticle of any one of items 2-4, wherein A is independently selected from the group consisting of

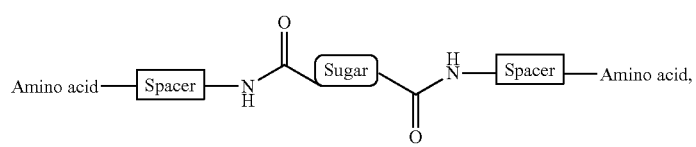

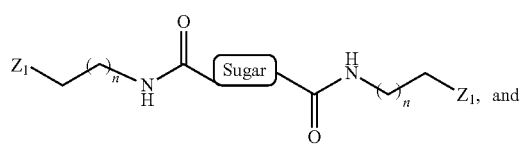

wherein

A is an organic moiety of formula

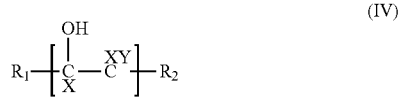

in which $R_1$ and $R_2$ are independently selected from any carbon-based or organic group with a molecular weight of about 10 kDa or less;

wherein the spacer is independently selected from any organic group;

the amino acid is selected from any organic group bearing a free amine and a free carboxylic acid group;

n is 1-20; and $Z_1$ is independently selected from —$NH_2$, —OH, —SH, and —COOH.

6. The nanoparticle of any one of items 2-5, wherein A is independently selected from

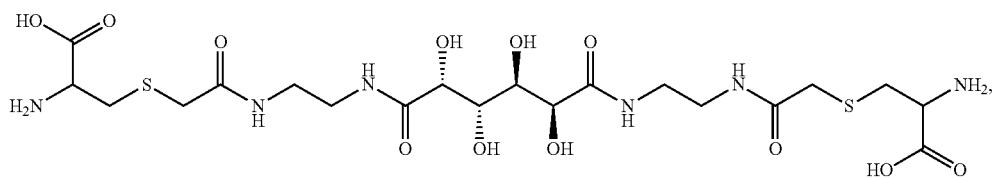
IX
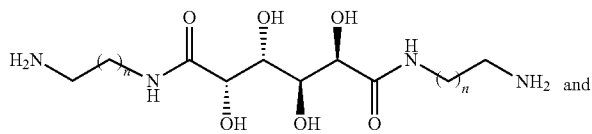
X
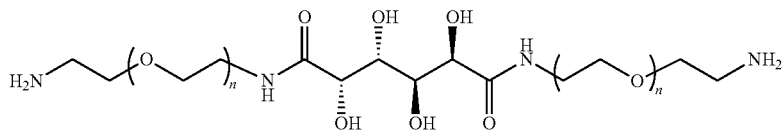
XI
7. The nanoparticle of any one of items 2-6, wherein B is
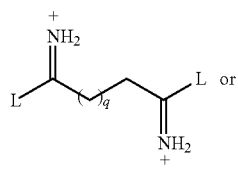
(XXIII)
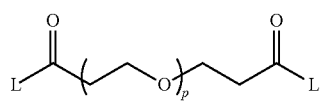
(XIV)
in which
q is 1-20;
p is 20-200; and
L is a leaving group.
8. The nanoparticle of item 2, wherein the structural unit of formula (I) is:
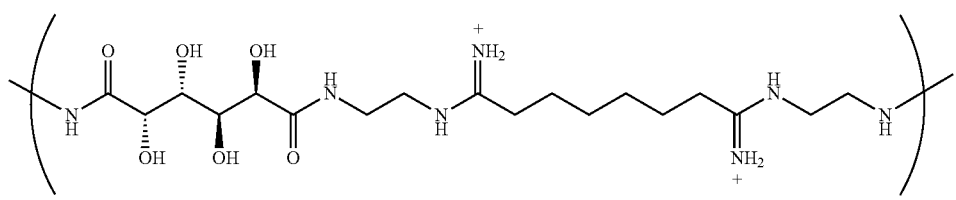
(XXV)

9. The nanoparticle of item 2, wherein the structural unit of formula (II) is:

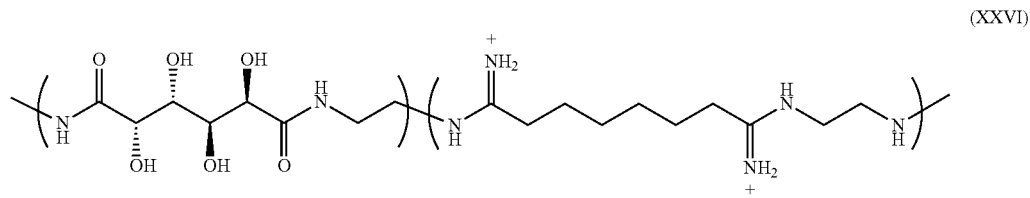

(XXVI)

10. The nanoparticle of item 2, wherein the structural unit of formula (III) is:

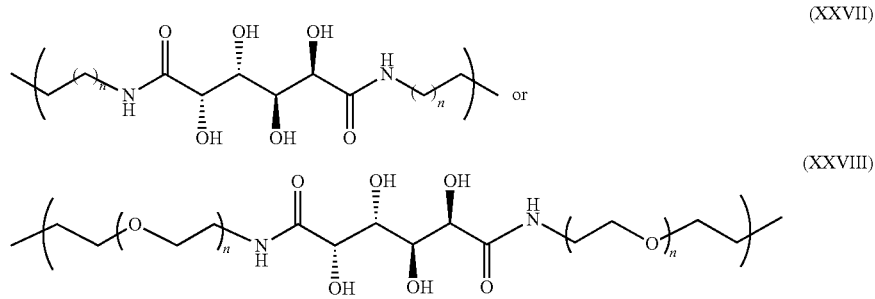

(XXVII)

(XXVIII)

in which
n is 1-20.

11. The nanoparticle of item 1, wherein the polymer containing a polyol is

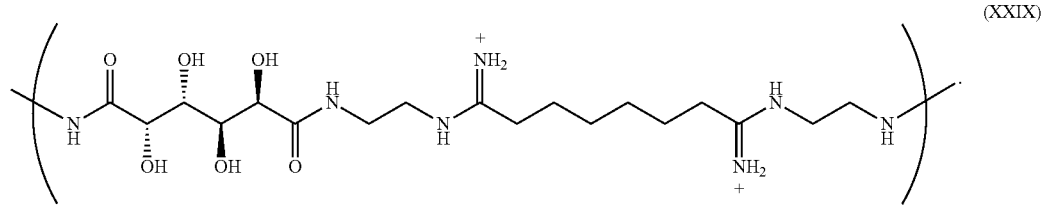

(XXIX)

12. The nanoparticle of any one of items 1-11, wherein the polymer containing a nitrophenylboronic acid comprises at least one terminal nitrophenylboronic acid group and has the general formula:

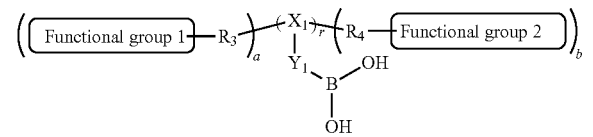

(XXX)

wherein
$R_3$ and $R_4$ are independently an hydrophilic organic polymer,
$X_1$ is an organic moiety containing one or more of —C, —N, or —B,
$Y_1$ is a phenyl group having one or more nitro groups,
r is 1-1000,
a is 0-3, and
b is 0-3.

13. The nanoparticle of item 12, wherein $R_3$ and $R_4$ are $(CH_2CH_2O)_t$, where t is from 2 to 2000.

14. The nanoparticle of item 12 or 13, wherein $X_1$ is —NH—C(=O)—, —S—S—, —C(=O)—NH—, —O—C(=O)— or —C(=O)—O— and $Y_1$ is a phenyl group having one or more nitro groups.

15. The nanoparticle of any one of items 12-14, wherein r=1, a=0 and b=1.

16. The nanoparticle of any one of items 12-15, wherein functional group 1 and functional group 2 are the same or different and are independently selected from —B(OH)$_2$, —OCH$_3$, —OH.

17. The nanoparticle of any one of items 12-16, wherein the polymer containing a nitrophenylboronic acid is:

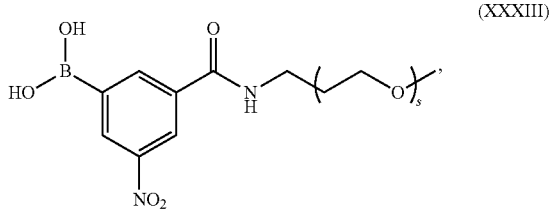

(XXXIII)

-continued

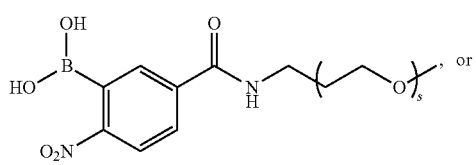

(XXXIV)

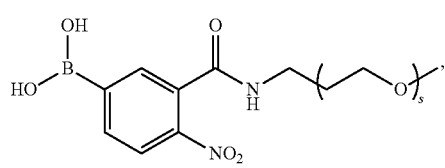

(XXXV)

wherein s=20-300.

18. The nanoparticle of any one of items 1-17, further comprising a compound, wherein the compound forms part of the polymer containing a polyol and/or the polymer containing a nitrophenylboronic acid.

19. The nanoparticle of any one of items 1-17, further comprising a compound, wherein the compound is attached to the polymer containing a polyol and/or the polymer containing a nitrophenylboronic acid.

20. The nanoparticle of any one of items 1-19 further comprising a compound, wherein the compound is a therapeutic agent.

21. The nanoparticle of item 20, wherein the therapeutic agent is a small molecule chemotherapeutic agent or a polynucleotide.

22. The nanoparticle of item 21, wherein the polynucleotide is interfering RNA.

23. The nanoparticle of any one of items 1-22, further comprising one or more compounds, wherein at least one compound is a targeting ligand.

24. The nanoparticle of item 23, wherein the targeting ligand is a protein, an aptamer, a small molecule, an antibody, or an antibody fragment.

25. The nanoparticle of item 23 or 24, wherein the targeting ligand is one single antibody.

26. The nanoparticle of item 25, wherein the one single antibody is conjugated to the terminal portion of the polymer containing a nitrophenylboronic acid.

27. The nanoparticle of item 23, wherein the targeting ligand is selected from transferrin, a protein, an aptamer, a small molecule, an antibody, or an antibody fragment and the nanoparticle further comprises a therapeutic agent selected from camptothecin, an epothilone, a taxane or a polynucleotide or any combination thereof.

28. A composition comprising the nanoparticle of any one of items 1-27 and a suitable vehicle and/or excipient.

29. The composition of item 28, wherein the composition is a pharmaceutical composition and the suitable vehicle and/or excipient is a pharmaceutically acceptable vehicle and/or excipient.

30. The composition of item 29, wherein the nanoparticle further comprises $^{10}B$ as part of at least one polymer containing a nitrophenylboronic acid the composition being formulated for in vivo boron neutron activation therapy.

31. A method to deliver a compound to a target, the method comprising contacting the target with the nanoparticle of any one of items 1-27.

32. The method of item 31, wherein the target is a cancer cell within the body of a mammal.

33. A system to deliver a compound to a target, the system comprising the nanoparticle of any one of items 1-27 to be used to deliver the compound to the target.

34. A method to administer a compound to an individual, the method comprising administering to the individual the nanoparticle of any one of items 1-27 further comprising the compound.

35. A system for administering a compound to an individual, the system comprising at least one polymer containing a polyol and at least one polymer containing a nitrophenylboronic acid capable of reciprocal binding through a reversible covalent linkage, the at least one polymer containing a polyol and polymer containing a nitrophenylboronic acid to be assembled with the compound in a nanoparticle of any one of items 1-27, to be administered to the individual.

36. A polymer containing a nitrophenylboronic acid of formula

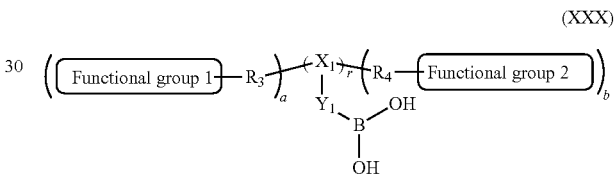

(XXX)

wherein $R_3$ and $R_4$ are independently an hydrophilic organic polymer, $X_1$ is an organic moiety comprising or ore more of —CH, —N, or —B, $Y_1$ is a phenyl group having one or more nitro groups, r is 1-1000, a is 0-3, and b is 0-3.

37. The polymer of item 36 wherein $R_3$ and $R_4$ are independently $(CH_2CH_2O)_t$, where t is 2 to 2000.

38. The polymer of item 36 or 37 wherein $X_1$ is —NH—C(=O)—, —S—S—, —C(=O)—NH—, —O—C(=O)— or —C(=O)—O— and $Y_1$ is a nitrophenyphenyl group.

39. The polymer of item 36, 37, or 38 wherein r is 1, a is 0 and b is 1.

40. The polymer of any one of items 36-39 wherein the functional group 1 and functional group 2 are the same or different and are independently selected from —B(OH)$_2$, —OCH$_3$, —OH.

41. The polymer of any one of items 36-40, further comprising a targeting ligand.

42. The polymer of item 41, wherein the targeting ligand is an antibody.

43. The polymer of item 41, wherein the targeting ligand is one single antibody.

44. The polymer of item 41 or 42, wherein the antibody is conjugated to the terminal portion of the polymer containing a nitrophenylboronic acid.

45. A method to prepare the nanoparticle of any one of items 1-27 comprising contacting the polymer containing a polyol with the polymer containing a nitrophenylboronic acid for a time and under conditions to allow coupling of the polymer containing a polyol with the polymer containing a nitrophenylboronic acid.

46. The method of item 45, said nanoparticle being configured to present the polymer containing a nitrophenlyboronic acid to an environment external to the nanoparticle.

47. A method of item 45 or 46, wherein the polymer containing a polyol is a mucic acid polymer.

48. A method of any one of items 45-47, wherein the polymer nitorphenylboronic acid is any one of:

(XXXIII)

(XXXIV) or (XXXV)

herein s=20-300.

49. A kit for producing a nanoparticle of any one of items 1-27, comprising a comprising a nanoparticle comprising a polymer containing a polyol, a polymer containing a nitrophenlyboronic acid, and instructions for how to conjugate the nanoparticle comprising a polymer containing a polyol and the polymer containing a nitrophenlyboronic acid.

50. The kit of item 49, wherein the polymer containing a polyol is a mucic acid polymer.

51. The kit of item 49 or 50, wherein the polymer containing a nitorphenylboronic acid is any one of:

(XXXIII)

(XXXIV) or (XXXV)

wherein s=20-300.

EXAMPLES

The methods system herein described are further illustrated in the following examples, which are provided by way of illustration and are not intended to be limiting. A person skilled in the art will appreciate the applicability of the features described in detail for methods of nucleic acid detection and detection of other targets, such as proteins, antigens, eukaryotic or prokaryotic cells, and the like.

All chemical reagents were obtained from commercial suppliers and were used as received without further purification. Polymer samples were analyzed on a Viscotek GPC System equipped with a TDA 302 triple detector array consisting of a differential refractive index (RI) detector, a differential viscometer and a low angle light scattering detector. A 7.5% acetic acid solution was used as eluant at a 1 mL/min flow rate.

pGL3, a plasmid containing the firefly luciferase gene was extracted and purified from bacteria expressing pGL3. siGL3 was purchased from Integrated DNA Technologies (sequence provided below). siCON1 (sequence provided below) was purchased from Dharmacon. HeLa cells were used to determine the efficacy of pDNA or siRNA delivery by the cationic mucic acid diamine-DMS polymer.

TABLE 1 siRNA sequences

| Plasmid | Sequences | SEQ ID NO |
|---|---|---|
| siGL3 | GUGCCAGAGUCCUUCGAUAdTdT (sense) | SEQ ID NO: 1 |
|  | UAUCGAAGGACUCUGGCACdTdT (antisense) | SEQ ID NO: 2 |
| siCON1 | UAGCGACUAAACACAUCAAUU (sense) | SEQ ID NO: 3 |
|  | UUGAUGUGUUUAGUCGCUAUU (antisense) | SEQ ID NO: 4 |

Example 1

Synthesis of Mucic Acid Dimethyl Ester, (1)

5 g (22.8 mmol) of mucic acid (Aldrich) was added to a 500 mL round bottom flask containing 120 mL of methanol and 0.4 mL of concentrated sulfuric acid. This mixture was allowed to reflux at 85° C. overnight under constant stirring. The mixture was subsequently filtered, washed with methanol and then recrystallized from a mixture of 80 mL methanol and 0.5 mL triethylamine. After drying under vacuum overnight, 8.0 g (33.6 mmol, 71%) of mucic acid dimethyl ester was obtained. $^1$H NMR ((CD$_3$)$_2$SO) δ 4.88-4.91 (d, 2H), 4.78-4.81 (m, 2H), 4.28-4.31 (d, 2H), 3.77-3.78 (d, 2H), 3.63 (s, 6H). ESI/MS (m/z): 261.0 [M+Na]$^+$

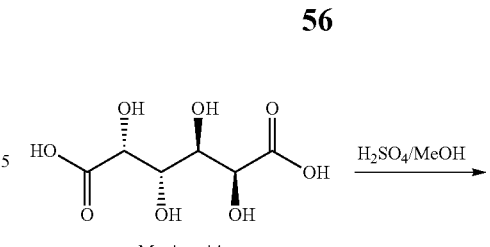
Mucic acid

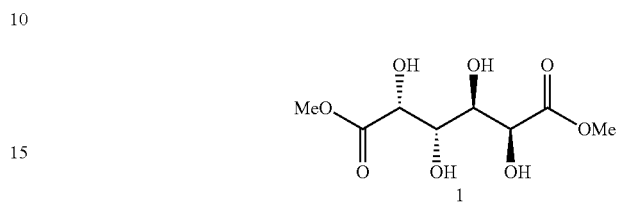

Example 2

Synthesis of N—BOC-Protected Mucic Acid Diamine, (2)

A mixture of 8 g (33.6 mmol) of Mucic Acid Dimethyl Ester (1; Example 1), 12.4 mL (88.6 mmol) triethylamine and 160 mL methanol was heated under reflux at 85° C. in a 500 mL round bottom flask under constant stirring for 0.5 h prior to the addition of 14.2 g (88.6 mmol) N—BOC diamine (Fluka) dissolved in methanol (32 mL). This reaction suspension was then returned to reflux. After refluxing overnight, the mixture was filtered, washed with methanol, recrystallized from methanol and then dried under vacuum to yield 9.4 g (19 mmol, 57%) of N—BOC-Protected Mucic Acid Diamine. $^1$H NMR ((CD$_3$)$_2$SO) δ 7.66 (m, 2H), 6.79 (m, 2H), 5.13-5.15 (d, 2H), 4.35-4.38 (d, 2H), 4.08-4.11 (m, 2H), 3.78-3.80 (d, 2H), 2.95-3.15 (m, 8H), 1.38 (s, 18). ESI/MS (m/z): 517.1 [M+Na]$^+$

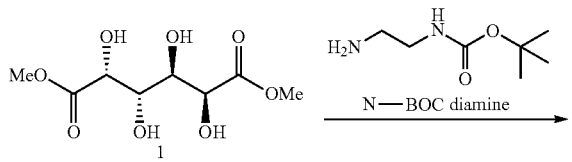

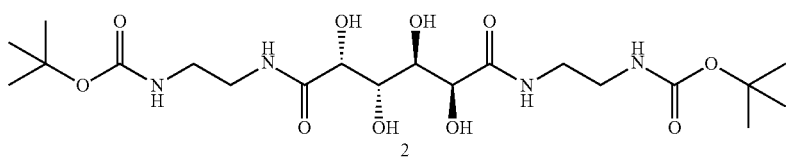

Example 3

Synthesis of Mucic Acid Diamine, (3)

8 g (16.2 mmol) of the N—BOC-Protected Mucic Acid Diamine (2; Example 2) was transferred to a 500 mL round bottom flask containing 3 M HCl in methanol (160 mL) and allowed to reflux overnight at 85° C. under constant stirring. The precipitate was subsequently filtered, washed with methanol and vacuum dried overnight to give 5.7 g (15.6 mmol, 96%) of Mucic Acid Diamine. $^1$H NMR ((CD$_3$)$_2$SO) δ 7.97 (m, 8H), 5.35-5.38 (m, 2H), 4.18-4.20 (m, 2H), 3.82 (m, 2H), 3.35-3.42 (m, 8H), 2.82-2.90 (m, 4H). ESI/MS (m/z): 294.3 [M]$^+$, 317.1 [M+Na]$^+$, 333.0 [M+K]$^+$ ing mixture was stirred at room temperature for 15 h. The mixture was then diluted to 8 mL with water and the pH was brought to 4 with the addition of 1 N HCl. This solution was then dialyzed with a 3500 MWCO dialysis membrane (Pierce pleated dialysis tubing) in ddH$_2$O for 24 h. The dialyzed solution was lyophilized to dryness to give 49 mg of a white fluffy powder. $^1$H NMR (500 MHz, dDMSO) δ 9.15 (bs), 7.92 (bs), 5.43 (bs), 4.58 (bs), 4.17 (bs), 3.82 (bs), 3.37 (bs), 3.28 (bs), 2.82 (bs), 2.41 (bs), 1.61 (bs), 1.28 (bs). $^{13}$C NMR (126 MHz, dDMSO) δ 174.88 (s, 1H), 168.38 (s, 1H), 71.45 (s, 4H), 71.22 (s, 3H), 42.34 (s, 2H), 36.96 (s, 3H), 32.74 (s, 3H), 28.09 (s, 4H), 26.90 (s, 4H). Mw [GPC]=2520, Mw/Mn=1.15.

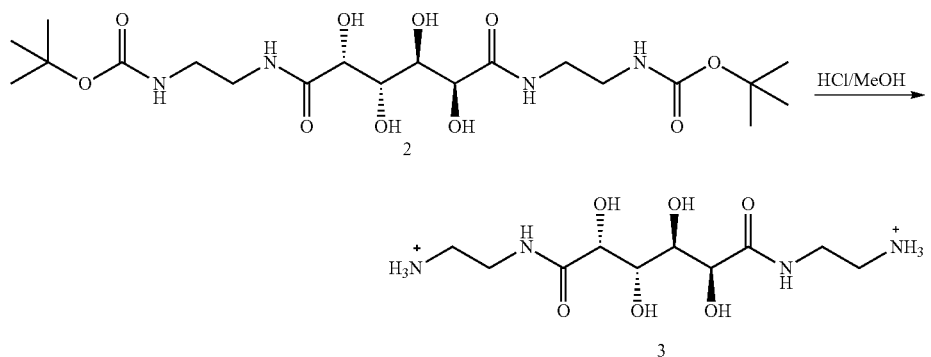

Example 4

Mucic Acid Diamine-DMS Copolymer (MAP), (4)

A 1.5 mL eppendorff tube was charged with a solution of 85.5 mg (0.233 mmol) of the bis(hydrochloride) salt of Example 3 (3) in 0.8 mL of 0.1 M NaHCO$_3$. Dimethylsuberimidate·2HCl (DMS, Pierce Chemical Co., 63.6 mg, 0.233 mmol) was added and the solution was vortexed and centrifuged to dissolve the components. The result-

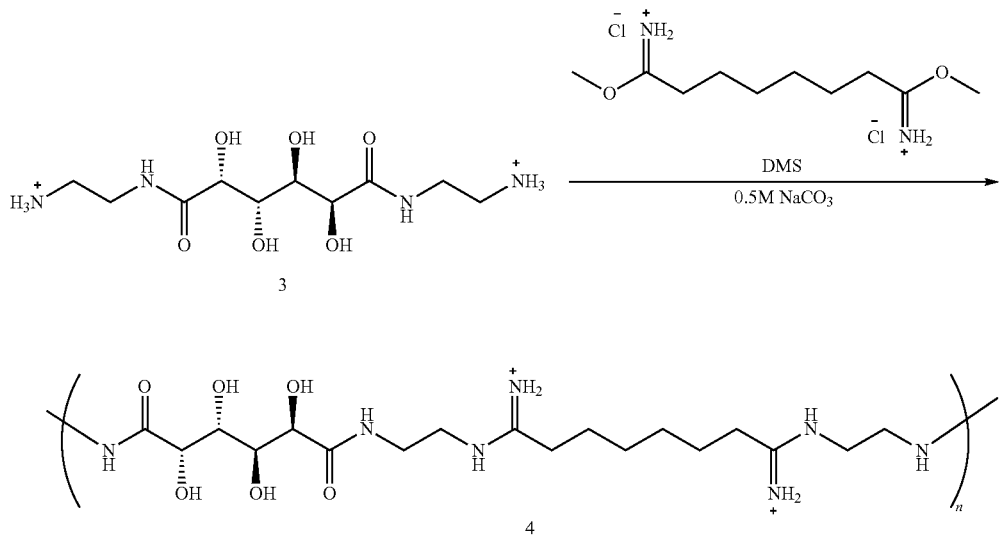

Polymer 4 is an example of a cationic A-B type (repeating structure is ABABAB . . . ) polymer containing a polyol.

Example 5

Boronic Acid-Amide-PEG$_{5000}$, (5)

When a polymer of Example 4 is assembled with nucleic acids, e.g., siRNAs, they will form nanoparticles. These nanoparticles will need to have steric stabilization to be used in mammals and optionally they could have targeting agents included. To perform these two functions, the nanoparticles can be decorated with PEG for steric stabilization and PEG-targeting ligands. To do so, PEG compounds containing boronic acids are prepared. For example, a PEG containing boronic acid can be synthesized according the example below.

332 mg of 4-carboxyphenylboronic acid (2 mmol) was dissolved in 8 mL of SOCl$_2$. To this was added a few drops of DMF and the mixture was refluxed under argon for 2 h. Excess SOCl$_2$ was removed under reduced pressure and the resulting solid was dissolved in 10 mL of anhydrous dichloromethane. To this solution was added 500 mg of PEG$_{5000}$-NH$_2$ (2 mmol) and 418 µL of triethylamine (60 mmol) dissolved in 5 mL of dichloromethane at 0° C. under argon. The resulting mixture was warmed to room temperature and stirring was continued overnight. The dichloromethane solvent was removed under reduced pressure and the resulting liquid was precipitated with 20 mL of diethyl ether. The precipitate was filtered, dried and re-dissolved in ddH$_2$O. The aqueous solution was then filtered with a 0.45 µm filter and dialyzed with a 3500 MWCO dialysis membrane (Pierce pleated dialysis tubing) in ddH$_2$O for 24 h. The dialyzed solution was lyophilized to dryness. $^1$H NMR (300 MHz, dDMSO) δ 7.92-7.77 (m), 4.44 (d), 4.37 (t), 3.49 (m), 2.97 (s).

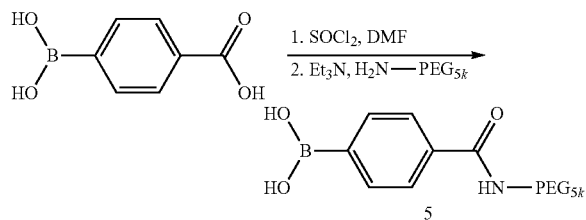

Example 6

Boronic Acid-Disulfide-PEG$_{5000}$, (6)

A cleavable version (under reducing conditions) of the PEG compound of Example 5 can also be synthesized as follows.

250 mg of PEG$_{5000}$-SH (0.05 mmol, LaySanBio Inc.) was added to a glass vial equipped with a stirbar. To this was added 110 mg of aldrithiol-2 (0.5 mmol, Aldrich) dissolved in 4 mL of methanol. The solution was stirred at room temperature for 2 h after which, 77 mg of mercaptophenylboronic acid (0.5 mmol, Aldrich) in 1 mL of methanol was added. The resulting solution was stirred for an additional 2 h at room temperature. Methanol was removed under vacuuo and the residue was re-dissolved in 2 mL of dichloromethane. 18 mL of diethyl ether was added to the dichloromethane solution and the mixture was allowed to sit for 1 h. The resulting precipitate was collected via centrifugation, washed several times with diethyl ether and dried. The dried solid was re-dissolved in water, filtered with a 0.45 µm filter and dialyzed with a 3500 MWCO dialysis membrane (Pierce pleated dialysis tubing) in ddH$_2$O for 15 h. The dialyzed solution was lyophilized to dryness. $^1$H NMR (300 MHz, dDMSO) δ 8.12-8.00 (m), 7.83-7.72 (m), 7.72-7.61 (m), 7.61-7.43 (m), 3.72 (d, J=5.4), 3.68-3.15 (m), 3.01-2.83 (m).

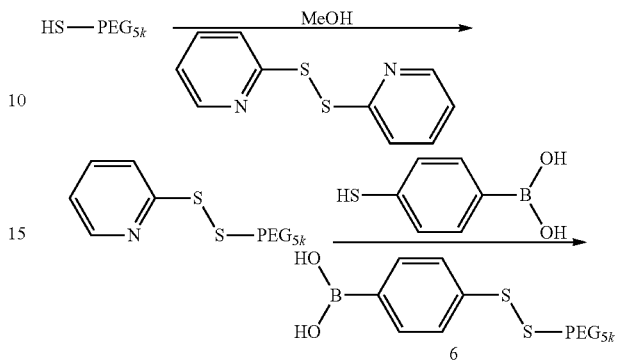

Example 7

Synthesis of 2,3,5,6-Tetrafluorophenyl Boronic Acid-PEG$_{5000}$, (7)

A fluorinated version of the PEG compound containing boronic acids of Example 5 can be synthesized and used as an imaging agent with the therapeutic nanoparticle. The fluorine atoms for imaging can be incorporated as described and illustrated below.

(2,3,5,6)-fluorocarboxyphenylboronic acid is dissolved in excess SOCl$_2$ (~100 eq.) and to it is added a few drops of DMF. The mixture is refluxed under argon for 2 h. Excess SOCl$_2$ is removed under reduced pressure and the resulting residue is dissolved in anhydrous dichloromethane. To this solution, PEG$_{5000}$-NH$_2$ (1 eq.) and triethylamine (30 eq.) dissolved in dichloromethane is added at 0° C. under argon. The resulting mixture is warmed to room temperature and stirring is continued overnight. The dichloromethane solvent is removed under reduced pressure and the resulting liquid is precipitated with diethyl ether. The precipitate is filtered, dried and re-dissolved in ddH$_2$O. The aqueous solution is then filtered with a 0.45 µm filter and dialyzed with a 3500 MWCO dialysis membrane (Pierce pleated dialysis tubing) in ddH$_2$O for 24 h. The dialyzed solution is lyophilized to dryness.

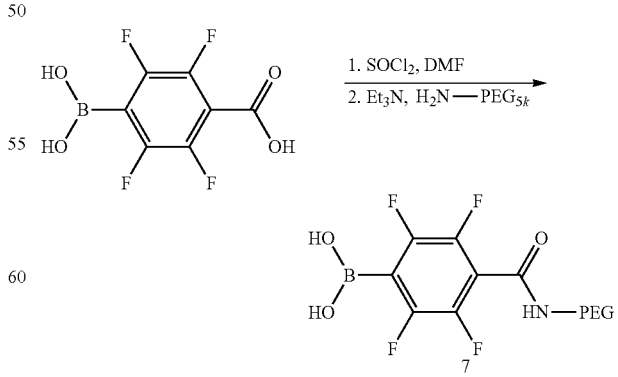

The fluorine containing compound is useful to provide $^{19}$F in the nanoparticle. The $^{19}$F can be detected by magnetic resonance spectroscopy using a standard patient MRI. The addition of the $^{19}F$ enables the nanoparticles to be imaged (can be done for just imaging or with the addition of a therapeutic agent can allow for imaging and therapy).

Example 8

Synthesis of 2,3,5,6-Tetrafluorophenyl Boronic Acid-Disulfide-$PEG_{5000}$, (8)

A fluorinated version of the cleavable PEG compound containing boronic acids of Example 5 can be synthesized and used as an imaging agent with the therapeutic nanoparticle. The fluorine atoms for imaging can be incorporated as described and illustrated below.

250 mg of $PEG_{5000}$-SH (0.05 mmol, LaySanBio Inc.) are added to a glass vial equipped with a stirbar. To this is added 110 mg of aldrithiol-2 (0.5 mmol, Aldrich) dissolved in 4 mL of methanol. The solution is stirred at room temperature for 2 h after which, 77 mg of (2,3,5,6)-fluoro-4-mercaptophenyl-boronic acid (0.5 mmol) in 1 mL of methanol is added. The resulting solution is stirred for an additional 2 h at room temperature. Methanol is removed under vacuuo and the residue is re-dissolved in 2 mL of dichloromethane. 18 mL of diethyl ether is added to the dichloromethane solution and the mixture is allowed to sit for 1 h. The resulting precipitate is collected via centrifugation, washed several times with diethyl ether and dried. The dried solid is re-dissolved in water, filtered with a 0.45 μm filter and dialyzed with a 3500 MWCO dialysis membrane (Pierce pleated dialysis tubing) in $ddH_2O$ for 15 h. The dialyzed solution is lyophilized to dryness.

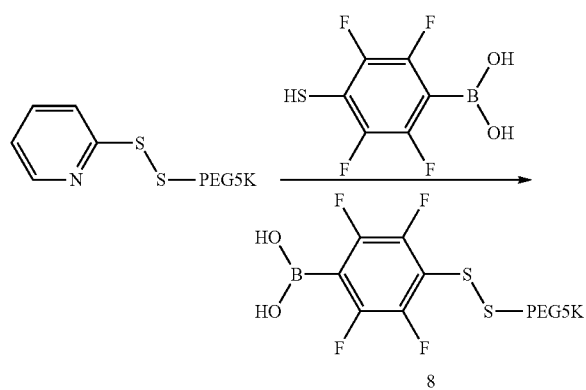

8

Example 9

Synthesis of Boronic Acid-$PEG_{5000}$-Transferrin 9

Figure 12:
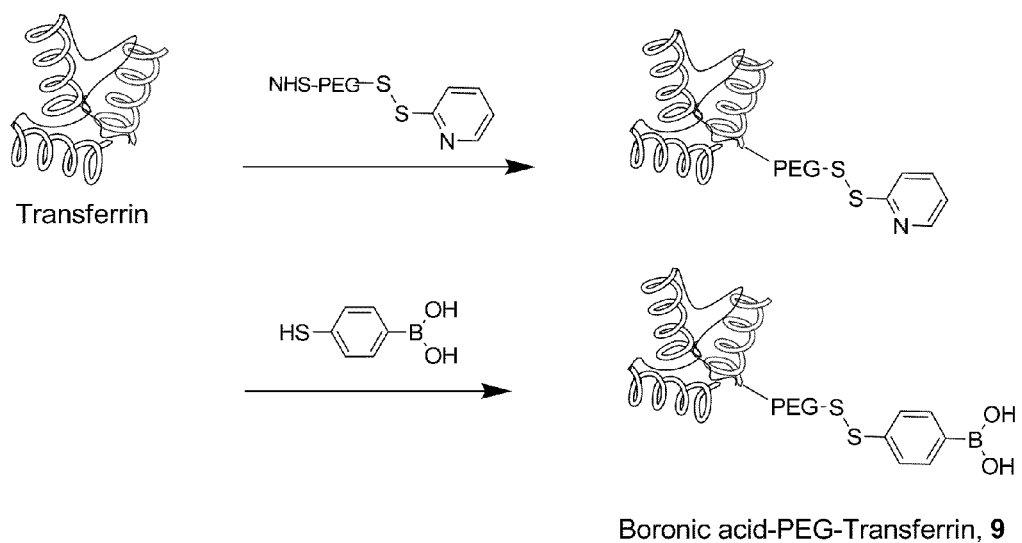
FIG. 12 shows a schematic representation of a synthesis of a polymer containing a boronic acid presenting a targeting ligand according to some embodiments herein described. In particular
Figure 13:
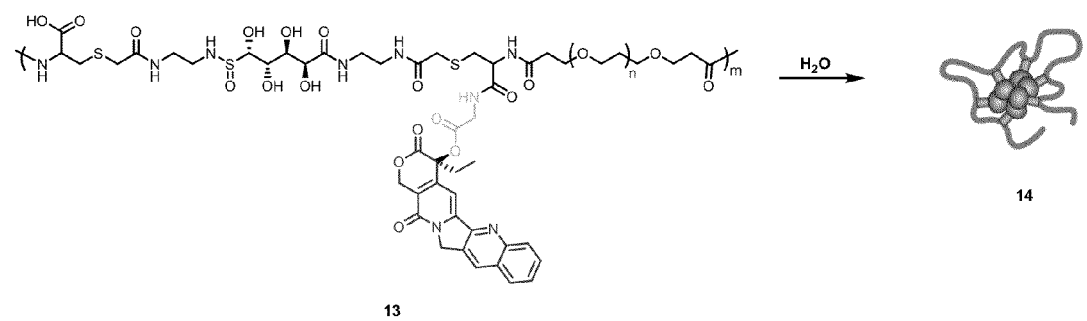
FIG. 13 shows a schematic representation of a synthesis of a nanoparticle according to some embodiments herein described. In particular.
Figure 15:
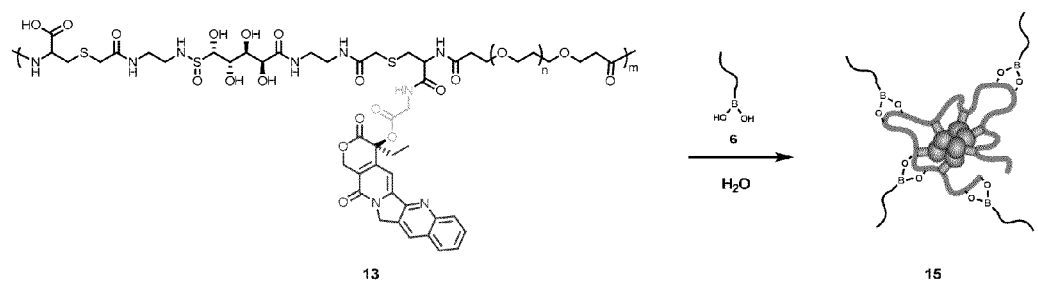
FIG. 15 shows a schematic representation of a synthesis of a nanoparticle according to some embodiments herein described. In particular.

A targeting agent could be placed at the other end of the PEG from the boronic acid in the compounds of Examples 5-8, for example according to an approach schematically illustrated in FIG. 12 with reference to attachment of transferrin.

Thus, the components of a system containing nucleic acids as the therapeutic could be (targeting ligand could be a protein like transferrin (FIG. 12), an antibody or antibody fragment, a peptide like RGD or LHRH, a small molecule like folate or galactose, etc.). A boronic acid PEGylated targeting agent can be synthesized as follows.

In particular, to synthesize the Boronic Acid $PEG_{5000}$-Transferrin according to the approach schematically illustrated in FIG. 12 the following procedure was performed. A solution of 10 mg (0.13 μmol) of Human holo-Transferrin (iron rich) (Sigma Aldrich) in 1 mL of 0.1M PBS buffer (p.H. 7.2) was added to 3.2 mg of OPSS-$PEG_{5000}$-SVA (5 eq, 0.64 μmol, LaysanBio Inc.). The resulting solution was stirred at room temperature for 2 h. The PEGylated Transferrin was purified from the unreacted OPSS-$PEG_{5000}$-SVA using an Ultracel 50,000 MWCO (Amicon Ultra-4, Millipore) and from unreacted Transferrin using a gel filtration column G3000SWx1 (Tosoh Biosep) (confirmed by HPLC and MALDI-TOF analysis). 100 μg of the OPSS-$PEG_{5000}$ PEGylated Transferrin in 100 μL was then incubated at room temperature with 20 μL, 4-mercaptophenylboronic acid (1 μg/μL, 20 μg, 100 eq.) for 1 h. After incubation, the solution was dialyzed twice with a YM-30,000 NMWI device (Millipore) to remove excess 4-mercaptophenylboronic and the pyridyl-2-thione by-product.

Example 10

Formulation of MAP-Nucleic Acid Particles—Gel Retardation Assay

Figure 3:
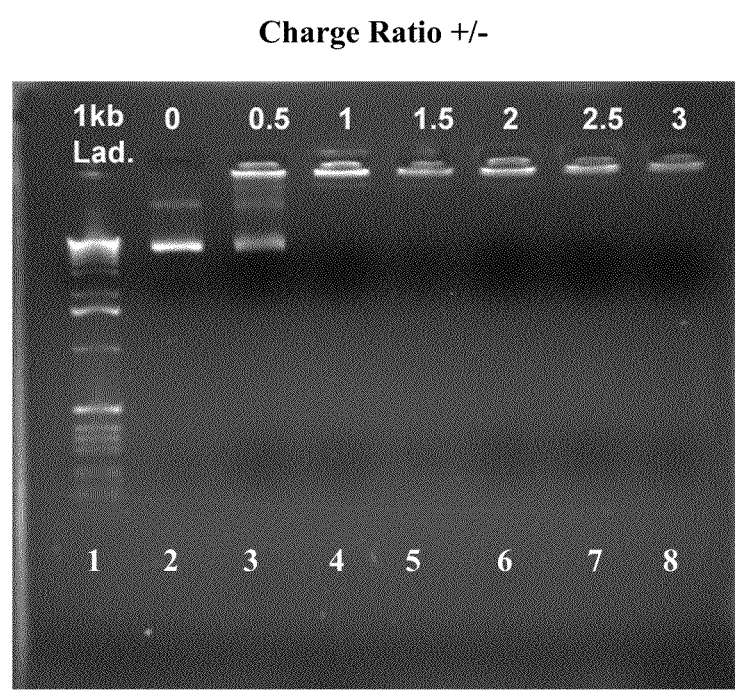
FIG. 3 shows formation of a complex comprising polymers containing polyols and a compound of interest according to an embodiment herein described. In particular.
Figure 4:
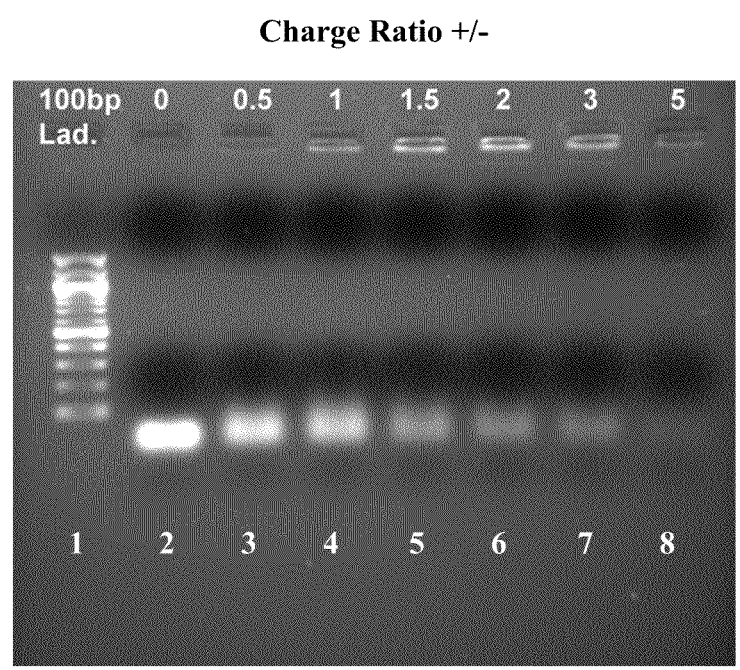
FIG. 4 shows formation of a complex comprising polymers containing polyols and a compound of interest according to an embodiment herein described. In particular.

As diagramed in FIG. 1, 1 μg of plasmid DNA or siRNA in DNAse and RNASe free water (0.1 μg/μL, 10 μL) was mixed with 10 μL of MAP at various concentrations in DNAse and RNASe free water to give charge ratios ("+" charge on polymer to "−" charge on nucleic acid) of 0.5, 1, 1.5, 2, 2.5, and 5. The resulting mixtures were incubated for 30 minutes at room temperature. 10 μL of the 20 μL solutions were loaded onto a 1% agarose gel with 3.5 μL of loading buffer and the gel was electrophoresed at 80 V for 45 minutes as shown in FIGS. 3 and 4. Nucleic acid that is not contained within the nanoparticle will migrate on the gel. These results give guidance to the charge ratios necessary for nucleic acid containment within the nanoparticles.

Example 11

Particle Size and Zeta Potential of MAP-Nucleic Acid Particles

Figure 5:
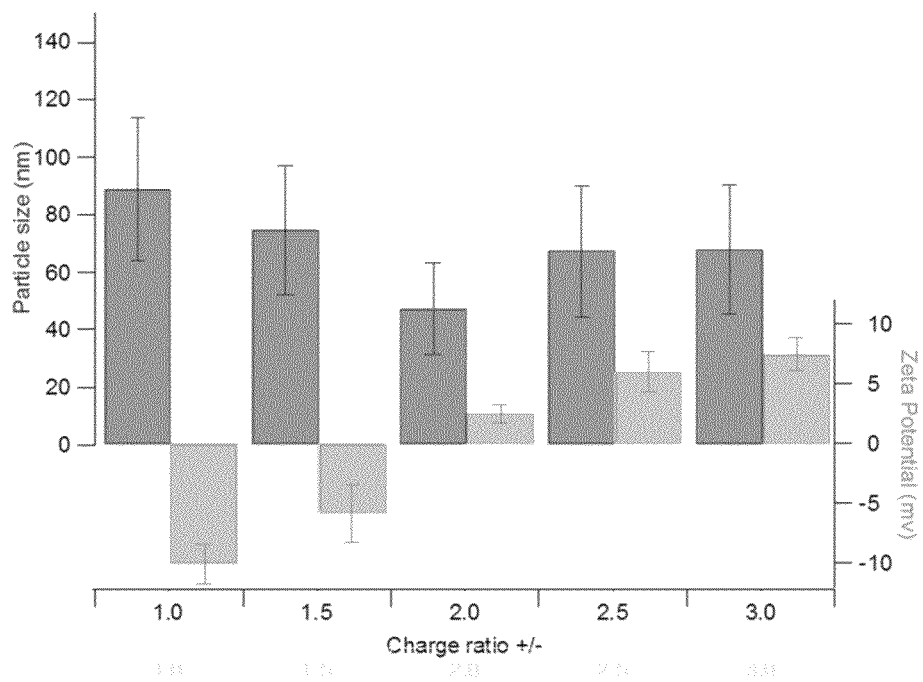
FIG. 5 shows properties of nanoparticles according to some embodiments herein described. In particular.

1 μg of plasmid DNA in DNAse and RNASe free water (0.1 μg/μL, 10 μL) was mixed with 10 μL of MAP at various concentrations in DNAse and RNASe free water to give charge ratios of 0.5, 1, 1.5, 2, 2.5, and 5. The resulting mixtures were incubated for 30 minutes at room temperature. The 20 μL mixture was then diluted with DNAse and RNASe free water to 70 μL for particle size measurements. This 70 μL solution was then diluted to 1400 μL with 1 mM KCl for zeta potential measurements. The particle size and zeta potential measurements were made on a ZetaPals dynamic light scattering (DLS) instrument (Brookhaven Instruments). The results are shown in FIG. 5.

Example 12

Particle Size Stabilization by PEGylation with Boronic Acid PEG

Figure 6:
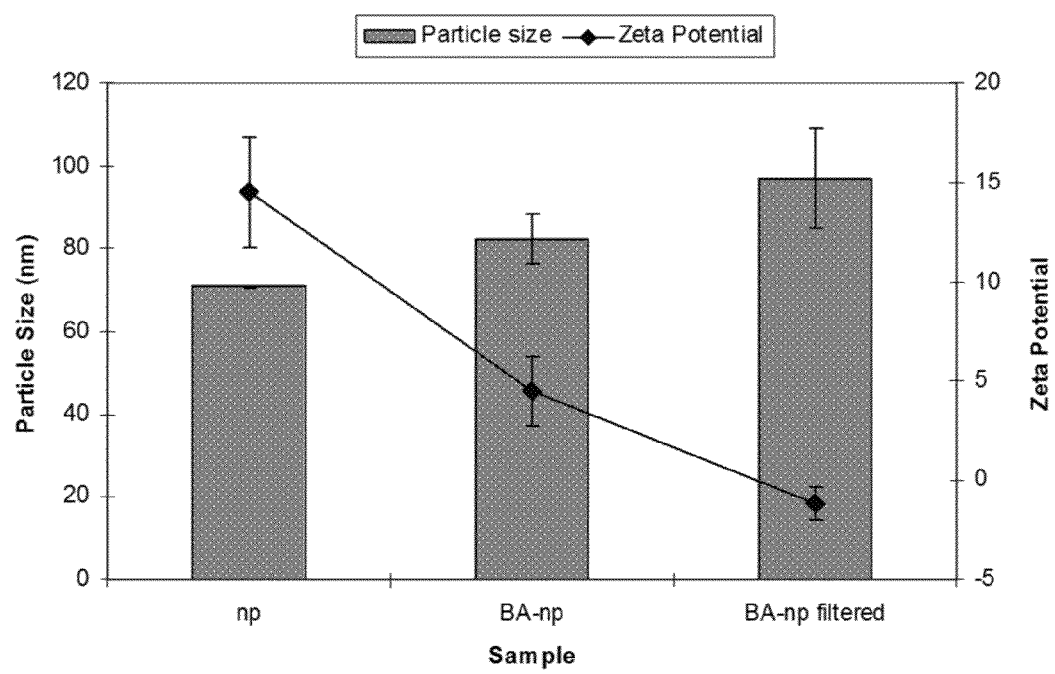
FIG. 6 properties of nanoparticles according to some embodiments herein described. In particular.
Figure 7:
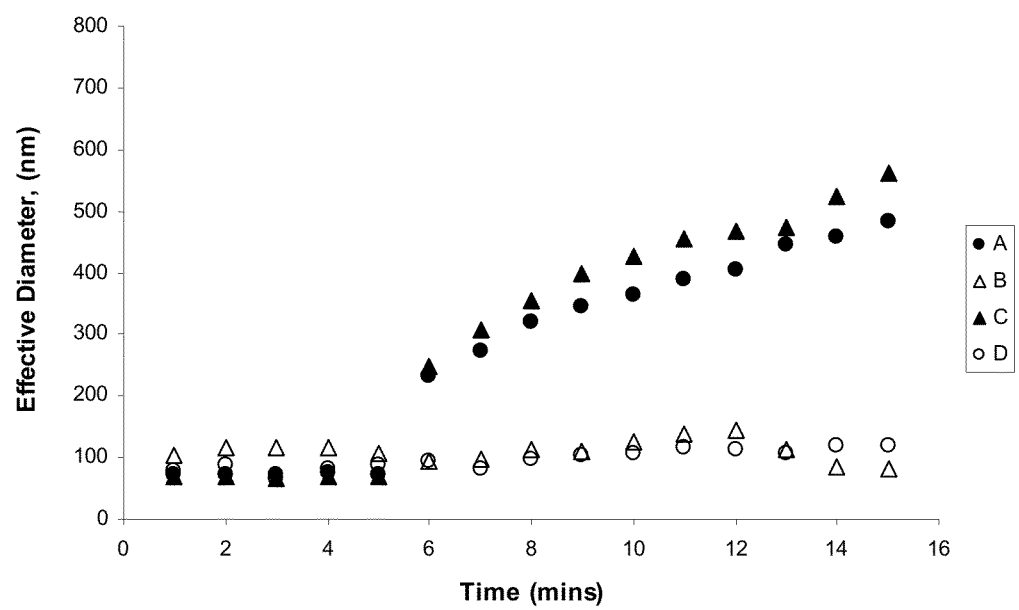
FIG. 7 shows the salt stability of BA-PEGylated MAP-Plasmid Nanoparticles according to an embodiment herein disclosed. Plot A: 5:1 BA-PEG+np+1×PBS after 5 mins; Plot B: 5:1 BA-PEG+np, dialyzed 3×w/100 kDa+1×PBS after 5 mins; Plot C: 5:1 prePEGylated w/BA-PEG+1×PBS after 5 mins; Plot D: 5:1 prePEGylated w/BA-PEG, dialyze 3×w/ 100 kDa+PBS after 5 mins.

As diagrammed in FIG. 2, 2 μg of plasmid DNA in DNAse and RNASe free water (0.45 μg/μL, 4.4 μL) was diluted to 80 μL in DNAse and RNASe free water. This plasmid solution was mixed with 4.89 μg of MAP (0.5 μg/μL, 9.8 μL) also diluted to 80 μL in DNAse and RNASe free water to give a 3+/− charge ratio and a final plasmid concentration of 0.0125 μg/μL. The resulting mixture was incubated for 30 minutes at room temperature. To this solution was added 480 μg of boronic acid PEG$_{5K}$, (compound 6; Example 6), (20 μg/μL, 24 μL). This mixture was then incubated further for 30 minutes, dialyzed twice in DNAse and RNASe free water with a 0.5 mL 100,000 MWCO membrane (BIOMAX, Millipore Corporation) and reconstituted in 160 μL of DNAse and RNASe free water. Half of the solution was diluted with 1.4 mL of 1 mM KCl for zeta potential measurements (FIG. 6). Note that the zeta potential of the BA containing nanoparticles show a lower zeta potential than the nanoparticles that do not. These results support the conclusion that the BA containing nanoparticles have the BA localized on the exterior of the nanoparticles. The other half was used to measure the particle size. The particle size was measured every minute for 5 minutes after which, 10.2 μL of 10×PBS was added such that the final 90.2 μL solution was in 1×PBS. The particle size was then measured again every minute for another 10 minutes as shown in FIG. 7. The BA containing nanoparticles separated from non-particle components (by filtration) are stable in PBS while the particles without the BA are not. These data support the conclusion that the BA containing nanoparticles have the BA localized on their exterior as they are stabilized against aggregation in PBS.

Example 13

Transfection of MAP/pDNA Particles into HeLa Cells

Figure 8:
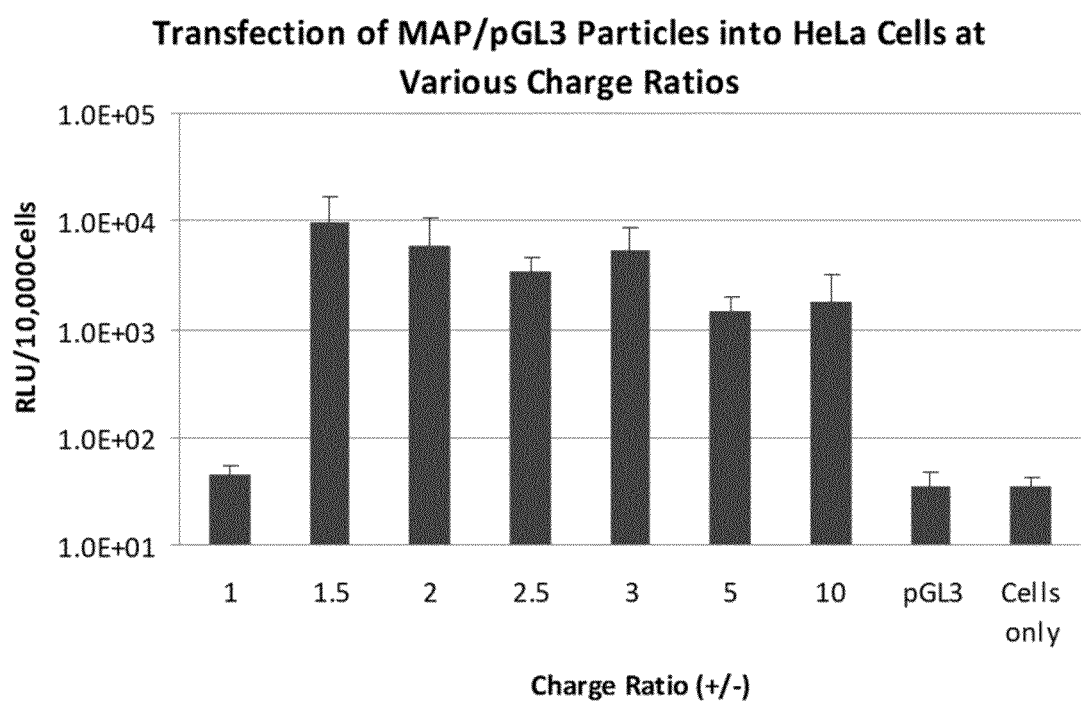
FIG. 8 shows delivery of an agent to human cells in vitro with nanoparticles according to an embodiment herein described. In particular.
Figure 9:
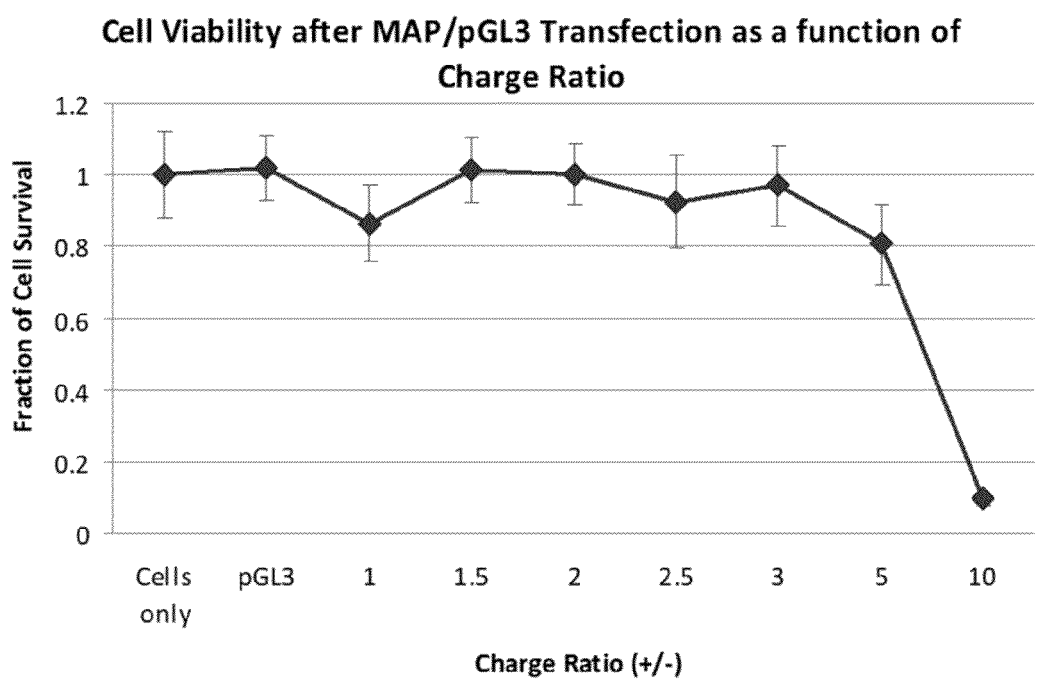
FIG. 9 shows delivery of an agent to a target with nanoparticles according to an embodiment herein described. In particular.

HeLa cells were seeded at 20,000 cells/well in 24 well plates 48 h prior to transfection and grown in medium supplemented with 10% FBS. MAP particles were formulated to contain 1 μg of pGL3 in 200 μL of Opti-MEM I at various charge ratios of polymer to pDNA (refer to Example 9). Growth medium was removed, cells washed with PBS and the particle formulation was added. The cells were subsequently incubated at 37° C. and 5% $CO_2$ for 5 h before the addition of 800 μL of growth medium supplemented with 10% FBS. After 48 h of incubation, a fraction of the cells were analyzed for cell viability using an MTS assay. The remaining cells were lysed in 100 μL of 1× Luciferase Cell Culture Lysis Reagent. Luciferase activity was determined by adding 100 μL of Luciferase Assay Reagent to 10 ul of cell lysate and bioluminescence was quantified using a Monolight luminometer. Luciferase activity is subsequently reported as relative light units (RLU) per 10,000 cells. Results are shown in FIG. 8 and FIG. 9.

Example 14

Co-Transfection of MAP/pDNA and/or siRNA Particles into HeLa Cells

Figure 10:
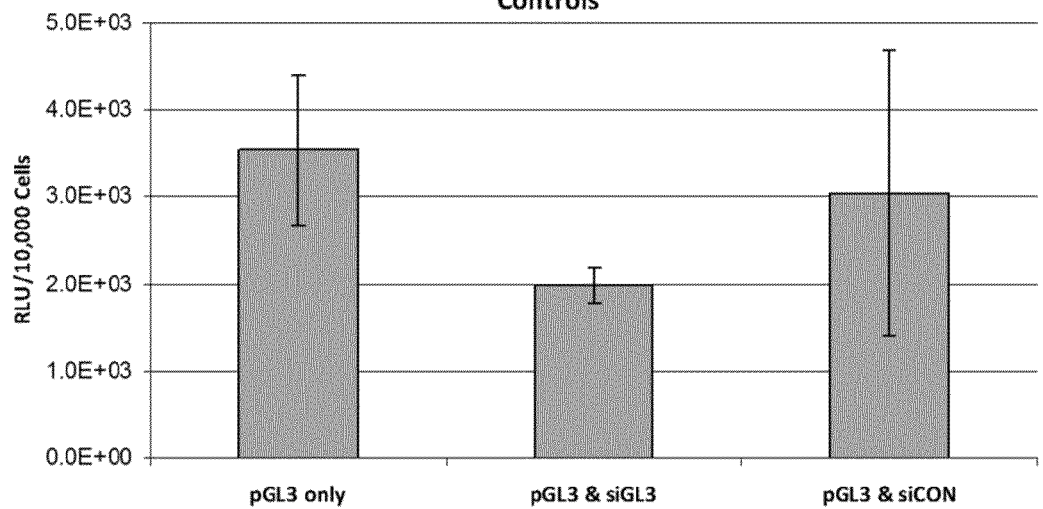
FIG. 10 shows delivery of multiple compounds to a target with nanoparticles according to an embodiment herein described. In particular.

HeLa cells were seeded at 20,000 cells/well in 24 well plates 48 h prior to transfection and grown in medium supplemented with 10% FBS. MAP particles were formulated to contain 1 μg of pGL3 and 50 nM of siGL3 in 200 μL of Opti-MEM I at a charge ratio of 5+/−. Particles containing only pGL3 or pGL3 and siCON were used as controls. Growth medium was removed, cells washed with PBS and the particle formulation was added. The cells were subsequently incubated at 37° C. and 5% $CO_2$ for 5 h before the addition of 800 μL of growth medium supplemented with 10% FBS. After 48 h of incubation, the cells were assayed for Luciferase activity and cell viability as described in Example 12. Results are shown in FIG. 10. Since the RLU is lowered in transfections with the siGL3 (correct sequence), both the siGL3 and the pGL3 must be co-delivered.

Example 15

Transfection of MAP/siGL3 into HeLa-LUC Cells

Figure 11:
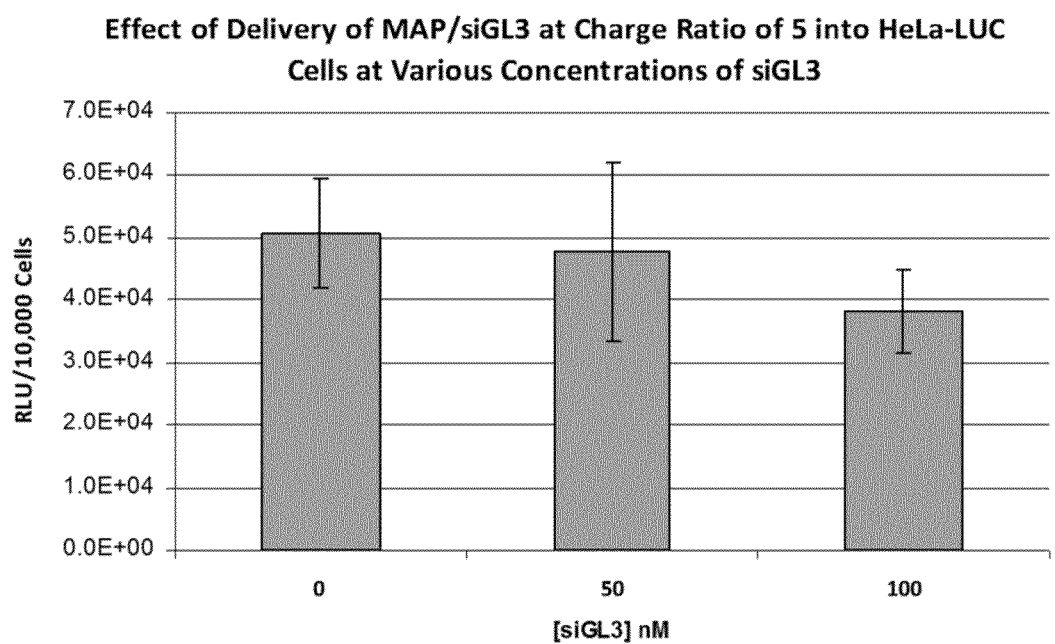
FIG. 11 shows delivery of a compound to a target with nanoparticles according to an embodiment herein described. In particular.

HeLa-LUC cells (contain gene encoding for the firefly luciferase protein) were seeded at 20,000 cells/well in 24 well plates 48 h prior to transfection and grown in medium supplemented with 10% FBS. MAP particles were formulated to contain 50 and 100 nM siGL3 in 200 μL of Opti-MEM I at a charge ratio of 5+/−. Growth medium was removed, cells were washed with PBS and the particle formulation was added. The cells were subsequently incubated at 37° C. and 5% $CO_2$ for 5 h before the addition of 800 μL of growth medium supplemented with 10% FBS. After 48 h of incubation, the cells were assayed for Luciferace activity and cell viability as described in Example 12. Results are shown in FIG. 11. Since the RLUs decline with increasing concentration of siGL3, these data suggest that inhibition of an endogenous gene can occur.

Example 16

Synthesis of Mucic Acid Diiodide, (10)

1 g (2.7 mmol) of mucic acid diamine (Example 3) was mixed with 3.8 mL (27.4 mmol) of triethylamine and 50 mL of anhydrous DMF prior to the dropwise addition of 1.2 mL (13.7 mmol) iodoacetylchloride in a 250 mL round bottom flask. This mixture was allowed to react overnight under constant stirring at room temperature. The solvent was subsequently removed by vacuum pump, the product filtered, washed with methanol and dried under vacuum to yield 0.8 g (1.3 mmol, 46%) of mucic acid diiodide. $^1$H NMR ((CD$_3$)$_2$SO) δ 8.20 (s 2H), 2H), 7.77 (s, 2H), 4.11 (m, 2H), 4.03 (m, 2H), 3.79 (m, 2H), 3.11-3.17 (m, 2H), 1.78 (d, 2H). ESI/MS (m/z): 652.8 [M+Na]$^+$

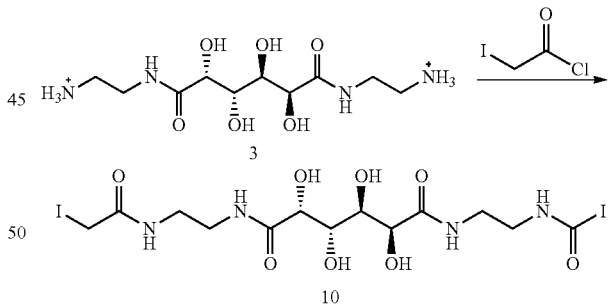

Example 17

Synthesis of Mucic Acid Dicysteine, (11)

To 7 mL of 0.1 M degassed sodium carbonate was added 17 mg of L-cysteine and 0.4 g of mucic acid diiodide. The resulting suspension was brought to reflux at 150° C. for 5 h until the solution turned clear. This mixture was then cooled to room temperature and adjusted to pH 3 via 1 N HCl. Slow addition of acetone was then employed for product precipitation. After filtration, washing with acetone and vacuum drying, 60 mg of crude product was obtained.

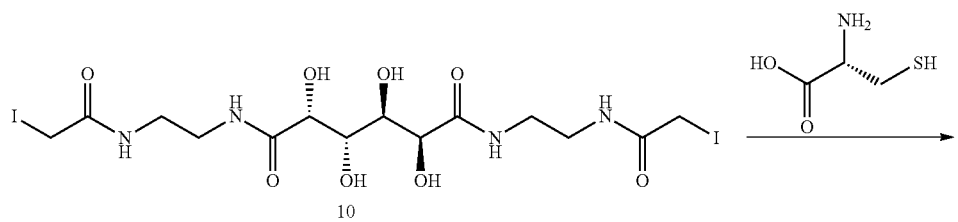

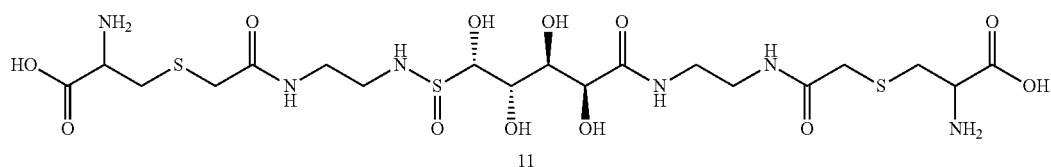

Example 17

Synthesis of Mucic Acid Dicysteine, (11)

To 20 mL of 0.1 M degassed sodium phosphate buffer at pH 7.5 in a 50 mL round bottom flask was added 0.38 g of L-cysteine (3.2 mmol) and 0.40 g (0.6 mmol) of mucic acid diiodine. The resulting suspension was allowed to reflux at 75° C. overnight, cooled to room temperature and lyophilized. 80 mL of DMF was subsequently added to this lyophilized light brown powder and separation of the insoluble excess reagent and phosphate salts from the soluble product was achieved by filtration. DMF was removed under reduced pressure and the product was vacuum dried to give 12 mg (0.02 mmol, 3%) of mucic acid dicysteine.

Example 18

Polymer Synthesis, (Poly(Mucic Acid-DiCys-PEG)) (12)

12 mg (21.7 μmol) of mucic acid dicysteine and 74 mg (21.7 μmol) of PEG-DiSPA 3400 were dried under vacuum prior to the addition of 0.6 mL of anhydrous DMSO under argon in a 2 neck 10 mL round bottom flask. After 10 min of stirring, 9 μL (65.1 μmol) of anhydrous DIEA was transferred to the reaction vessel under argon. This mixture was stirred under argon overnight. The polymer containing solution was then dialyzed using a 10 kDa membrane centrifugal device and lyophilized to yield 47 mg (58%) of Poly(Mucic Acid-DiCys-PEG).

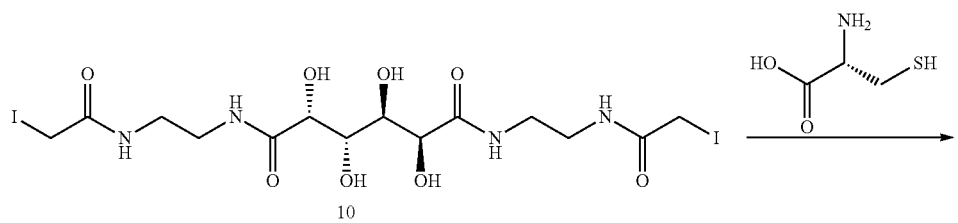

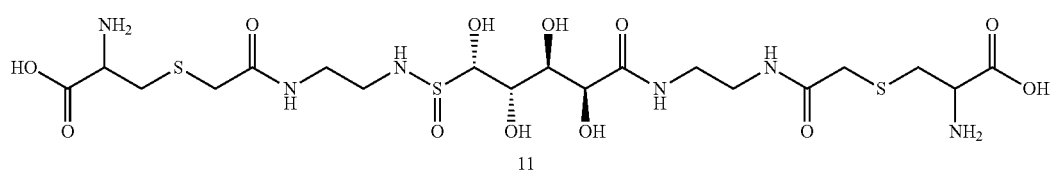

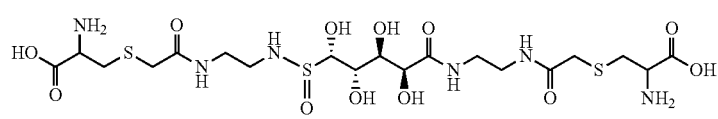
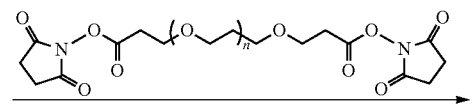

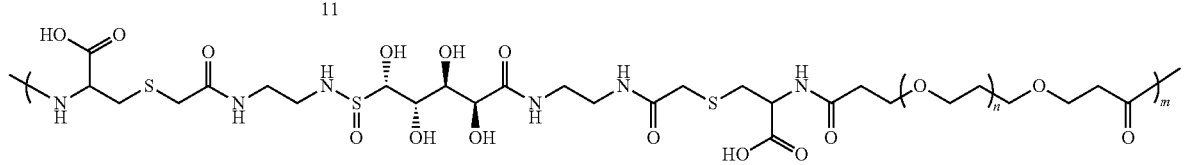

This polymer containing polyols is an anionic AB polymer.

Example 19

Covalent Attachment of Drug (Camptothecin, CPT) to Mucic Acid Polymer, (13)

10 mg (2.7 µmol of repeat units) of Poly(Mucic Acid-DiCys-PEG) was dissolved in 1.5 mL of anhydrous DMSO in a glass jar. After stirring for 10 min, 1.1 µL of DIEA (6.3 µmol), 3.3 mg (6.3 µmol) of TFA-Gly-CPT, 1.6 mg (8.1 µmol) of EDC and 0.7 mg (5.9 µmol) of NHS were added to the reaction mixture. After stirring for 8 hrs, 1.5 mL of ethanol was added and the solvents were removed under reduced pressure. The precipitate was dissolved in water and insoluble materials were removed by filtration through a 0.2 µm filter. The polymer solution was then dialyzed against water via a 10 kDa membrane and subsequently lyophilized to give the Poly (Mucic Acid-DiCys-PEG)-CPT conjugate.

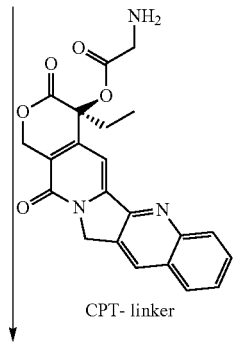

CPT-linker

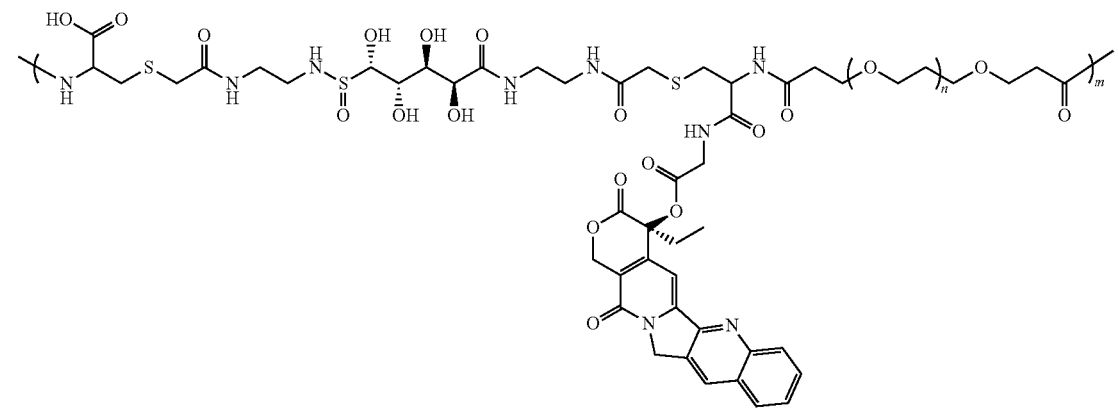

Example 20

Formulation of Nanoparticle with CPT-Mucic Acid Polymer (13) in Water, (20)

The Effective diameters of poly(Mucic Acid-DiCys-PEG) and poly(Mucic Acid-DiCys-PEG)-CPT conjugate were measured by formulating the polymers in double distilled water (0.1-10 mg/mL) and evaluated via dynamic light scattering (DLS) using a ZetaPALS (Brookhaven Instrument Co) Instrument. 3 successive runs of 1 min each were subsequently recorded and averaged. The zeta potentials of both compounds was measured in a 1.1 mM KCl solution using a ZetaPALS (Brookhaven Instrument Co) Instrument. 10 successive automated runs at target residuals of 0.012 were then performed and results averaged (FIG. 14). In particular, there two distributions were measured for the poly(Mucic Acid-DiCys-PEG)-CPT conjugate the predominant distribution was a 57 nm (60% of the total particle population). A second minor distribution was also was measured at 233 nm.

Example 21

Formulation of Boronic Acid-PEGylated Nanoparticle with CPT-Mucic Acid Polymer (13) and Boronic Acid-Disulfide-PEG$_{5000}$ 6 in Water The boronic acid PEGylated poly(Mucic Acid-DiCys-PEG)-CPT nanoparticle is formulated by dissolving the polymer in double distilled water at a concentration of 0.1 mg/mL followed by the addition of Polymer 6 (BA-PEG) also in water, such that the ratio of PBA-PEG to the diols on the mucic acid sugar in the poly(Mucic Acid-DiCys-PEG)-CPT conjugate is 1:1. The mixture is incubated for 30 mins after which the effective diameter and zeta potential are measured using a ZetaPALS (Brookhaven Instrument Co) instrument.

Example 22

Targeted Nanoparticles for pDNA Delivery in Mice

The plasmid pApoE-HCRLuc contains the gene to express luciferase and is under the control of a liver specific promoter. Polymer (MAP) 4 (0.73 mg), polymer 6 (73 mg) and polymer 9 (0.073 mg) were combined in 5 mL of water and then 1.2 mL of water containing the pApoE-HCRLuc plasmid were added (gives a charge ratio of polymer 4 to the plasmid of +3). The particles were placed in D5W (5% glucose in water) by successive spin filtering with subsequent additions of D5W (starting from the initial formulation that was in water). Nude mice were implanted with Hepa-1-6 liver cancer cells and tumors were allowed to grow until a size of approximately 200 mm$^3$. Injections of the targeted nanoparticles were done i.v. in the tail vein at an amount equal to 5 mg plasmid/kg mouse. The mice were imaged 24 hours after the injections. The mice showed no signs of toxicity and there was luciferase expression detected in the region of the tumor and not in the region of the liver.

Example 23

Synthesis of PBA-PEG and nitroPBA-PEG and Determination of pKa

To prepare a stabilized and targeted nanoparticle, the covalent, reversible binding property between boronic acids and MAP (diol containing) was used. The pKa of phenylboronic acid (PBA) is high at 8.8. To decrease the pKa, PBAs with electron withdrawing groups on the phenyl ring were employed to increase the acidity of the boron atom. Commercially available 3-carboxyPBA and 3-carboxy 5-nitroPBA were converted into acyl chlorides using oxalyl chloride. These acyl chloride species were then reacted with $NH_2$—PEG to form PBA-PEG and nitroPBA-PEG respectively. The addition of bases DMF and DIPEA were required for the synthesis reactions to proceed. However, the presence of these bases resulted in tetrahedral adduct formations with acidic PBA. To remove these adducts, work up in 0.5 N HCl with subsequent equilibration to neutral pH by dialysis against water was carried out.

For synthesis of PBA-PEG 200 mg (1.21 mM) of 3-carboxyphenylboronic acid dissolved in 5 ml of anhydrous tetrahydrofuran was added 18.7 μl (0.24 mM) of anhydrous dimethylformamide under argon. This reaction vessel was transferred into an ice bath and 195 μl (2.89 mM) of oxalyl chloride was slowly added under argon. The reaction was allowed to proceed under vent and constant stirring for 2 h at room temperature. Solvent and excess reagent were removed under a vacuum. 37 mg (0.2 mM) the resulting dried acyl chloride compound was dissolved in 15 ml of anhydrous dichloromethane under argon. Then 500 mg (0.1 mM) of NH2-PEG5 kDa-CO2H and 52 μl (0.3 mM) of dry DIPEA under argon were added. After overnight reaction under constant stirring, solvent was removed under a vacuum and the dried product was reconstituted in 0.5 N HCl. This solution was passed through a 0.2 μm filter (Acrodisc®) and dialyzed against water with a 3 kDa MWCO membrane filter device (Amicon™) until constant pH was attained. The supernatant was then filtered with a 0.2 μm filter (Acrodisc®) and lyophilized to yield 377 mg (73%) of PBA-PEG-CO2H. 1H NMR ((CD3)2SO) δ 12.52 (s, 1H), 8.39 (t, 1H), 8.22 (s, 1H), 8.14 (s, 2H), 7.88 (d, 1H), 7.82 (d, 1H), 7.39 (t, 1H), 3.99 (s, 2H), 3.35-3.62 (PEG peak). MALDI-TOF (m/z): 5600 g/mol (NH2-PEG5 kDa-CO2H, 5400 g/mol).

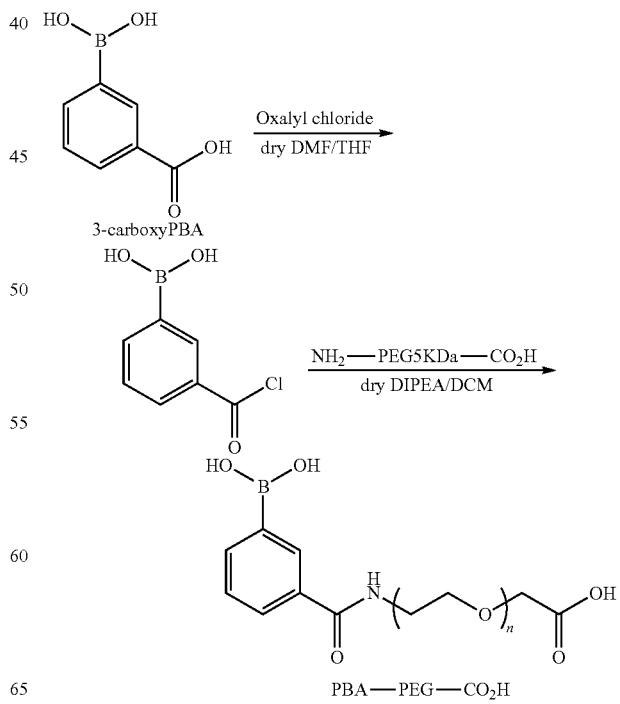

Synthesis of nitroPBA-PEG-CO2H was performed in the same way as for PBA-PEG-CO2H except the starting material was 3-carboxy 5-nitrophenylboronic acid. The reaction yielded 393 mg (76%) of nitroPBA-PEG-CO2H. 1H NMR ((CD3)2SO) δ 12.52 (s, 1H), 8.89 (t, 1H), 8.72 (s, 1H), 8.68 (s, 1H), 8.64 (s, 1H), 8.61 (s, 2H), 3.99 (s, 2H), 3.35-3.62 (PEG peak). MALDI-TOF (m/z): 5600 g/mol (NH2-PEG5 kDa-CO2H, 5400 g/mol).

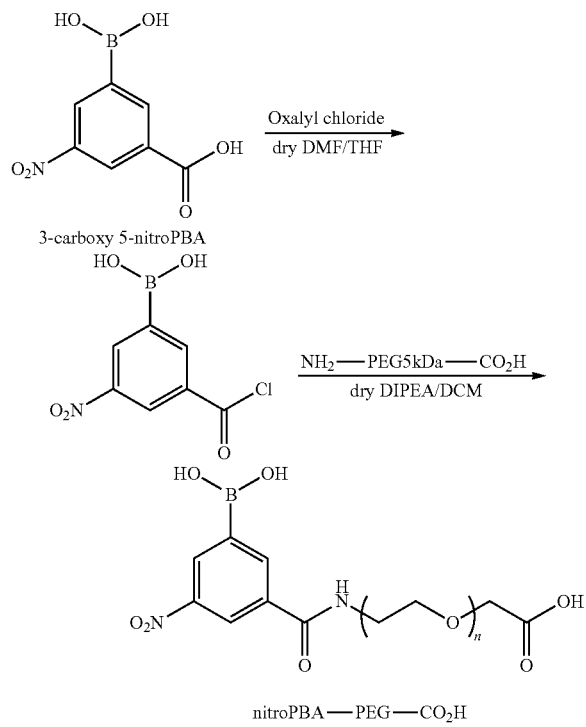

The pKa of the synthesized PBA compounds were found by measuring the change in absorbance of PBA as it converted from trigonal (in low pH) to tetrahedral (in high pH) conformation. To a solution of 10-3 M PBA in 0.1 M PBS, pH 7.4 was titrated 1 N NaOH. pH was recorded and corresponding samples were removed for absorbance measurements at 268 nm.

TABLE 2 pKa and binding constants of PBA compounds

| Compound | pKa | Binding constant with MAP (M$^{-1}$) |
|---|---|---|
| PBA | 8.8 | 20 |
| PBA-PEG-CO$_2$H | 8.3 | 520 |
| nitroPBA-PEG-CO$_2$H | 6.8 | 1420 |

Example 24

Antibody Conjugation to nitroPBA-PEG

Following production of nitroPBA-PEG the resulting compound was conjugated to an antibody. For conjugation 36 mg (6.4 µM) of nitroPBA-PEG-CO2H, 12.3 mg (64 µM) of 1-ethyl-3-(3-dimethylaminopropyl)carbodiimide (EDC) and 11.1 mg (96 µM) of NHS were dissolved in 2.4 ml of 0.1 M MES buffer, pH 6.0. This mixture was reacted for 15 min on a rotating shaker at room temperature. Excess reactants were dialyzed away with 3 kDa molecular weight cutoff membrane filter device (Amicon™). This activated carboxylic acid PEG compound was added to 20 mg (0.14 mM) of human IgG1 antibody (Herceptin®) in 0.1 M PBS, pH 7.2. The reaction was carried out on a rotating shaker at room temperature for 2 h and then dialyzed 4 times using a 50 kDa molecular weight cutoff membrane filter device (Amicon™) against 1×PBS at pH 7.4. Analysis of the conjugate by mass spectrometry (MALDI-TOF) showed an average conjugation of 1 to 2 nitroPBA-PEG compounds per antibody.

Example 26

Formation and Characterization of Targeted MAP Nanoparticles

The effect of PBA-PEG and nitroPBA-PEG on nanoparticle formation and stability were examined. A solution of PBA-PEG was added to a solution of MAP at 3+/− charge ratio (positive charge from MAP for every negative charge from siRNA) in phosphate buffer at pH 7.4. This mixture was allowed to sit at room temperature for 10 min for the complexation of PBA-PEG with the diol-containing MAP. This was then added to an equal volume of siRNA in water and mixed by pipetting. After 10 min, tests and characterizations were performed. The formulations of particles stabilized with nitroPBA-PEG and at different charge ratios were conducted in the same manner. The conjugation of PBA-PEG formed MAP/siRNA particles of 150-300 nm in size. MAP-4 (indicating 4 methylene units between charge center (amidine) and binding site (polyol)) resulted in smaller nanoparticles than when MAP-2 was used. However, upon the addition of salt, all particles aggregated indicating that PBA-PEG was incapable of providing sufficient stability to the nanoparticles. When nitroPBA-PEG was used, particles at all charge ratios tested, 1 and 3 (+/−), demonstrated stabilized nanoparticles. The difference in particle stability conferred by PBA-PEG and nitroPBA-PEG indicates the importance of modifying the PEGylated boronic acid compounds to possess stronger binding to polyols.

For siRNA condensed with MAP-4 without the presence of stabilizing agent PEG, a particle size of 640 nm was observed with a high zeta potential of +32 mV. When nitroPBA-PEG was added to stabilize the particle, the diameter reduced to 130 nm with a negative surface charge of −4 mV. This negative charge is a result of the binding between boronic acid and diols. When 0.25 mol % IgG (Herceptin®) conjugated nitroPBA-PEG was introduced, interestingly the particle size reduced further to 82 nm while the zeta potential remained similar.

Figure 16:
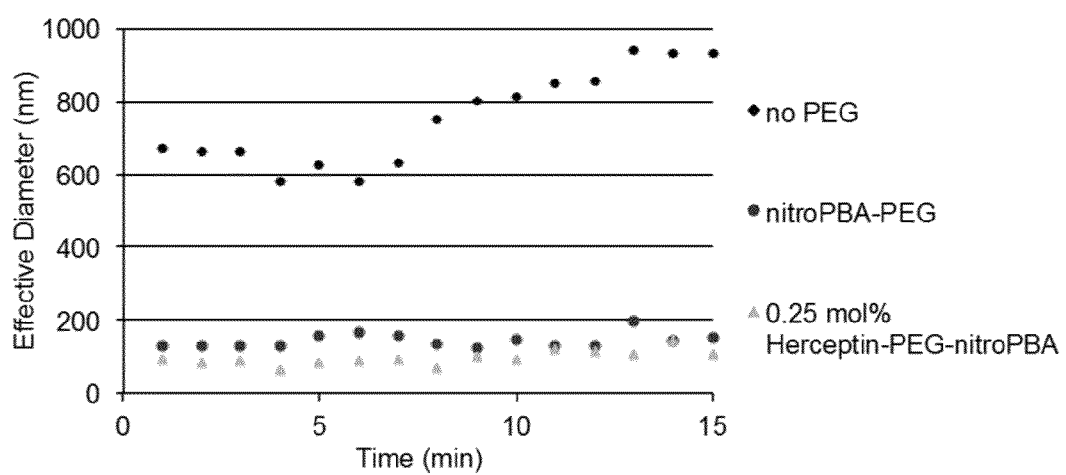
FIG. 16 shows salt stability of MAP-4/siRNA stabilized with no PEG, nitroPEG-PEG and with 0.25 mol % Herceptin-PEG-nitroPBA. Formulated at charge ratio 3 (+/−), 10×PBS was added at time 5 min such that the resulting solution was at 1×PBS.

The salt stability for MAP-4/siRNA nanoparticles with various PEG groups attached was assessed. Particle size was recorded for 5 runs at 1 min using a zeta potential analyzer (DLS ZetaPALS instrument, Brookhaven Instruments, Holtsville, N.Y.). Measurement was stopped to allow the addition of a 10×PBS solution to the particle formulation such that the resulting particle formulations contain 1×PBS. Measurements were subsequently restarted and 10 successive runs of 1 min each were recorded to study the effect of salt addition on particle stability. As shown in FIG. 16, without the presence of a stabilizing agent PEG, the particles aggregated. When nitroPBA-PEG was present, particles remained stable in salt conditions.

Example 27

Formation and Characterization of Targeted MAP-CPT Nanoparticles

To prepare a targeted MAP-CPT nanoparticle, the covalent, reversible binding property between boronic acids and MAP (diol containing) was used. The binding constant between PBA and MAP is low at about 20 $M^{-1}$. To increase the binding constant, PBAs with electron withdrawing groups on the phenyl ring were employed to increase the acidity of the boron atom and thus elevate the binding constant with MAP. Commercially available 3-carboxyPBA and 3-carboxy 5-nitroPBA were converted into acyl chlorides using oxalyl chloride. These acyl chloride species were then reacted with $NH_2$-PEG-$CO_2H$ to form PBA-PEG-$CO_2H$ and nitroPBA-PEG-$CO_2H$, respectively. The addition of bases DMF and DIPEA were required for the synthesis reactions to proceed. However, the presence of these bases resulted in tetrahedral adduct formations with acidic PBA. To remove these adducts, work up in 0.5 N HCl with subsequent equilibration to neutral pH by dialysis against water was carried out.

pKa values of the modified PBAs were determined by absorbance changes due to conformational change of PBA from trigonal to tetrahedral form as the pH was increased (Table 2). PBA with electron withdrawing groups resulted in lower pKa's, with nitroPBA-PEG-$CO_2H$ having the lowest pKa of 6.8. Thus, at physiological pH, most of the PBA was present in the reactive anionic tetrahedral form. Binding constants between PBA and MAP were found by competitive binding with Alizarin Red S in 0.1 M PBS, pH 7.4. Because of the low pKa value and high binding constant with MAP observed for nitroPBA-PEG-$CO_2H$, it was chosen as the linker between IgG (Herceptin®) and MAP-CPT nanoparticles.

The conjugation reaction between IgG (Herceptin®) and nitroPBA-PEG-$CO_2H$ proceeded via EDC coupling (described above). An average of 1 to 2 PEGs were attached per IgG (Herceptin®) antibody.

TABLE 3

Characterization of MAP, MAP-CPT conjugate, MAP-CPT nanoparticles and targeted MAP-CPT nanoparticles

|  |  | Short | Medium | Long |
|---|---|---|---|---|
| MAP | Base added (equivalent)[a] | 1.1 | 1.6 | 2 |
|  | MW[b] (kDa) | 20 | 65 | 102 |
|  | Polydispersity[c] | 1.22 | 1.36 | 1.13 |
|  | # repeat units (n) | 5-7 | 15-21 | 25-30 |
| MAP-CPT conjugate | MW[b](kDa) | 22 | 75 | 114 |
|  | wt % CPT conjugated | 9.8 | 12.7 | 10.1 |
| MAP-CPT nanoparticle | # conjugates/particle | 2-3 | 2-3 | 2-3 |
|  | # CPT/particle | ~14 | ~60 | ~72 |
|  | particle size (nm) | ~30 | ~30 | ~30 |
|  | zeta potential (mV) | -1.3 +/- 0.6 | -0.5 +/- 0.5 | -0.8 +/- 0.5 |
| Targeted MAP-CPT nanoparticle | # Herceptin/particle |  | 1 |  |
|  | particle size (nm) |  | ~40 |  |
|  | zeta potential (mV) |  | -0.4 +/- 0.6 |  |

[a]Equivalent amount of N,N-diisopropylethylamine (DIPEA) added per amine group in mucic acid di(Asp-amine).
[b]MW, molecular weight determined as (Mw + Mn)/2; Mw, weight average molecular weight; Mn, number average molecular weight.
[c]Polydispersity determined as Mw/Mn.

An average size of about 40 nm was observed for targeted MAP-CPT nanoparticles by DLS and cryo-EM (Table 3). This increase in about 10 nm from the non-targeted nanoparticle suggests the attachment of IgG (Herceptin®) to the nanoparticle (the amount was about one Herceptin® antibody per nanoparticle). Indeed, from cryo-EM images, the targeted nanoparticles were not spherical but appeared to have protrusions indicating the attachment of antibodies. The surface charge of targeted MAP-CPT nanoparticles was slightly higher than MAP-CPT nanoparticles due to the presence of a positively charged Herceptin at pH 7.4 (pI of Herceptin®, 9.2).

Example 28

Cellular Uptake Studies

A HER2 overexpressing human breast cancer cell line (BT-474), was used to examine the cellular uptake of Herceptin® targeted MAP-CPT nanoparticles versus the non-targeted nanoparticles. A HER2 negative breast cancer cell line (MCF-7), was used as a negative control. For these studies 24 well plates were seeded with either BT-474 (in RPMI-1640 medium supplemented with 10% fetal calf serum) or MCF-7 (in Dulbecco's Modified Eagle medium supplemented with 10% fetal calf serum) (Cellgro, Manassas, Va.) at 20,000 cells per well and kept at 37° C. in a humidified oven with 5% $CO_2$. After 40 h, media were replaced with 0.3 ml of fresh media containing either medium MAP-CPT (40 µg CPT/ml), medium MAP-CPT with free Herceptin® at 10 mg/ml, targeted MAP-CPT (40 µg CPT/ml) at varying targeting densities or targeted MAP-CPT with free Herceptin® at 10 mg/ml. Transfection was conducted for 30 min at 37° C. Formulations were then removed and cells washed twice with cold PBS. 200 µl of RIPA buffer was added per well for cell detachment and lysis. Lysed cells were then incubated at 4° C. for 15 min and centrifuged at 14,000 g for 10 min at 4° C. A portion of the supernatant was used for protein quantification via BCA assay. To another portion was added an equal amount of 0.1 N NaOH, this was incubated at room temperature overnight and fluorescence was measured at 370/440 nm using known concentrations of MAP-CPT as standard.

Figure 17:
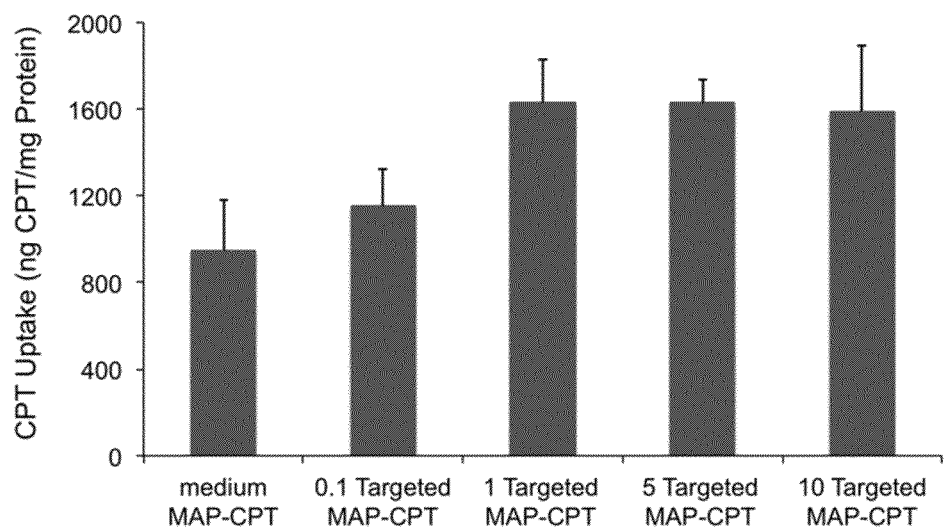
FIGS. 17A and 17B show cellular uptake of (A) targeted MAP-CPT nanoparticles at increasing ratio of Herceptin®-PEG-nitroPBA to nanoparticle in BT-474, (B) medium MAP-CPT nanoparticles or targeted MAP-CPT nanoparticles with or without free Herceptin® (10 mg/ml) in BT-474 (shaded bars) and MCF-7 (open bars) cell lines.
Figure 17:
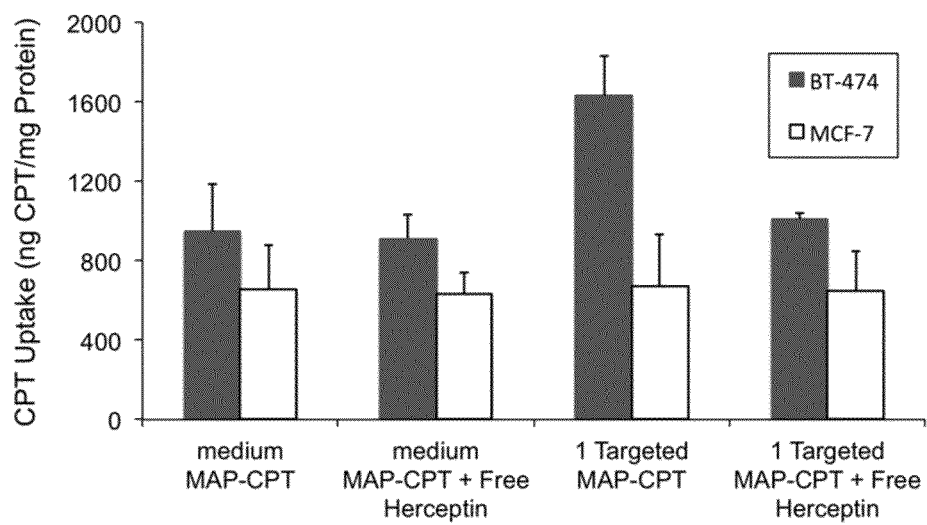

It was observed that one Herceptin®-PEG-nitroPBA per nanoparticle was sufficient to achieve about 70% greater uptake in BT-474 cell line compared to the non-targeted nanoparticle (FIG. 17A). Uptake of the targeted MAP-CPT in BT-474 cells showed inhibition in the presence of free Herceptin® (FIG. 17B). In contrast, uptake of MAP-CPT nanoparticles in MCF-7 exhibited no dependence on targeting or on presence of free Herceptin® (FIG. 2B). These data indicate that there is receptor mediated uptake in the BT-474 cells by the targeted MAP-CPT nanoparticles via engagement of the HER2 receptor. Cellular uptake of both the targeted and non-targeted MAP-CPT nanoparticles also occurred via non-specific fluid phase endocytosis.

Example 29

In Vitro Release Studies

Experiments were conducted to assess the release of CPT from short, medium, long MAP-CPT nanoparticles and targeted MAP-CPT nanoparticles. These studies were conducted using 0.32 mg CPT/ml in 1×PBS at pH 6.5, 7 or 7.4; BALB/c mice plasma, human plasma, and 1×PBS at pH 7.4 containing 3 mg/ml of low density lipoprotein (LDL), or 100 units/ml of Butyrylcholinesterase (BCHE) or a combination of LDL and BCHE.

Media pipetted into 96 well plates were incubated at 37° C. in a humidified oven for 2 h for equilibration. Formulations were mixed into the relevant media and placed back into the oven. Samples were taken out at predetermined time points and immediately frozen at −80° C. until time for analysis. For release in BALB/c mice plasma and in human plasma, incubation was carried out in a humidified oven at 37° C. with 5% $CO_2$ to maintain the carbonic acid/bicarbonate buffer system, the major pH buffer system in plasma at physiological pH levels.

The amount of unconjugated CPT was determined by first mixing 10 μl of sample with 10 μl of 0.1 N HCl and incubating at room temperature for 30 min. 80 μl of methanol was then added and the mixture incubated at room temperature for 3 h for protein precipitation. This mixture was centrifuged at 14,000 g for 10 min at 4° C., supernatant was filtered with a 0.45 μm filter (Millex-LH), diluted 20 folds with methanol and 10 μl of the resulting solution injected into HPLC. The peak area of the eluted CPT (at 7.8 min) was compared to that of control. To measure the total amount of CPT, 10 μl of sample was mixed with 6.5 μl of 0.1 N NaOH. This solution was incubated at room temperature for 1 h for CPT to be released from parent polymer. 10 μl of 0.1 N HCl was then added to convert the carboxylate CPT form to the lactone form. 73.5 μl of methanol was subsequently added and mixture incubated for 3 h at room temperature. The sample was then centrifuged and processed as above. Polymer-bound CPT concentration was determined from the difference between total CPT and unconjugated CPT concentrations.

Release of CPT from the short, medium and long MAP-CPT nanoparticles and from the targeted MAP-CPT nanoparticles all exhibited first-order kinetics. Release half-lives of CPT from the short, medium and long MAP-CPT nanoparticles were very similar in all conditions tested, while longer half-lives for the targeted MAP-CPT were observed (Table 4). A strong dependence of release rate with pH was observed. As the pH increased from 6.5 to 7.4, the release half-lives reduced from 338 h to 58 h for the short, medium and long MAP-CPT nanoparticles. These data indicate that hydrolysis plays an important role in the release of CPT. A release half-life of 59 h was observed in BALB/c mice plasma, while a significantly lower half-life of 38 h was obtained in human plasma for the short, medium and long MAP-CPT nanoparticles. It is known that mice plasma contains more esterase activity than human plasma, while human plasma contains more "fat" than mouse plasma. Therefore, to understand the differences in release rates between human and mice plasma, the contributions of esterase and fat to CPT release rates were individually tested. Butyrylcholinesterase (BCHE) is present in both mice and human plasma and was used to test esterase contribution to the release rate. Low density lipoprotein (LDL) was chosen to test the contribution of "fat" to the release rate. These components were constituted in PBS (pH 7.4). It was found that the presence of BCHE did not affect release rate (half-life of 61 h compared to 58 h in PBS, pH 7.4, for the short, medium and long MAP-CPT nanoparticles). However, the addition of LDL dramatically increased the release rates. This effect is likely due to nanoparticle disruption by competing hydrophobic interactions. Therefore, nanoparticle disruption by the presence of "fat", and the subsequent CPT cleavage by hydrolysis appear to be another main mechanism of CPT release from MAP-CPT nanoparticles. In vitro release from the Herceptin® targeted MAP-CPT nanoparticles shows longer half-lives than the non-targeted versions. It is possible that the presence of Herceptin® with a pI of 9.2 increased the stability of the negatively charged nanoparticles by electrostatic interactions, and thus shielded the nanoparticles from some of the competing hydrophobic interactions.

TABLE 4

In vitro release half-lives ($t_{1/2}$) of CPT from short, medium and long MAP-CPT nanoparticles and from targeted MAP-CPT nanoparticles in various media

| PBS | $t_{1/2}$(h) | pH 6.5 | pH 7 | pH 7.4 |
|---|---|---|---|---|
| | Short, medium, long MAP-CPT | 338 | 178 | 58 |
| | Targeted MAP-CPT | 396 | 204 | 78 |
| Plasma | $t_{1/2}$(h) | Mice | Human | |
| | Short, medium, long MAP-CPT | 59 | 38 | |
| | Targeted MAP-CPT | 63 | 46 | |
| PBS pH 7.4 | $t_{1/2}$(h) | $LDL^a$ | $BCHE^b$ | LDL + $BCHE^c$ |
| | Short, medium, long MAP-CPT | 45 | 61 | 44 |
| | Targeted MAP-CPT | 62 | 76 | 62 |

Abbreviations: PBS, phosphate buffered saline; LDL, low density lipoprotein; BCHE, Butyrylcholinesterase.
[a]PBS, pH 7.4, containing 3 mg/ml LDL.
[b]PBS, pH 7.4, containing 100 units/ml BCHE.
[c]PBS, pH 7.4, containing 3 mg/ml LDL and 100 units/ml BCHE.

Example 30

Cytotoxicity Assays

In vitro cytotoxicities of medium MAP, nitroPBA-PEG, CPT, medium MAP-CPT nanoparticles, targeted MAP-CPT nanoparticles and Herceptin® were evaluated in two HER2+ breast cancer cell lines (BT-474, SKBR-3) and two HER2− breast cancer cell lines (MCF-7, MDA-MB-231) (Table 5). For these studies cells were kept at 37° C. in a humidified oven with 5% $CO_2$. BT-474, MCF-7, SKBR-3 and MDA-MB-231 cell lines were incubated in RPMI-1640 medium, Dulbecco's Modified Eagle medium, McCoy's 5A Modified medium and Dulbecco's Modified Eagle medium respectively (all supplemented with 10% fetal calf serum). 3,000 cells per well were plated into 96 well plates. After 24 hours, media was removed and replaced with fresh media containing different concentrations of medium MAP, nitroPBA-PEG, CPT, medium MAP-CPT nanoparticles, targeted MAP-CPT nanoparticles or Herceptin®. After 72 h of incubation, formulations were replaced with fresh media, and 20 μl of CellTiter 96® AQueous One Solution cell proliferation assay (Promega) was added per well. This was incubated for 2 hours in a humidified oven at 37° C. with 5% $CO_2$ before absorbance measurements at 490 nm. Wells containing untreated cells were used as controls.

Medium MAP and nitroPBA-PEG gave $IC_{50}$ values of above 500 μM and 1000 μM (highest concentrations tested), respectively, indicating minimal toxicity. $IC_{50}$ concentrations of CPT, medium MAP-CPT nanoparticles and targeted MAP-CPT nanoparticles were based on the content of the CPT. It is noted that CPT was released gradually from medium MAP-CPT nanoparticles and targeted MAP-CPT nanoparticles (see In Vitro Release Studies). Additionally, nanoparticle uptake by cells results in long release times due to the acidic nature of the endosomes. These factors contribute to the observed higher $IC_{50}$ values for the medium MAP-CPT nanoparticles and targeted MAP-CPT nanoparticles compared to CPT (Table 5). In HER2+ cell lines, the targeted MAP-CPT nanoparticles gave lower $IC_{50}$ values compared to MAP-CPT alone, while in HER2-cell lines, targeting did not affect the $IC_{50}$. BT-474 was the most resistant cell line to CPT, and consequently to medium MAP-CPT nanoparticles. The addition of Herceptin at concentrations of 0.001-0.5 µM to BT-474 or SKBR-3 cells resulted in a constant cell viability of about 60% as compared to a no treatment control. The lack of a true $IC_{50}$ value over this concentration range for these cell lines has been observed previously (Phillips, et al., Cancer Res. 68, 9280-9290 (2008)). There were no effects observed in HER2-cell lines at Herceptin concentrations of up to 0.5 µM.

TABLE 5

$IC_{50}$ values of medium MAP, nitroPBA-PEG, CPT, medium MAP-CPT nanoparticles, targeted MAP-CPT nanoparticles and Herceptin for a range of breast cancer cell lines.

| | | MCF-7 | MDA-MB-231 | SKBR-3 | BT-474 |
|---|---|---|---|---|---|
| HER2 expression | | — | — | + | + |
| $IC_{50}$ (µM) | Medium MAP | >500 | >500 | >500 | >500 |
| | nitroPBA-PEG | >1000 | >1000 | >1000 | >1000 |
| | CPT | 0.3 | 0.1 | 0.03 | 4 |
| | Medium MAP-CPT | 0.5 | 0.6 | 0.2 | 40 |
| | Targeted MAP-CPT | 0.5 | 0.6 | 0.1 | 6 |
| | Herceptin | no effect | no effect | no value[a] | no value[a] |

[a]no value, $IC_{50}$ value was not obtained over the concentration range of 0.001-0.5 µM.

Example 31

Pharmacokinetic Studies

Figure 18:
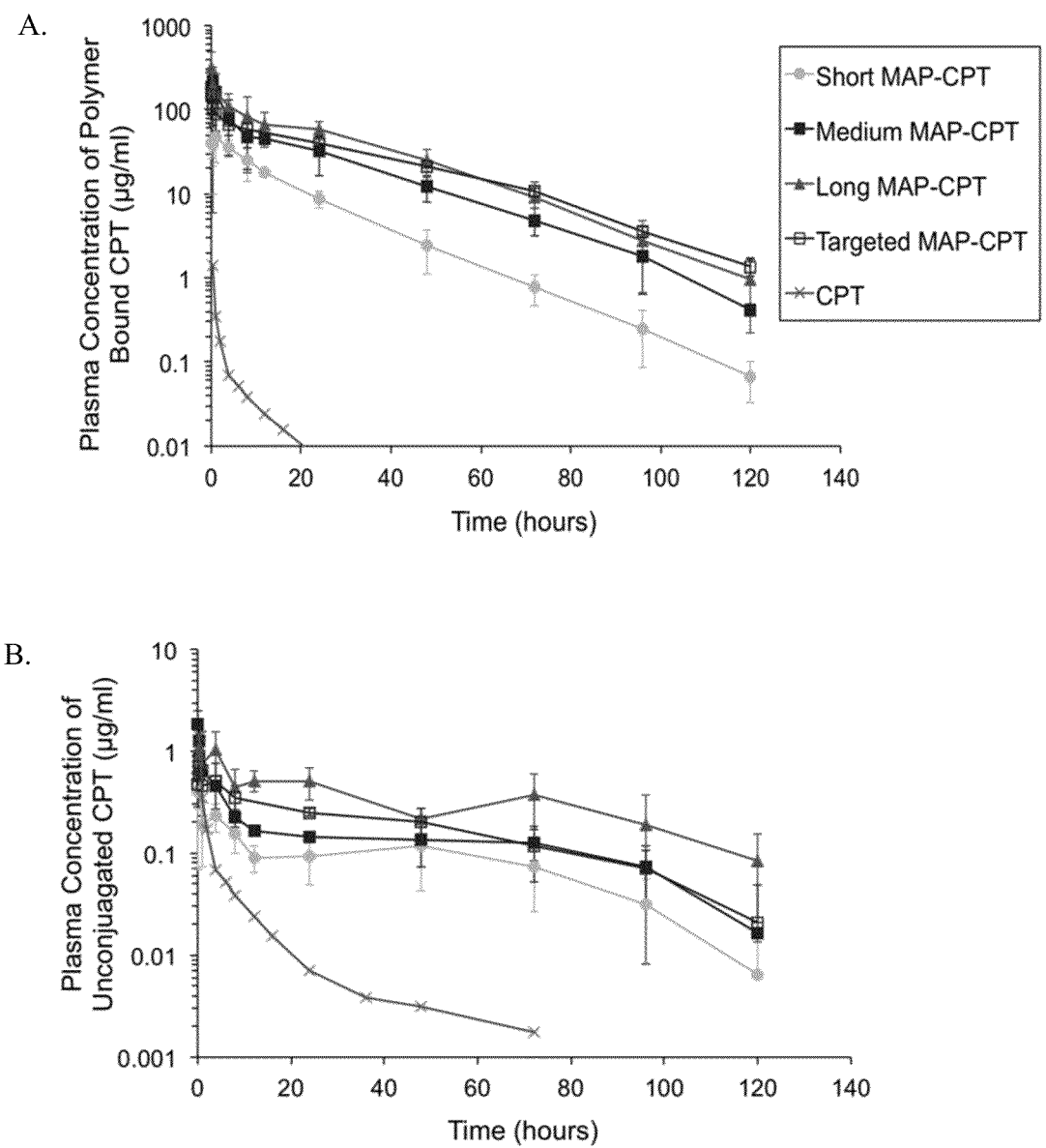
FIGS. 18A and 18B show plasma pharmacokinetics of short, medium and long MAP-CPT nanoparticles and targeted MAP-CPT nanoparticles in BALB/c mice at 10 mg CPT/kg injections. Free CPT injected at 10 mg/kg into CD2F1 mice is shown as comparison. (A) Plasma concentration of polymer bound CPT as a function of time. (B) Plasma concentration of unconjugated CPT as a function of time.

Plasma pharmacokinetic studies of short, medium, long MAP-CPT nanoparticles and targeted MAP-CPT nanoparticles at 10 mg/kg (CPT basis) injections were conducted in female BALB/c mice (FIG. 18). For these studies nanoparticle formulated in 0.9 wt % NaCl (non-targeted nanoparticles) or PBS (targeted MAP-CPT nanoparticles) were administered via bolus tail vein injection into 12-16 weeks old female BALB/c mice. At predetermined time points, blood was collected via saphenous vein bleed with blood collection tubes (Microvette CB 300 EDTA, Sarstedt). Samples were immediately centrifuged at 10,000 g, 4° C. for 15 minutes and supernatant removed and stored at −80° C. until time for analysis. Analyses for unconjugated and polymer-bound CPT were as follows. The amount of unconjugated CPT was determined by first mixing 10 µl of sample with 10 µl of 0.1 N HCl and incubating at room temperature for 30 min. 80 µl of methanol was then added and the mixture incubated at room temperature for 3 h for protein precipitation. This mixture was centrifuged at 14,000 g for 10 min at 4° C., supernatant was filtered with a 0.45 µm filter (Millex-LH), diluted 20 folds with methanol and 10 µl of the resulting solution injected into HPLC. The peak area of the eluted CPT (at 7.8 min) was compared to that of control. To measure the total amount of CPT, 10 µl of sample was mixed with 6.5 µl of 0.1 N NaOH. This solution was incubated at room temperature for 1 h for CPT to be released from parent polymer. 10 µl of 0.1 N HCl was then added to convert the carboxylate CPT form to the lactone form. 73.5 µl of methanol was subsequently added and mixture incubated for 3 h at room temperature. The sample was then centrifuged and processed as above. Polymer-bound CPT concentration was determined from the difference between total CPT and unconjugated CPT concentrations. Non-compartmental modeling software PK Solutions 2.0 by Summit Research Services (Montrose, Colo.) was used for pharmacokinetic data analysis. All animals were treated as per National Institute of Health Guidelines for Animal Care and approved by California Institute of Technology Institutional Animal Care and Use Committee.

Polymer bound CPT for all nanoparticles displayed a biphasic profile with a fast redistribution phase (α) and a long elimination phase (β) (FIG. 18A). The elimination phase for medium and long MAP-CPT nanoparticles were particularly prolonged with half-lives of 16.6 and 17.6 h, respectively, and gave high area under the curve (AUC) values of 2298 and 3636 µg*h/ml, respectively. Additionally, they showed low volumes of distribution and clearance rates. 24 h after injection, 11.3% of the injected dose of the medium MAP-CPT nanoparticles and 20.5% of the injected dose of the long MAP-CPT nanoparticles were still circulating in plasma as polymer bound CPT. In contrast, mice injected with CPT alone at 10 mg/kg showed fast clearance, with an AUC of only 1.6 µg*h/ml and 0.01% of the injected dose remaining in circulation after 8 h. Targeting of medium MAP-CPT nanoparticles effected the pharmacokinetic profile by increasing the redistribution phase and prolonging the elimination phase to 21.2 h with a high AUC value of 2766 µg*h/ml. The amounts of unbound CPT in plasma for all nanoparticles were low at all time points (FIG. 18B).

Example 32

Determination of Maximum Tolerable Dose (MTD) in Nude Mice

MTD values were determined in female NCr nude mice and defined as the highest dose resulting in less than 15% body weight loss and with no treatment related deaths. In these experiments 12 weeks old female NCr nude mice were randomly divided into thirteen groups containing five mice each. Formulations medium MAP or nitroPBA-PEG at 200 mg/kg, short MAP-CPT nanoparticles at 10, 15 or 20 mg/kg (CPT basis), medium MAP-CPT nanoparticles at 8, 10 or 15 mg/kg (CPT basis), long MAP-CPT nanoparticles at 5, 8 or 10 mg/kg (CPT basis) and targeted MAP-CPT nanoparticles at 8 or 10 mg/kg (CPT basis) were administered on day 0 and day 7 via intravenous tail vein injection. All injections were formulated in 0.9 w/v % saline except for targeted MAP-CPT which was formulated in PBS, pH 7.4. Weight and health of the mice were recorded and monitored daily for 2 weeks after the start of the treatment. MTD was defined as the highest dose resulting in less than 15% body weight loss and with no treatment related deaths. Animals were euthanized when criteria for MTD was exceeded or at the end of the study by $CO_2$ asphyxiation.

Mice treated with medium MAP, nitroPBA-PEG, short, medium and long MAP-CPT and targeted MAP-CPT were weighed and monitored for health after two weekly doses on day 0 and day 7 (Table 6). The weight and health of the mice were unaffected by treatment at high doses of medium MAP or nitroPBA-PEG, indicating minimal toxicity for these polymeric components. For groups containing CPT, maximum weight loss appeared 3 to 5 days after each treatment. Most of the groups gained back the lost weight. If body weight loss continued and exceeded an average of 15%, then the study was concluded. Some mice in groups treated with medium MAP-CPT at 15 mg/kg and long MAP-CPT at 10 mg/kg showed diarrhea and appeared weak. All other mice appeared healthy. MTD values were found to be 20, 10, 8 and 8 mg/kg (on CPT basis) for short, medium, long MAP-CPT and targeted MAP-CPT respectively (Table 6).

TABLE 6

Treatment response for maximum tolerable dose (MTD) study

|  | Dose (mg/kg)[a] | Max % weight loss (day)[b] | Death |
|---|---|---|---|
| medium MAP | 200 | −1.1 (11) | 0 |
| nitroPBA-PEG | 200 | −0.5 (2) | 0 |
| short MAP-CPT | 10 | −4.5 (2) | 0 |
| short MAP-CPT | 15 | −6.1 (10) | 0 |
| short MAP-CPT | 20 | −10.2 (12) | 0 |
| medium MAP-CPT | 8 | −6.8 (10) | 0 |
| medium MAP-CPT | 10 | −14.9 (12) | 0 |
| medium MAP-CPT | 15 | −18.4 (4) | culled[c] |
| long MAP-CPT | 5 | −4.8 (4) | 0 |
| long MAP-CPT | 8 | −9.2 (12) | 0 |
| long MAP-CPT | 10 | −16.5 (10) | culled[c] |
| targeted MAP-CPT | 8 | −5.2 (4) | 0 |
| targeted MAP-CPT | 10 | −15.2 (9) | culled[c] |

[a]All groups containing MAP-CPT are based on mg CPT/kg.
[b]Maximum percent body weight loss.
[c]Animals culled due to exceeding 15% body weight loss.

Example 33

Biodistribution in Nude Mice

To assess the biodistribution targeted nanoparticles in mice 7 weeks old NCr nude mice were transplanted subcutaneously with 17β-estradiol pellets. After 2 days, BT-474 carcinoma cells suspended in RPMI-1640 medium were injected subcutaneously into the right front flank at 10 million cells/animal. Treatment began a day after the tumors reached an average size of 260 mm$^3$. Animals were randomized into two groups of six mice per group and treated via intravenous tail vein injections with either MAP-CPT nanoparticles at 5 mg CPT/kg (in PBS, pH 7.4) or targeted MAP-CPT nanoparticles at 5 mg CPT/kg and 29 mg Herceptin®/kg (in PBS, pH 7.4). After 4 h and 24 h, blood was collected from three animals from each group via saphenous vein bleed. Animals were then euthanized by $CO_2$ asphyxiation and perfused with PBS. Tumor, lung, heart, spleen, kidney and liver were harvested and sectioned into two equal sized pieces. One piece was embedded in Tissue-Tek® OCT (Sakura) and the other collected in Eppendorf tubes, both were frozen immediately at −80° C. until time for processing.

Organs were weighed and 100 mg of each were placed in Lysing Matrix A homogenizer tubes containing an added ¼ inch ceramic sphere (MP Biomedicals, Solon, Ohio). 1 ml of RIPA lysis buffer (Thermo Scientific) was added and tissues were homogenized using a FastPrep®-24 homogenizer (MP Biomedicals, Solon, Ohio) at 6 m/s for 30 s. This was repeated for 3 times with 1 min of cooling on ice in between each round. Samples were then centrifuged at 14,000 g for 15 min at 4° C. The amount of unconjugated CPT was determined by first mixing 10 μl of the supernatant with 10 μl of 0.1 N HCl and incubating at room temperature for 30 min. 80 μl of methanol was then added and the mixture incubated at room temperature for 3 h for protein precipitation. This mixture was centrifuged at 14,000 g for 10 min at 4° C., supernatant was filtered with a 0.45 μm filter (Millex-LH) and 10 μl of the resulting mixture injected into HPLC. The peak area of the eluted CPT (at 7.8 min) was compared to that of control. To measure the total amount of CPT, 10 μl of sample was mixed with 6.5 μl of 0.1 N NaOH. This solution was incubated at room temperature for 1 h for CPT to be released from parent polymer. 10 μl of 0.1 N HCl was then added to convert carboxylate CPT form to lactone form. 73.5 μl of methanol was subsequently added and mixture incubated for 3 h at room temperature. The sample was then centrifuged and processed as above.

Figure 19A:
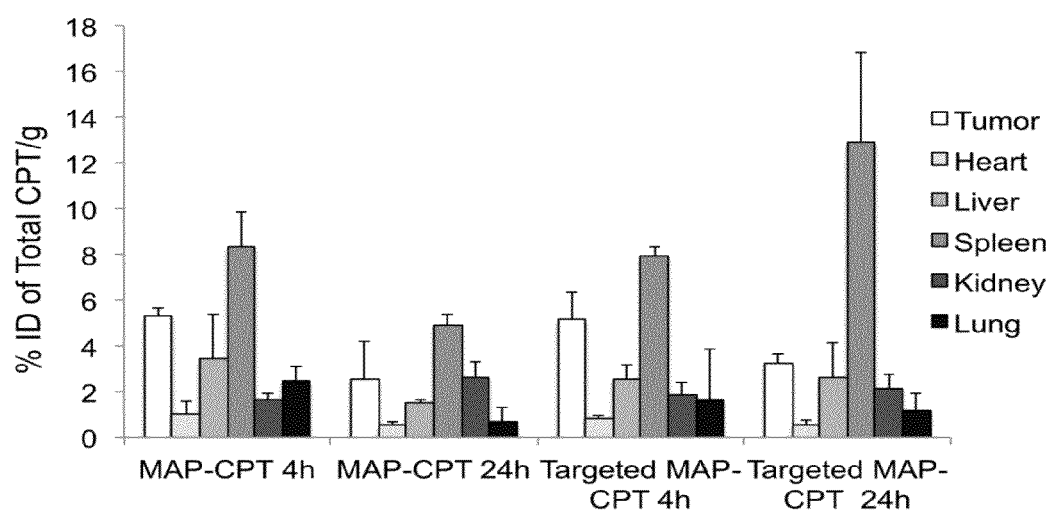
FIGS. 19A-D show the biodistribution of MAP-CPT (5 mg CPT/kg) and targeted MAP-CPT (5 mg CPT/kg, 29 mg Herceptin®/kg) nanoparticles after 4 and 24 h of treatment. (A) Percent injected dose (ID) of total CPT per gram of tumor, heart, liver, spleen, kidney or lung. (B) Percentage of total CPT in each organ that is unconjugated in tumor, heart, liver, spleen, kidney and lung. (C) Total concentration of CPT in plasma. (D) Percentage of total CPT that is unconjugated in plasma.

The average percentage injected dose (ID) of total CPT per gram of tumor, heart, liver, spleen, kidney and lung is shown in FIG. 19A. 4 h after dosing, 5.3 and 5.2% ID of total CPT were present per gram of tumor in mice treated with MAP-CPT nanoparticles and targeted MAP-CPT nanoparticles, respectively. 24 h after treatment, 2.6% ID of total CPT remained per gram of tumor for mice treated with MAP-CPT nanoparticles, while 3.2% ID of total CPT were found per gram of tumor for mice receiving targeted MAP-CPT nanoparticles. These data show that targeted nanoparticles of essentially the same size and surface charge of an untargeted version do not increase tumor localization over that of a non-targeted version, and is consistent with observations reported by others. Animals treated with MAP-CPT nanoparticles and targeted MAP-CPT nanoparticles gave similar distribution of CPT in heart, liver, kidney and lung. There was, however, a comparatively significant amount of total CPT accumulation in the spleen for targeted MAP-CPT versus non-targeted at 24 h. This effect has been observed previously for humanized antibodies in mice.

Figure 19B:
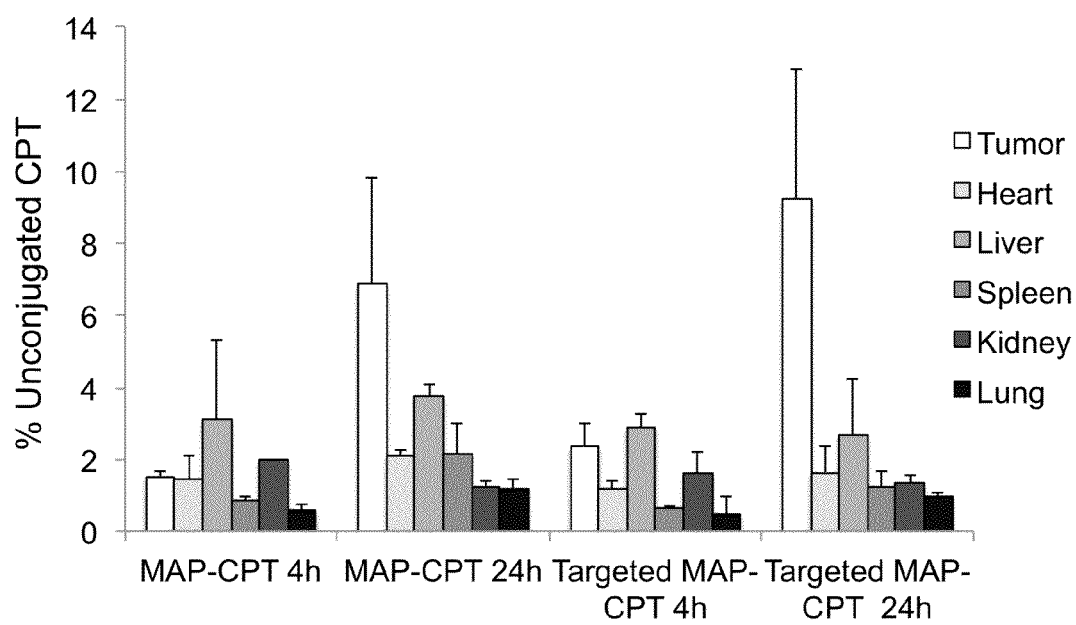

FIG. 19B shows the average percentage of unconjugated CPT in each organ for tumor, heart, liver, spleen, kidney and lung. The percentage unconjugated CPT in heart, liver, spleen, kidney and lung were low at both 4 h and 24 h, indicating fast clearance of free CPT from these organs. In tumor at 24 h, there were significantly higher percentages of unconjugated CPT for both MAP-CPT and targeted MAP-CPT nanoparticles compared to that at 4 h. The retention of free CPT within the tumors suggests cellular accumulation of CPT. The targeted nanoparticles show slightly higher percentage of unconjugated CPT in tumors for mice over the non-targeted nanoparticles at both 4 and 24 h.

Figure 19C:
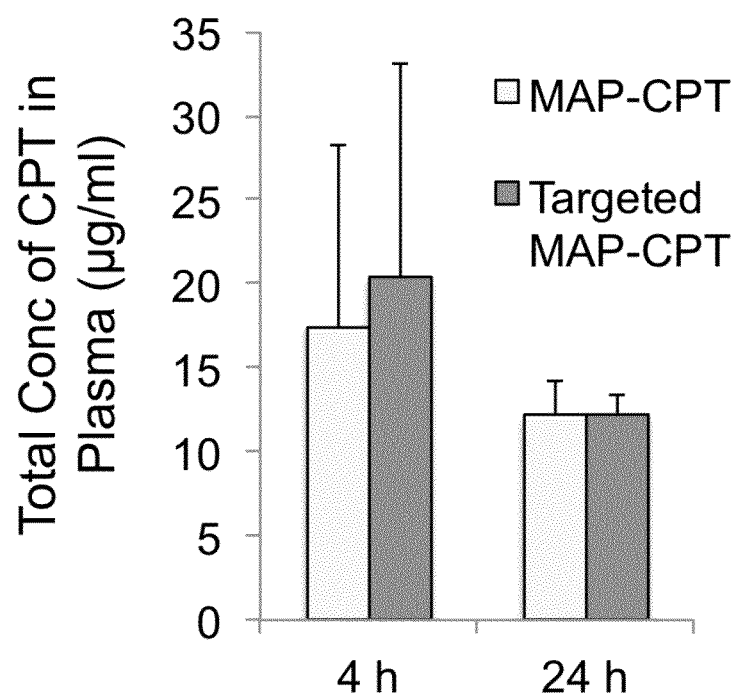
Figure 19D:
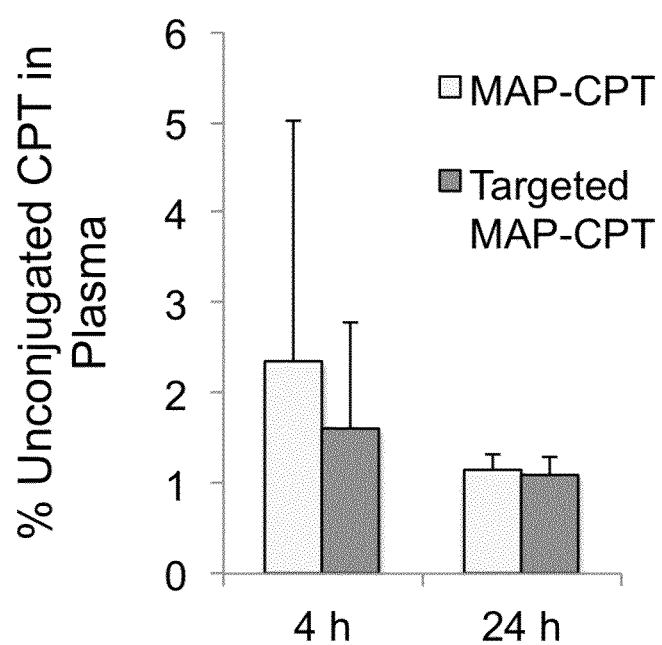

The total concentration of CPT in plasma and percentage of total CPT that is unconjugated in plasma were similar for both the MAP-CPT and targeted MAP-CPT nanoparticles (FIG. 19C). After 4 h, 17 and 20 μg/ml of total CPT remained in plasma for MAP-CPT and targeted MAP-CPT nanoparticles respectively. After 24 h, the amounts of total CPT remaining in plasma were the same for both MAP-CPT and targeted MAP-CPT nanoparticles at 12 μg/ml. The percentage of total CPT that is unconjugated in plasma was below 3% for all conditions indicating small release and fast clearance of unconjugated CPT from plasma (FIG. 19D).

Example 33

Treatment of Tumors with Targeted Nanoparticles

BT-474 tumor bearing NCr nude mice were treated with either MAP-CPT (5 mg CPT/kg) or targeted MAP-CPT (5 mg CPT/kg, 29 mg Herceptin/kg). After 4 and 24 h, mice were euthanized and tumors were removed and sectioned using a cryostat to a thickness of 20-30 μm. The tumor sections were placed on Superfrost Plus slides (Fisher Scientific, Hampton, N.H.) and stored at −80° C. until time for processing. Slides were defrosted and tissue sections were fixed directly onto the slide for 15 min with a 10% formalin solution. The slides were then washed three times with PBS for 5 min each, and blocked for 1 h in a 5% goat serum blocking buffer. CPT is naturally fluorescent with emission at 440 nm. To identify the location of MAP, the PEG within MAP was stained with a rat anti-PEG primary antibody that recognizes internal PEG units at 14 µg/ml and incubated at 4° C. overnight. This was followed by three PBS washes and 1 h incubation with 2 µg/ml of Alexa Fluor® 488 goat anti-rat IgM secondary antibody. The slides were then washed three times with PBS, and incubated for 1 h with 2 µg/ml of Alexa Fluor® 633 goat anti-human IgG secondary antibody to visualize Herceptin®. The slides were washed three more times with PBS, mounted with a Prolong Gold Antifade reagent and stored at 4° C. until time for imaging. Images were acquired with a Zeiss LSM 510 Meta Confocal Microscope (Carl Zeiss, Germany) using a 63× Plan-Neofluar oil objective. 2-Photon excitation at 720 nm (emission filter BP 390-465 nm) was used to detect CPT. Excitation at 488 nm (emission filter LP 530) and at 633 nm (emission filter BP 645-700 nm) were used to detect PEG and Herceptin respectively. All laser and gain settings were set at the beginning of imaging and were unchanged. Image analysis was performed on Zeiss lsm image browser.

Figure 20:
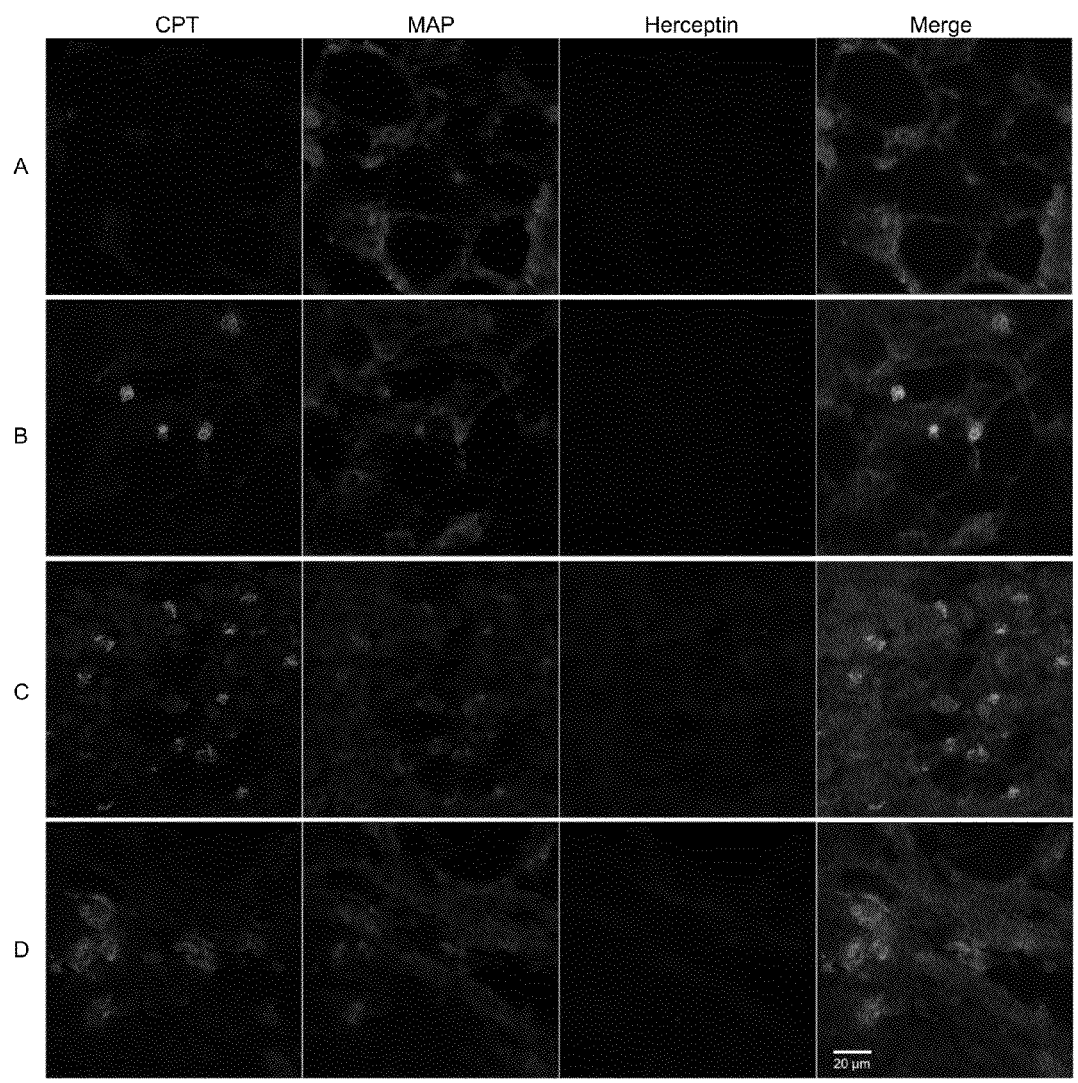
FIG. 20 depicts confocal immunofluorescence microscopy of BT-474 tumor sections taken from NCr nude mice treated with (A) MAP-CPT (5 mg CPT/kg) at 4 h (B) MAP-CPT (5 mg CPT/kg) at 24 h. (C) Targeted MAP-CPT (5 mg CPT/kg, 29 mg Herceptin®/kg) at 4 h. (D) Targeted MAP-CPT (5 mg CPT/kg, 29 mg Herceptin®/kg) at 24 h. Left panel emission 440 nm (CPT, pink), center left panel emission 519 nm (MAP, green), center right panel emission 647 nm (Herceptin®, blue), right panel overlay of images.

FIG. 20A shows tumor section of mice treated with MAP-CPT nanoparticles after 4 h. CPT signal was disperse. Signals for CPT and MAP appeared to colocalize in the merged image. 24 h after injection, there was accumulation of CPT signal in the form of punctate spots (FIG. 20B). The merged image suggests colocalization of CPT and MAP. For mice treated with targeted MAP-CPT nanoparticles, spots indicating CPT accumulation were observed after both 4 and 24 h of treatment (FIGS. 20C and 20D). In the merged images, there was colocalization of CPT and MAP signals. The presence of Herceptin in targeted MAP-CPT nanoparticles is indicated by the strong blue signals in the Herceptin channel compared with weak background signals in the non-targeted version.

Example 33

Antitumor Efficacy Study in Nude Mice

BT-474 is one of the most resistant breast cancers to anti-cancer drugs including camptothecin. To promote tumor growth in nude mice, 17β-estradiol pellets were implanted into 7 weeks old NCr nude mice two days prior to BT-474 tumor cell implantation. On day 0 (five days after implantation), tumor sizes of each group averaged 250 mm. Treatments began on day 1. Animals were randomly divided into nine groups with six to eight mice per group and treated with either, MAP-CPT nanoparticles at 1 mg or 8 mg/kg (CPT basis, in PBS, pH 7.4), CPT at 8 mg/kg (dissolved in 20% DMSO, 20% PEG 400, 30% ethanol and 30% 10 mM pH 3.5 phosphoric acid), Irinotecan at 80 mg/kg (in 5 w/v % dextrose solution, D5W), Herceptin® at 2.9 or 5.9 mg/kg (in PBS, pH 7.4), targeted MAP-CPT nanoparticles at 0.5 mg CPT/kg and 2.9 mg Herceptin®/kg or 1 mg CPT/kg and 5.9 mg Herceptin®/kg (in PBS, pH 7.4), or saline. All treatments were freshly prepared and given via intravenous tail vein injection. Injections were standardized at 150 µl per 20 g body weight of mice. Treatments containing Herceptin® were given once per week for 2 weeks, all other groups were given once per week for 3 weeks. Tumor sizes were recorded three times a week using caliper measurements (length×width$_2$/2) and health of the animals was continuously monitored. Animals were euthanized when tumor volumes exceeded 1000 mm$^3$. Six weeks after beginning of the treatment, animals were euthanized by $CO_2$ asphyxiation. The results from this study are presented in FIG. 21 and Table 7.

Figure 21:
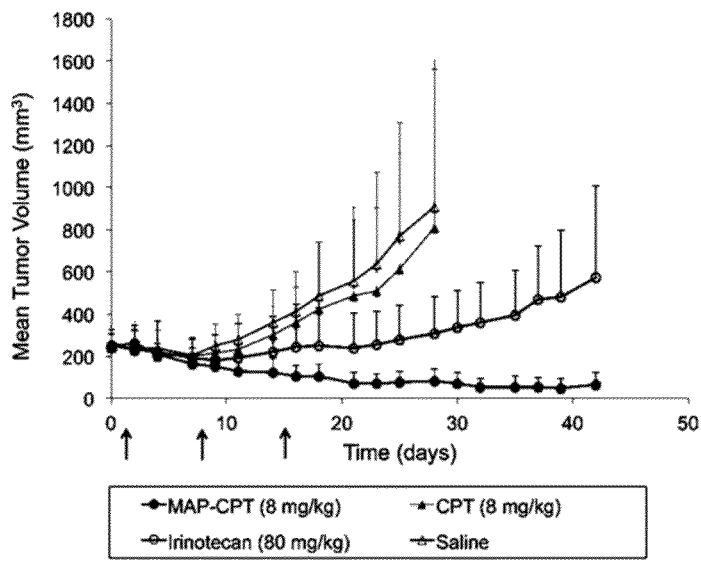
FIG. 21 shows the antitumor efficacy study in NCr nude mice bearing BT-474 xenograft tumors. Mean tumor volume as a function time, groups containing Herceptin received 2 weekly doses, all other groups received 3 weekly doses.
Figure 21:
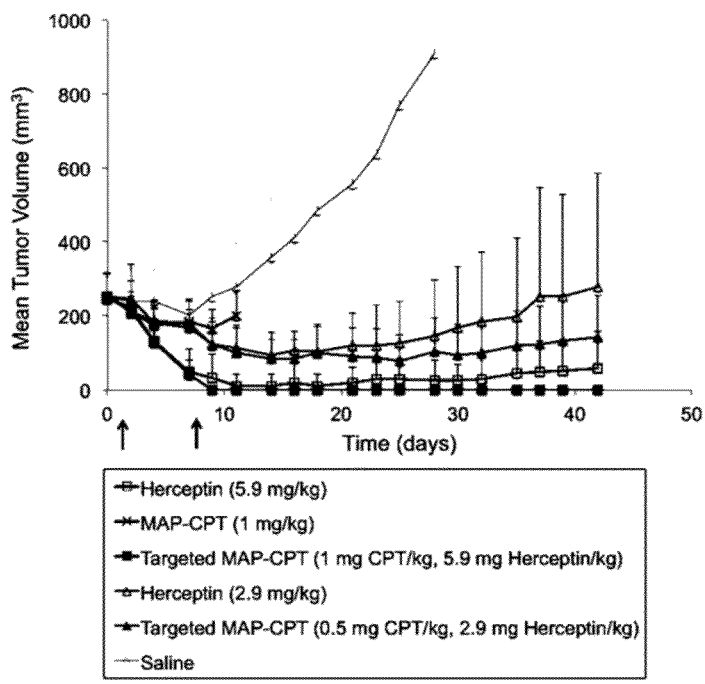

Tumors in the control group administered with saline grew rapidly (FIG. 21). After 28 days, five out of eight mice had tumors exceeding size limit of 1000 mm$^3$. All animals in this group were euthanized at this time.

The group treated with CPT (8 mg/kg) resulted in no tumor inhibition compared to that of the control group (P>0.05). One and three treatment related deaths were recorded on day 9 and 16, respectively, as well as four euthanizations due to exceeding the tumor size limit on day 28. None of the animals survived to the end of the study.

Mice treated with Irinotecan at 80 mg/kg showed non-significant tumor inhibition compared to control group (P>0.05). One treatment related death occurred on day 11. Tumor sizes reached an average of 575 mm$^3$ by the end of the study.

Animals receiving MAP-CPT nanoparticles at 8 mg CPT/kg showed highly significant tumor inhibition compared to that of control group (P<0.01). By the end of the study the mean tumor size reduced to 63 mm$^3$ and three out of the eight mice treated had tumor sizes regressed to zero. Although no deaths occurred in MTD study using non-tumor bearing NCr nude mice treated with MAP-CPT at 8 mg CPT/kg, one death occurred due to weight loss in this study on day 21. This may be because of the added tumor burden in this study and/or because mice used in this study were 7 weeks old, while in MTD studies, 12 weeks old mice were used.

Figure 22:
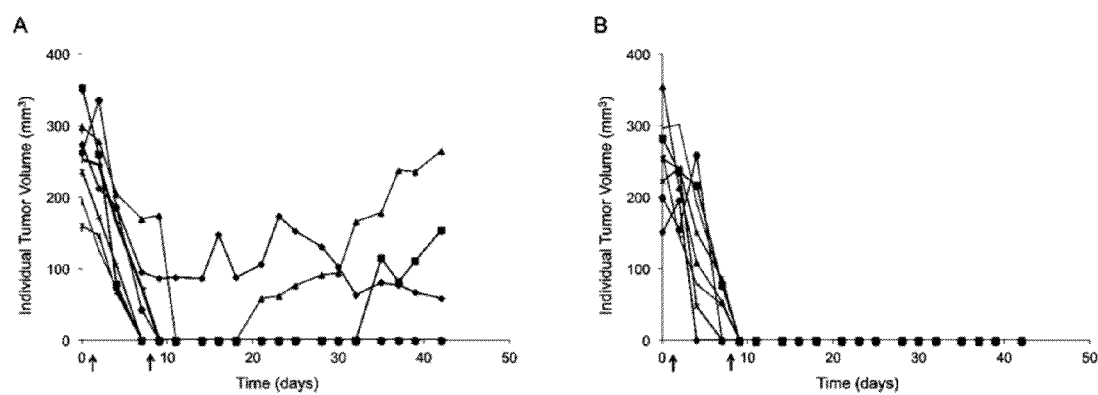
FIG. 22 shows the antitumor efficacy results for NCr nude mice treated with (A) Herceptin at 5.9 mg/kg. (B) Targeted MAP-CPT nanoparticles (5.9 mg Herceptin®/kg and 1 mg CPT/kg).

Animals treated with Herceptin® at 5.9 mg/kg showed highly significant tumor inhibition compared to control group (P<0.01). On day 11 of treatment, seven out of the eight animals treated had tumors regressed to zero. However, by the end of the study, two of the regressed tumors relapsed resulting in a total of five animals with tumors at zero volume and a group mean tumor volume of 60 mm$^3$ (FIG. 22). Mice treated with MAP-CPT nanoparticles at 1 mg CPT/kg were terminated early due to no observed antitumor effects. Nevertheless, when Herceptin® at 5.9 mg/kg was added as a targeting agent via a nitroPBA-BA linker onto MAP-CPT nanoparticles at a low CPT dosage of 1 mg/kg (targeted MAP-CPT nanoparticles at 5.9 mg Herceptin®/kg and 1 mg CPT/kg), all tumors regressed to zero on day 9 of treatment and remained at zero by the end of the study (FIG. 22). One non-treatment related death occurred on day 37. This result is highly significant compared to control group (P<0.01). The combination of results observed for these three groups indicate that there is improved efficacy of MAP-CPT nanoparticles by the addition of the Herceptin® targeting agent in addition to the intrinsic activity of the Herceptin®.

Animals treated with Herceptin® at 2.9 mg/kg resulted in two animals having tumors regressed to zero by the end of study. However, the average tumor size increased from the beginning of the study to 278 mm$^3$. This result is significant compared to control group (0.01≤P≤0.05). When animals were treated with targeted MAP-CPT nanoparticles containing 0.5 mg CPT/kg and 2.9 mg Herceptin®/kg, two tumors regressed to zero. The average tumor size reduced to 141 mm$^3$ by the end of the study. This result is highly significant compared to control group (P<0.01). These results further suggest the benefits of targeting in tumor inhibition.

Five weeks after 17β-estradiol pellets implantation, several mice irrespective of treatment groups were observed to have distended bladder and abdominal bloating. This was likely due to the use of 17β-estradiol pellets, which causes hydronephrosis and urine retention in athymic nude mice. Six weeks after treatment, conditions became worse and more mice were observed to develop distended bladders and abdominal bloating, thus animals were euthanized and the experiment was terminated.

TABLE 7

Anti-tumor efficacy study in NCr nude mice bearing BT-474 xenograft tumors

| | $N_{begin}/N_{end}{}^a$ | $N_{TRD}/N_{NTRD}/N_{euthan}{}^b$ | Mean tumor volume (mm$^3$) | Median tumor volume (mm$^3$) | $N_{reg\ to\ zero}{}^c$ | P vs saline$^d$ |
|---|---|---|---|---|---|---|
| MAP-CPT (8 mg/kg) | 8/7 | 1/0/0 | 63 | 68 | 3 | 0.002 |
| Irinotecan (80 mg/kg) | 8/7 | 1/0/0 | 575 | 479 | 0 | 0.242 |
| CPT (8 mg/kg) | 8/0 | 4/0/4 | 808 | 417 | 0 | 0.781 |
| Herceptin (5.9 mg/kg) | 8/8 | 0/0/0 | 60 | 0 | 5 | 0.003 |
| Targeted MAP-CPT (1 mg CPT/kg, 5.9 mg Herceptin/kg) | 8/7 | 0/1/0 | 0 | 0 | 7 | 0.001 |
| Herceptin (2.9 mg/kg) | 6/6 | 0/0/0 | 278 | 245 | 2 | 0.026 |
| Targeted MAP-CPT (0.5 mg CPT/kg, 2.9 mg Herceptin/kg) | 6/6 | 0/0/0 | 141 | 187 | 2 | 0.005 |
| Saline | 8/0 | 0/0/8 | 911 | 1087 | 0 | — |

$^a$N$_{begin}$ is number of animals at beginning of study, N$_{end}$ is number of animals surviving to end of study.
$^b$N$_{TRD}$ is number of treatment related death, N$_{NTRD}$ is number of non-treatment related death, N$_{euthan}$ is number of animals euthanized due to exceeding tumor size limit of 1000 mm$^3$.
$^c$N$_{reg\ to\ zero}$ is number of animals with tumors regressed to zero at the end of study.

The examples set forth above are provided to give those of ordinary skill in the art a complete disclosure and description of how to make and use the embodiments of the particles, compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

What is claimed:

1. A nanoparticle comprising a polymer containing a polyol and a polymer containing a nitrophenylboronic acid,
   wherein the polymer containing a nitrophenylboronic acid is coupled to the polymer containing a polyol with a reversible covalent linkage, and
   wherein the nanoparticle is configured to present the polymer containing a nitrophenylboronic acid to an environment external to the nanoparticle.

2. The nanoparticle of claim 1, wherein the polymer containing a polyol comprises one or more of at least one of the following structural units $$-\!\!\left(\!\!\boxed{A}\!-\!B\!\right)\!\!- \quad (I)$$

$$-\!\!\left(\!\!\boxed{A}\!\right)\!\!\left(\!B\!\right)\!\!- \quad (II)$$

$$-\!\!\left(\!\!\boxed{A}\!\right)\!\!- \quad (III)$$

wherein
A is an organic moiety of formula $$R_1 -\!\!\left[\!\!\begin{array}{c}OH\\|\\C\\|\\X\end{array}\!\!-\!\!\begin{array}{c}XY\\|\\C\end{array}\!\!\right]\!\!- R_2 \quad (IV)$$

in which
  $R_1$ and $R_2$ are independently selected from any carbon-based or organic group with a molecular weight of about 10 kDa or less;
  X is independently selected from an aliphatic group containing one or more of —H, —F, —C, —N or —O; and
  Y is independently selected from —OH or an organic moiety presenting an —OH, and
  B is an organic moiety linking one of the $R_1$ and $R_2$ of a first said moiety A with one of the $R_1$ and $R_2$ of a second said moiety A in the polymer.

3. The nanoparticle of claim 2, wherein $R_1$ and $R_2$ independently have the formula:

$$Z\!\!\underset{d}{\diagdown}\!\!\underset{e}{\overset{OH}{\diagup\!\!\diagdown}}\!\!\underset{f}{\diagup}\!Z_1 \quad (V)$$

wherein
  d is from 0 to 100;
  e is from 0 to 100;
  f is from 0 to 100;
  Z is a covalent bond linking one organic moiety to another, and
  $Z_1$ is independently selected from —$NH_2$, —OH, —SH, and —COOH.

4. The nanoparticle of claim 2, wherein
  X is $C_nH_{2n+1}$, in which n is to 0-5; and
wherein
  Y is —OH.

5. The nanoparticle of claim 2, wherein A is independently selected from the group consisting of

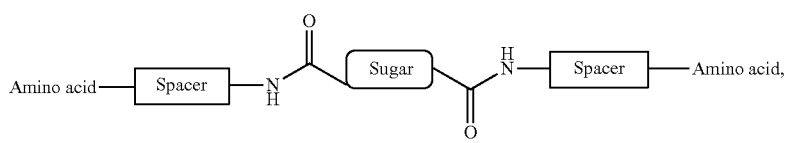

VI

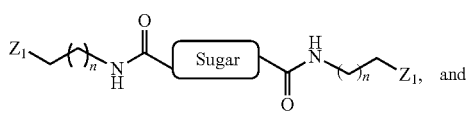 and

VII

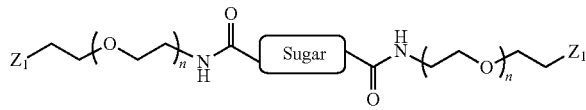

VIII wherein
  the spacer is independently selected from any organic group;
  the amino acid is selected from any organic group bearing a free amine and a free carboxylic acid group;
  n is 1-20; and
  $Z_1$ is independently selected from —$NH_2$, —OH, —SH, and —COOH.

6. The nanoparticle of claim 5, wherein A is independently selected from

7. The nanoparticle of claim 2, wherein B is

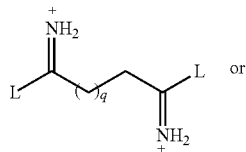 or (XXIII)

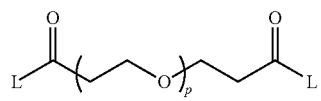

(XIV)

in which q is 1-20;

p is 20-200; and

L is a leaving group.

IX

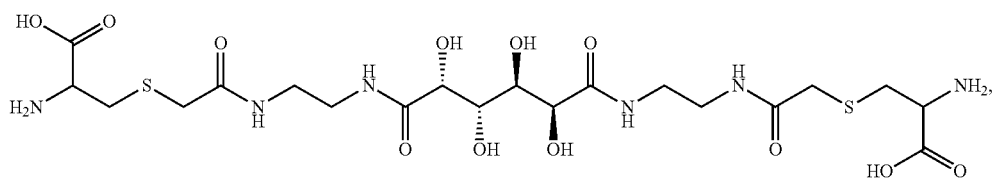

X

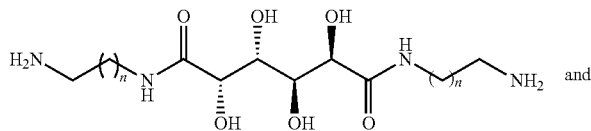 and

XI

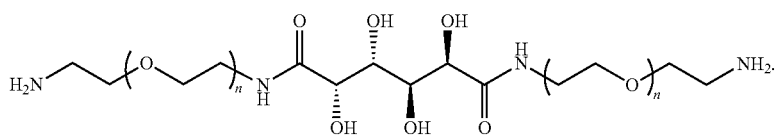

8. The nanoparticle of claim 2, wherein the structural unit of formula (I) is:

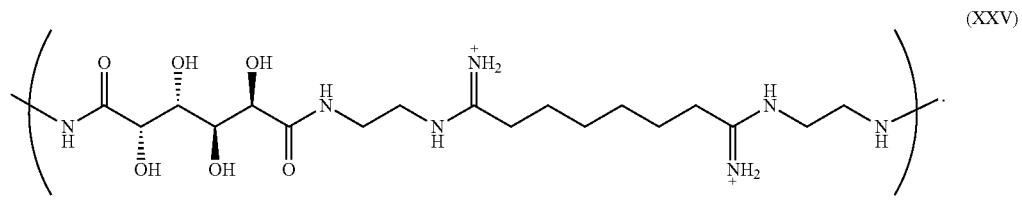

(XXV)

9. The nanoparticle of claim 2, wherein the structural unit of formula (II) is:

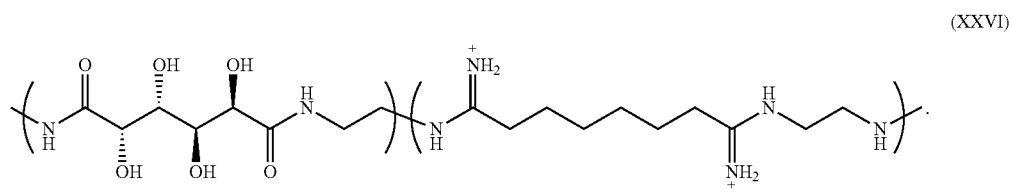

(XXVI)

10. The nanoparticle of claim 2, wherein the structural unit of formula (III) is:

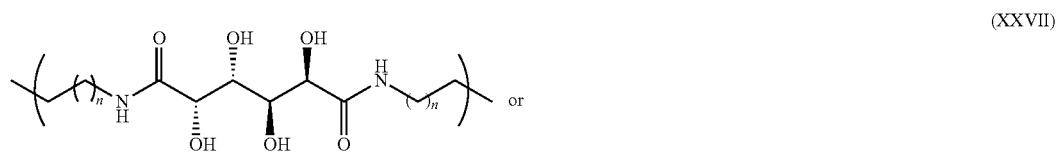

(XXVII)

(XXVIII)

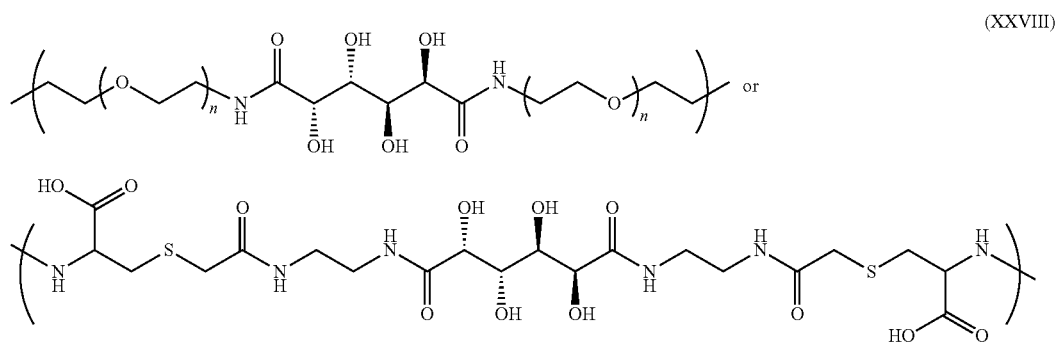

in which
n is 1-20.

11. The nanoparticle of claim 1, wherein the polymer containing a polyol is

12. The nanoparticle of claim 1, wherein the polymer containing a nitrophenylboronic acid comprises at least one terminal nitrophenylboronic acid group and has the general formula:

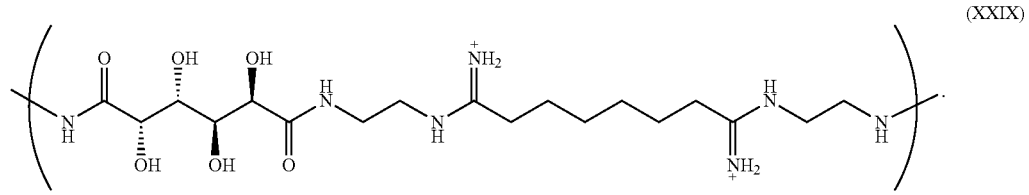

(XXIX)

(XXX)

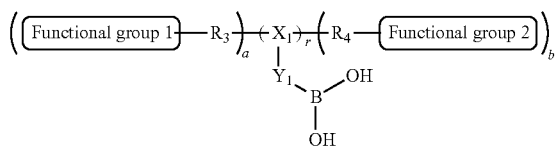

wherein
$R_3$ and $R_4$ are independently an hydrophilic organic polymer,
$X_1$ is an organic moiety containing one or more of —C, —N, or —B,
$Y_1$ is a phenyl group having one or more nitro groups,
r is 1-1000,
a 0, 1, 2, or 3,
b is 1, 2, or 3, and
wherein functional group 1 and functional group 2 are the same or different and independently comprise —B(OH)$_2$, —OCH$_3$, —(X$_1$)—(Y$_1$)—B(OH)$_2$, —COOH, —NH$_2$, or —OH.

13. The nanoparticle of claim 12, wherein $R_3$ and $R_4$ are (CH$_2$CH$_2$O)$_t$, where t is from 2 to 2000.

14. The nanoparticle of claim 12, wherein $X_1$ is —NH—C(=O)—, —S—S—, —C(=O)—NH—, —O—C(=O)— or —C(=O)—O— and $Y_1$ is a phenyl group having one or more nitro groups.

15. The nanoparticle of claim 12, wherein r=1, a=0 and b=1.

16. The nanoparticle of claim 12, wherein functional group 1 and functional group 2 are the same or different and are independently —B(OH)$_2$, —OCH$_3$, —OH, or —COOH.

17. The nanoparticle of claim 12, wherein the polymer containing a nitrophenylboronic acid is:

(XXXIII)

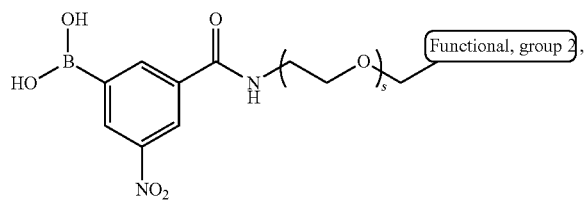

(XXXIV)

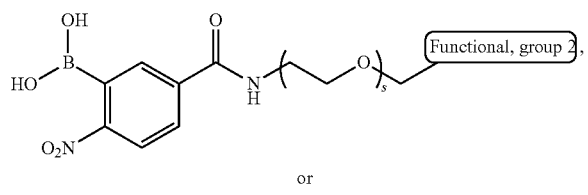

or (XXXV)

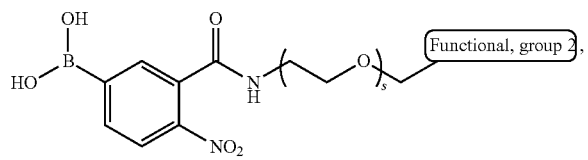

wherein s is a number from 20 to 300.

18. The nanoparticle of claim 1, further comprising a compound, wherein the compound is a therapeutic agent.

19. The nanoparticle of claim 18, wherein the therapeutic agent is a small molecule chemotherapeutic agent or a polynucleotide.

20. The nanoparticle of claim 19, wherein the polynucleotide is interfering RNA.

21. The nanoparticle of claim 18, wherein the small molecule chemotherapeutic is camptothecin, an epothilone, a taxane or any combination thereof.

22. A composition comprising the nanoparticle of claim 1 and a suitable vehicle and/or excipient.

23. The composition of claim 22, wherein the composition is a pharmaceutical composition and the suitable vehicle and/or excipient is a pharmaceutically acceptable vehicle and/or excipient.

24. The composition of claim 23, wherein the nanoparticle further comprises [10]B as part of at least one polymer containing a nitrophenylboronic acid the composition being formulated for in vivo boron neutron activation therapy.

25. A method to deliver a compound to a target, the method comprising contacting the target with the nanoparticle of claim 18.

26. The method of claim 25, wherein the target is a cancer cell within the body of a mammal.

27. A system to deliver a compound to a target, the system comprising
at least one polymer containing a polyol and at least one polymer containing a nitrophenylboronic acid capable of reciprocal binding through a reversible covalent linkage,
the at least one polymer containing a polyol and the at least one polymer containing a nitrophenylboronic acid to be assembled with the compound in the nanoparticle of claim 18 to be used to deliver the compound to the target.

28. A method to administer a compound to an individual, the method comprising
administering to the individual the nanoparticle of claim 18 comprising the compound.

29. A system for administering a compound to an individual, the system comprising
at least one polymer containing a polyol and at least one polymer containing a nitrophenylboronic acid capable of reciprocal binding through a reversible covalent linkage,
the at least one polymer containing a polyol and polymer containing a nitrophenylboronic acid to be assembled with the compound in a nanoparticle according to claim 18, to be administered to the individual.

30. The nanoparticle of claim 17, wherein the polymer containing a nitrophenylboronic acid is:

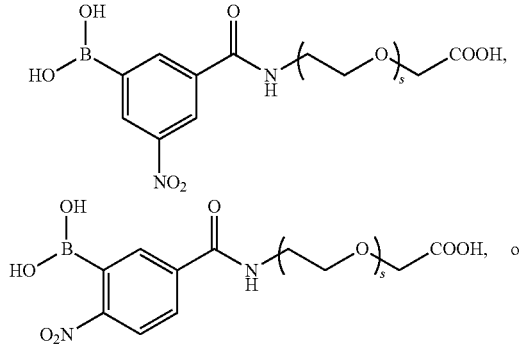

-continued
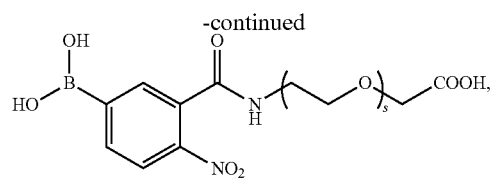
wherein s is a number from 20 to 300.
* * * * *